US008722044B2

(12) United States Patent
Almagro et al.

(10) Patent No.: US 8,722,044 B2
(45) Date of Patent: May 13, 2014

(54) HUMAN TISSUE FACTOR ANTIBODY AND USES THEREOF

(75) Inventors: Juan Carlos Almagro, Brookline, MA (US); Glenn Mark Anderson, Radnor, PA (US); Ellen Chi, San Diego, CA (US); Christian Martinez, San Diego, CA (US); Gopalan Raghunathan, San Diego, CA (US); Ronald Swanson, San Diego, CA (US); Alexey Teplyakov, Radnor, PA (US); Kam-Fai Tse, Radnor, PA (US); Sheng-Jiun Wu, Radnor, PA (US); Hong Mimi Zhou, San Diego, CA (US)

(73) Assignee: Janssen Biotech, Inc., Horsham, PA (US)

(*) Notice: Subject to any disclaimer, the term of this patent is extended or adjusted under 35 U.S.C. 154(b) by 0 days.

(21) Appl. No.: 13/398,881

(22) Filed: Feb. 17, 2012

(65) Prior Publication Data
US 2012/0237528 A1 Sep. 20, 2012

Related U.S. Application Data

(60) Provisional application No. 61/452,674, filed on Mar. 15, 2011.

(51) Int. Cl.
*A61K 39/395* (2006.01)
*C07K 16/36* (2006.01)
*C07K 16/28* (2006.01)
*A61K 39/00* (2006.01)

(52) U.S. Cl.
CPC ............... *C07K 16/36* (2013.01); *C07K 16/28* (2013.01); *C07K 2317/24* (2013.01); *A61K 2039/505* (2013.01)
USPC ................ 424/133.1; 424/141.1; 424/145.1; 424/146.1; 424/155.1; 536/23.53; 435/328; 435/337

(58) Field of Classification Search
None
See application file for complete search history.

(56) References Cited

U.S. PATENT DOCUMENTS

| | | | |
|---|---|---|---|
| 5,223,427 A * | 6/1993 | Edgington et al. ............ 435/337 |
| 5,589,173 A | 12/1996 | O'Brien et al. | |
| 5,726,147 A | 3/1998 | Ruf et al. | |
| 5,766,591 A | 6/1998 | Brooks et al. | |
| 5,986,065 A | 11/1999 | Wong et al. | |
| 6,001,978 A | 12/1999 | Edgington et al. | |
| 6,036,955 A | 3/2000 | Thorpe et al. | |
| 6,238,878 B1 | 5/2001 | Jakobsen et al. | |
| 6,274,142 B1 | 8/2001 | O'Brien et al. | |
| 6,342,219 B1 | 1/2002 | Thorpe et al. | |
| 6,555,319 B2 | 4/2003 | Wong et al. | |
| 6,677,436 B1 | 1/2004 | Sato et al. | |
| 6,703,494 B2 | 3/2004 | Kirchhofer et al. | |
| 7,235,380 B1 | 6/2007 | Joliffe et al. | |
| 7,605,235 B2 | 10/2009 | Anderson et al. | |
| 7,662,925 B2 | 2/2010 | Lazar et al. | |
| 2009/0055944 A1 | 2/2009 | Korman et al. | |
| 2009/0081200 A1 | 3/2009 | Wang | |
| 2009/0118127 A1 * | 5/2009 | Raghunathan ............ 506/2 |
| 2009/0169547 A1 | 7/2009 | Sahin et al. | |
| 2010/0028358 A1 | 2/2010 | Ruf et al. | |

FOREIGN PATENT DOCUMENTS

| | | |
|---|---|---|
| EP | 0833911 B1 | 6/1996 |
| EP | 1069185 A1 | 2/1999 |
| WO | WO 88/07543 A1 | 10/1988 |
| WO | WO 91/09968 A1 | 7/1991 |
| WO | WO 94/05328 A1 | 3/1994 |
| WO | WO 94/11029 A1 | 5/1994 |
| WO | WO 9640921 A1 | 12/1996 |
| WO | WO 01/70984 A2 | 9/2001 |
| WO | WO 01/24626 A1 | 12/2001 |
| WO | WO 03/018771 A2 | 3/2003 |
| WO | WO 03/029295 A1 | 4/2003 |
| WO | WO 03037911 A2 | 5/2003 |
| WO | WO 2004039842 A2 | 5/2004 |
| WO | WO 2004094475 A2 | 11/2004 |
| WO | WO 95/25543 A1 | 9/2005 |
| WO | WO 2007/056352 A3 | 5/2007 |
| WO | WO 2007056352 A2 * | 5/2007 |
| WO | WO 2010/066803 A2 | 6/2010 |

OTHER PUBLICATIONS

Janeway et al., Immunobiology, 3rd edition, 1997, Garland Press, pp. 3:1-3:11.*
Rudikoff et al., Proc Natl Acad Sci USA, 1982, 79:1979-1983.*
Portolano et al., J. Immunol., 1993, 150:880-887.*
William E. Paul, M.D. ed., Fundamental Immunology, 3d ed. 1993, p. 242.*
Fransson et al., J Mol Biol. Apr. 30, 2010;398(2):214-31. doi: 10.1016/j.jmb.2010.03.004. Epub Mar. 10, 2010.*
Definition of "derived" from the Merriam-Webster online dictionary, m-w.com, downloaded Apr. 15, 2013.*
Ngo, C. et. al.: "CTNO 859, A Humanized Anti-tissue Factor Monoclonal Antibody Inhibits Lung Metastasis and Tumor Growth in MDA-MB-231 Breast Cancer Xonograft Models" Pathophysiology of Haemostasis and Thrombosis, Karger, CH, vol. 33, No. Suppl 1 Sep. 2003, p. 71 XP009082975, ISSN: 1424-8832.
Ngo, Cam V. et. al: "CTNO 859, A Humanized Anti-tissue Factor Monoclonal Anitbody, is a Potent Inhibitor of Breast Cancer Metastasis and Tumor Growth in Xenograft Models" International Journal of Cancer, vol. 120, No. 6, Mar. 2007, pp. 1261-1267, XP002432052, ISSN: 0020-7136.
Louis M. Weiner, "An Overview of Monoclonal Antibody Therapy of Cancer," Seminars in Incology, 26(4): 41-50 (1999).
Rakesh K. Jain, "Barriers to Drug Delivery in Solid Tumors," Scientific American, 271(1): 58-65 (1994).

(Continued)

Primary Examiner — Michael Szperka

(57) ABSTRACT

The invention relates to a humanized form of an antibody capable of preventing tissue factor (coagulation factor F3) signaling but which does not interfere with Factor VII binding or FX binding to tissue factor and does not prolong coagulation time. The antibody of the invention is useful in treating conditions, such as tumor progression, in which the associated cells express tissue factor and tissue factor signaling occurs.

19 Claims, 8 Drawing Sheets

(56) References Cited

OTHER PUBLICATIONS

Robert O. Dillmann, "Monoclonal Antibodies for Treating Cancer," Annals of Internal Medicine, 111: 592-603 (1989).
Fernandez et al., "Tissue factor and angiogenesis in cancer," Current Opinion in Hematology, 9:401-406 (2002).
Kakkar et al., et al., "Role of tissue factor expression on tumour cell invasion and growth of experimental pancreatic adenocarcinoma," British Journal of Surgery, 86: 890-894 (1999).
Trisha Gura, "Systems for Identifying New Drugs are Often Faulty," Science, 273: 1041-1042 (1997).
http://www.ncbi.nlm.nih.gov/entrez/query—cancer.
Reff et al., "A review of modifications to recombinant antibodies: attempt to increase efficacy in oncology applications", *Critical Reviews in Oncology/Hemtaology*, vol. 40, pp. 25-35, 2001.
Rudikoff et al., "Single amino acid substitution altering antigen-binding specificity", *Proc. Natl Acad Sci USA* vol. 79, p. 1979, 1982.
MacCallum et al., "Antibody-antigen Interactions: Contact Analysis and Binding Site Topography", *Journal of Molecular Biology*, vol. 262, pp. 732-745, 1996.
Pascalis et al., "Grafting of "Abbreaviated" Complemntarity-Determining Regions Containing Specificity-Determining Residues Essential for Ligand Contact to Engineer a Less Immunogenic Humanized Monoclonal Antibody", *The Journal of Immunology*, vol. 169, pp. 3076-3084, 2002.
Casset et al., "A peptide mimetic of an anti-CD4 monoclonal antibody by rational design", *BBRC*, vol. 307, pp. 198-205, 2003.
Vajdos et al., "Comprehensive Functional Maps of the Antigen-binding Site of an Anti-ErbB2 Antibody Obtained with Shotgun Scanning Mutagenesis", *Journal of Molecular Biology*, vol. 320, pp. 415-428, 2002.
Chen et al., "Selection and Analysis of an Optimized Anti-VEGF antibody: Crystal Structure of an Affinity—matured Fab in Complex with Antigen", *Journal of Molecular Biology*, vol. 293, pp. 865-881, 1999.
Wu et al., "Humanization of a Murine Monoclonal Antibody by Simultaneous Optimization of Framework and CDR Residues", *Journal of Molecular Biology*, vol. 294, pp. 151-162, 1999.
Holm et al., "Functional mapping and single chain construction of the anti-cytokeratin 8 monoclonal antibody TS1", *Molecular Immunology*, vol. 44, pp. 1075-1084, 2007.
Mueller et al., "Expression of tissue factor by melanoma cells promotes efficient hematogenous metastasis", *Proc. Natl. Acad. Sci USA*, vol. 89, pp. 11832-11836, 1992.
Ruf, Wolfram et al.,"Purification, sequence and crystallization of an anti-tissue factor", Journal of Crystal Growth 122, pp. 253-264, 1992.
Morrisey et al., "Monoclonal antibody analysis of purified and cell-associated tissue factor", Thrombosis Research 52:2, pp. 247-2611988.
Morrisey et al., "Molecular cloning of the cDNA for tissue factor, the cellular receptor for the initiation of the coagulation protease cascade", Cell 50: pp. 129-135, 1987.
Owens et al., "The genetic engineering of monoclonal antibodies", Journal of Immunological Methods 168: pp. 149-165, 1994.
Ruf et al., "An anti-tissue factor monoclonal antibody which inhibits TF-VIIa complex is a potent anticoagulant in plasma", Thromobosis and Haemostasis 66: pp. 529-533 1991.
Winter et al., "Humanized antibodies", Immunology Today, 14: pp. 243-246 1993.
Fiore, Martine et al., An unusual antibody that blocks tissue factor/factor VIIa function by inhibiting cleavage only of macromolecular substrates, Blood, vol. 80, No. 12, pp. 3127-3134, 1992.
Ragni, Massimo et al., "Monoclonal antibody tissue factor shorten tissue plasminogen activator lysis time and prevents reocculusion in a rabbit model of carotid artery thrombosis" Circulation, vol. 93, No. 10, pp. 1913-1918, 1996.
Ardissino, Diego et al., "Thrombogenic potential of human coronary atherosclerotic plaques", Blood, vol. 98, No. pp. 2726-2729, 2001.
Presta, Leonard et al., "Generation of a humanized, high affinity anti-tisse factor antibody for use as novel antithrombotic therapeutic", Thromb Haemost; 85; pp. 379-389, 2001.
Carson, Steven et al., An Inhibitory Monoclonal Antibody Against Human Tissue Factor:, Blood, vol. 70. No. 2, pp. 490-493, 1987.
Paborsky, Lisa et al., Mammalian cell transient expression of tissue factor for the production of antigen, Protein Engineering, vol. 3, No. 6, pp. 547-553, 1990.
Tanaka, H. et al., Purification of Glycosylated Apoprotein of Tissue Factor Brain and Inhibition of its Procoagulant Activity by a Specific Antibody, Thrombosis Research, vol. 40, pp. 745-756, 1985.
Kirchhofer, Daniel et al., "Epitope Location on Tissue Factor Determines the Anticoagulant Potency of Monoclonal anti-tissue Factor Antibodies", Thromb. Haemost, vol. 84, pp. 1072-1081, 2000.
Huang, Mingdong et al., "The Mechanism of an inhibitory Antibody on TF-initiated Blood Coagulation Revealed by the Crystal Structures of Human Tissue Factor, Fab 5G9 and TF 5G9 Complex", Journal of Molecular Biology, vol. 275, pp. 873-894, 1998.
Chen, Jiang et al. Tissue Factor—A Receptor Involved in the Control of Cellular Properties, Including Angiogenesis Thromb Haemost, vol. 86, pp. 334-345, 2001.
Rao, Chilukuri N. et al., "Expression of Tissue Factor Pathway Inhibitor 2 Inversely Correlates During the Progression of Human Gilomas" Clinical Cancer Research, vol. 7, pp. 570-576, 2001.
Mechtcheriakova, Diana et al., "Specificity, diversity, and convergence in VEGF and TNG—signaling events leading to tissue factor up-regulation via EGR-1 in endothelial cells", FASEB J. vol. 15, pp. 230-242, 2001.
Shen, Ben Quan et al., "Vascular Endothelial Growth Factor KDR Receptor Signaling Potentiates Tumor Necrosis Factor-induced Tissue Factor Expression in Endothelial Cells", The Journal of Biological Chemistry, vol. 276, No. 7, pp. 5281-5286, 2001.
Hu et al, "Targeting tissue factor on tumor vascular endothelial cells and tumor cells for immunotherapy in mouse models of prostatic cancer", Proc. National Acad. Sci , Department of Molecular Biophysics and Biochemistry, Yale University, vol. 98, No. 21, pp. 12180-12185, 2001.
Nilsson et al., "Targeted Delivery of Tissue Factor to the ED-B Domain of Fibronectin, a Marker of Angiogenesis, Mediates the Infarction of Solid Tumors in Mice", Cancer Research, vol. 61, pp. 711-716, 2001.
Hu et al, "Targeting tumor vascular endothelial cells and tumor cells for immunotherapy of human melanoma in a mouse xenograft model:, Proc. National Acad. Sci., vol. 96, pp. 8161-8166,", Department of Molecular Biophysics and Biochemistry, Yale University 1999.
Ran et al., "Infarction of solid Hodgkin's tumors in mice by antibody-directed targeting of tissue factor to tumor vasculature", Cancer Research, vol. 58, No. 20, pp. 4646-4653, 1998.
Huang et al., Tumor Infarction in Mice by Antibody-Directed Targeting of tissue Factor to Tumor Vasculature, Science, vol. 275, pp. 547-550, 1997.
Amirkhosravi et al., "Tissue Factor Pathway Inhibitor Reduces Experimental Lung Metastasis of B16Melano a", Throm Haemost, vol. 87, pp. 930-936, 2002.
Palumbo et al., "Fibrinogen is an important determinant of the metastatic potential of circulating tumor cells", Blood, vol. 96(10), pp. 3302-3309, 2000.
Hembrough et al, "Tissue Factor/Factor VIIa Inhibitors block angiogenesis and Tumor Growth Through a Nonhemostatic Mechanism", Cancer Research, vol. 63, pp. 2997-3000, 2003.
Bromberg et al., Tissue Factor promotes melanoma matastasis by a pathway independent of blood coagulation:, Proc. Natl. Acad. Sci, vol. 92, pp. 8205-8209, 1995.
Bazan, J. Fernando, "Structural design and molecular evolution of a cytokine receptor superfamily", Proc, Natl. Acad, Sci., USA, vol. 87, pp. 6934-6938, 1990.
Ruf et al., "Tissue Factor Signaling" Thrombosis and Haemostasis, The Scripps Research institute, USA, vol. 82 (2), pp. 175-182, 1999.
Versteeg et al., "The Pleiotripic Effects of Tissue Factor: A Possible Role for Factor VIIa-induced Intracellular Signalling", Thromb Haemos, vol. 86, pp. 1353-1359, Schattauer GmbH, Stuttgart, 2001.

(56) References Cited

OTHER PUBLICATIONS

Bach et al, "Mechanism of Tissue Factor Activation on HL-60 Cells", Blood, vol. 89, No. 9, pp. 3270-3276, 1997.

Refino et al., A Human Antibody that Binds to the γ-carboxyglutamic Acid Domain of Factor IX is a Potent Antithrombotic in Vivo:, Thromb. Haemost, vol. 82, pp. 1188-1195, 1999.

Ruf et al., "Redundant signaling of tissue factor and thrombin in cancer progression", Thromb Haemost, vol. 5, pp. 1584-1587, 2007.

Milsom et al.,"Tissue Factor and Cancer Stem Cells—Is There a Linkage", Arterioscler Thromb Vasc Biol. vol. 29, pp. 2005-2014, 2009.

Camrer et al., "Tissue Factor- and factor X-dependent activation of protease-activated receptor 2 by factor VIIa", Proc Natl. Acad. Sci. USA vol. 97, pp. 5255-5260, 2000.

Riewald & Ruf, "Mechanistic coupling of protease signaling and initiation fo coagulation by tissue factor" Proc Natl. Acad. Sci USA vol. 98, pp. 7742-7747, 2001.

Ruf et al., "Specificity of coagulation factor signaling", Thromb Haemost vol. 1, pp. 1495-1503, 2003.

Hjortor et al., "Tissue Factor-factor VIIa-specific up-regulation of IL-8 expression in MDA-MB-231 cells is mediated by PAR-2 and results in increased cell migration", Blood, vol. 103, pp. 3029-3037, 2004.

Rao & Pendurthi, "Tissue Factor-Factor VIIa Signaling", Arterioscler, Thromb Vasc. Biol. vol. 25, pp. 47-56, 2005.

Ahamed et al., "Disulfide isomerization switches tissue factor from coagulation to cell signaling", Proc Natl Acad Sci USA, vol. 103(38), pp. 13932-13937, 2006.

Magdolen et al., "Immunological and Functional Analyses of the Extracellular Domain of Human Tissue Factor", Biol Chem, vol. 379, pp. 157-165, 1996.

Versteeg et al., "Inhibition of Tissue Factor Signaling Suppresses Tumor Growth", Blood, vol. 111(1), pp. 190-199, 2008.

Fransson et al., "Human Framework Adaptation of a Mouse Anti-Human IL-13 Antibody", Journal of Molecular Biology, vol. 398, pp. 214-231, 2010.

Musolino et al., "Immunoglobulin G Fragment C Receptor Polymorphisms and Clinical Efficacy of Trastuzumab-Based Therapy in Patients With HER-2/neu-Positive Metastatic Breast Cancer", Journal of Clinical Oncol., vol. 26, pp. 1789-1796, 2008.

Bibeau et al., "Impact of FcyRIIa-FcyIIIa Polymorphisms and KRAS Mutations on the Clinical Outcome of Patients with Metastatic Colorectal Cancer Treated with Cetuximab Plus Irinotecan", Journal of Clinical Oncol., vol. 27, pp. 1122-1129, 2009.

Lefranc et al., "IMGT, the international ImMunoGeneTics database", Nucleic Acids Research, vol. 27, No. 1 pp. 209-212, Jan. 1, 1999.

Janssen Biotech, Inc, International Search Report for PCT/US2012/208770 filed Mar. 12, 2012 dated Aug. 27, 2012.

* cited by examiner

*Fig. 4*

```
                                1                                                 50
mu anti-TF 10H10 HCV    (1)  QVHLQQSGAELMKPGASVKISCKAS GYTFITYWIE WVKQRPGHGLEWIG D
       M59 - H22  HCV   (1)  EVQLVQSGAEVKKPGESLRISCKGS GYTFITYWIE WVRQMPGKGLEWMG D
      M1587 - H116 HCV  (1)  EVQLVQSGAEVKKPGESLRISCKGS GYTFIPYWIE WVRQMPGKGLEWMG D
      M1593 - H171 HCV  (1)  EVQLVQSGAEVKKPGESLRISCKGS GYTFAPYWIE WVRQMPGKGLEWMG D
         Contact Residues                              *  * ***

51                                                100
mu anti-TF 10H10 HCV   (51)  ILPGSGSTN YNENFKGKATFTADSSSNTAYMQLSSLTSEDSAVYYCAR SG
       M59 - H22  HCV  (51)  ILPGSGSTN YSPSFQGHVTISADKSISTAYLQWSSLKASDTAMYYCAR SG
      M1587 - H116 HCV (51)  ILPGSGFTT YSPSFQGHVTISADKSISTAYLQWSSLKASDTAMYYCAR SG
      M1593 - H171 HCV (51)  ILPGTGFTT YSPSFQGHVTISADKSISTAYLQWSSLKASDTAMYYCAR SG
         Contact Residues    *   *  *                                             *

101        120
mu anti-TF 10H10 HCV  (101)  YYGNSGFAY WGQGTLVTVSA
       M59 - H22  HCV (101)  YYGNSGFAY WGQGTLVTVSS
      M1587 - H116 HCV(101)  YYGNSGFAY WGQGTLVTVSS
      M1593 - H171 HCV(101)  YYGNSGFAY WGQGTLVTVSS
         Contact Residues    ****

1                                                 50
mu anti-TF 10H10 LCV    (1)  DIVMTQSPSSLTVTAGEKVTMSC KSSQSLLSSGNQKNYLT WYQQIPGQPP
      M1593 - L3  LCV   (1)  DIVMTQTPLSLPVTPGEPASISC KSSQSLLSSGNQKNYLT WYLQKPGQSP
         Contact Residues                            ****  *  *

51                                               100
mu anti-TF 10H10 LCV   (51)  KLLIY WASTRES GVPDRFTGSGSGTDFTLTINSVQAEDLAVYYC QNDYTY
      M1593 - L3  LCV  (51)  QLLIY WASTRES GVPDRFSGSGSGTDFTLKISRVEAEDVGVYYC QNDYTY
         Contact Residues          *                                        ****

101     113
mu anti-TF 10H10 LCV  (101)  PLT FGAGTKLELK
      M1593 - L3  LCV (101)  PLT FGQGTKLEIK
         Contact Residues     *
```

HUMAN TISSUE FACTOR ANTIBODY AND USES THEREOF

PRIOR APPLICATION

This application claims priority to U.S. Application No. 61/452,674, filed Mar. 15, 2011, which is entirely incorporated herein by reference.

BACKGROUND

1. Field of the Invention

The invention relates to human adapted antibodies which bind human tissue factor, an antigen present on extra vascular tissues including tumor cells, which antibodies do not inhibit tissue factor mediated blood coagulation. The invention also relates to methods of using the antibody to treat conditions such as cancer that are associated with the presence and receptor functions of human tissue factor.

2. Discussion of the Field

Tissue Factor (TF), also known as coagulation factor III (F3), tissue thromboplastin, or CD142 is a transmembrane glycoprotein having a 219 amino acid extracellular domain comprising two fibronectin type III domains and a short intracellular domain with one serine residue capable of being phosphorylated. TF is the cellular receptor for FVII/FVIIa.

TF exhibits a tissue-specific distribution with high levels in the normal brain, lung and placenta and low levels in the spleen, thymus, skeletal muscle and liver in the form of a cellular receptor. It is also found in cell-derived microparticles and as an alternatively spliced soluble form. In addition to the expression in normal tissue, TF has been reported to be over-expressed in most major tumor types and in many tumor-derived cell lines (Ruf W J Thromb Haemost. 5:1584-1587, 2007; Milsom et al., Arterioscler Thromb Vasc Biol. 29: 2005-2014, 2009).

Coagulation of serum proteins in response to injury is an important physiological response to injury. Exposure of the blood to proteins including collagen (intrinsic pathway) and tissue factor (extrinsic pathway) initiates changes to blood platelets and the plasma protein fibrinogen, a clotting factor. Following damage to a blood vessel, factor VII (FVII) leaves the circulation and comes into contact with tissue factor (TF) expressed on tissue-factor-bearing cells (stromal fibroblasts and leukocytes), forming an activated TF-FVIIa complex. TF-FVIIa activates factor IX (FIX) and factor X (FX). FVII can be allosterically activated by TF and activated by thrombin, FXIa, plasmin, FXII and FXa. TF-FVIIa forms a ternary complex with FXa.

Tissue factor (TF) expression by nonvascular cells plays an essential role in hemostasis by activating blood coagulation. TF is further associated with processes distinct from hemostasis and directly related to functions at the surface of cells on which it is expressed. TF-dependent assembly of coagulation proteases on vascular and nonvascular cells activates protease activated receptors (PARs) which are G-protein-coupled receptors. Thus, the TF:VIIa complex is capable of inducing cell signaling, through PARs, primarily PAR2 (Camerer et al., Proc. Natl. Acad. Sci. USA 97:5255-5260, 2000; Riewald & Ruf, Proc. Natl. Acad. Sci. USA 98:7742-7747, 2001; Ruf et al, J Thromb Haemost 1: 1495-4503, 2003; Chen et al., Thromb Haemost 86: 334-45, 2001) contributing to tumorigenesis, angiogenesis, tumor progression, and metastasis.

The ternary complex TF/FVIIa/FXa is formed directly by the TF:VIIa complex acting on FX or indirectly after TF:VIIa cleavage of FIX to FIXa which can cleave FX to FXa. The TF/FVIIa/FXa complex formation may result in signaling or activate other receptors such as PAR1-4. TF/FVIIa/FXa complex formation leads to the induction of Interleukin-8 (IL-8), which can stimulate tumor cell migration (Hjortor et al., Blood 103:3029-3037, 2004). Both PAR1 and PAR2 are involved in tumor metastasis (Shi et al., Mol Cancer Res. 2:395-402, 2004), however, the activated binary and ternary complexes, TF-VIIa and TF-VIIa-FXa, are activators of PAR2 which also leads to cell signaling (Rao & Pendurthi, Arterioscler. Thromb. Vasc. Biol. 25:47-56, 2005). Therefore, it was of interest to determine whether the oncogenic role of tissue factor could be separated from the procoagulant role, which had also long been suspected to be involved in tumor migration, extravasation, and metastatic mechanisms.

Monoclonal antibodies such as those described by Morrisey (1988, Thromb Res 52(3): 247-261; U.S. Pat. No. 5,223,427) and Magdolen (1996 Biol Chem 379: 157-165) to tissue factor have been used to explore functional and immunological aspects of the ligand binding sites. Monoclonal antibodies capable of binding tissue factor can be used to block thrombotic events by interfering with the ability of TF to form or maintain the TF-VIIa complex or by blocking the ability of the complex to activate FX. Antibodies that bind to tissue factor and do not block coagulation are also known. Factor VIIa initiated TF signaling blocking but not coagulation blocking antibodies such as the antibody 10H10 have also been described (Ahamed et al. 2006 Proc Natl Acad Sci USA 103 (38): 13932-13937) and such antibodies have provided the opportunity to study the role and utility of an agent with such activity in the treatment of solid tumors (Versteeg, et al 2008 Blood 111(1): 190-199). Ruf et al, in published application WO2007056352A3 discloses methods and compositions for inhibiting tissue factor signaling without interfering with hemostatis in a patient.

As cancer progression is a multifaceted process, a therapeutic candidate which is a TF binding antibody capable of blockade of oncogenic, metastatic, angiogenic, and anti-apoptotic functions on tumor cells while not interfering with hemostasis in a patient would be desirable.

SUMMARY OF THE INVENTION

The present invention provides a human adapted anti-human tissue factor specific antibody for use as a human therapeutic which retains the binding epitope of the murine antibody 10H10, which antibody does not compete with tissue factor for FVIIa binding and therefore does not substantially block the procoagulant, amidolytic activity of the TF-VIIa complex but which does block TF-VIIa mediated signaling and downstream oncogenic effects such as cytokine IL-8 release.

The human adapted antibody of the invention is constructed of human IgG variable domain frameworks in combination with CDR variant residues as determined by referring to the sequence of the 10H10 murine antibody CDR sequences and as represented as SEQ ID NO: 6-11 and 27. Human frameworks FR1 and FR2 and FR3, combined with the CDRs and CDR variants, with FR4, are provided which allow the assembly of antibody binding domains with the immunospecificity of the murine antibody 10H10. In one embodiment of the invention, the six CDR sequences represented by SEQ ID NO: 6-11 or as the group represented by SEQ ID NO: 6, 8-11, and 27 are combined with human germline FRs, defined as the non-CDR positions of a human IgG variable domain, selected so that the binding affinity of 10H10 for human TF is retained. In one aspect, the human HC variable region FRs are derived from an IGHV gene family 1, 3 or 5 member as represented by the IMGT database. In one aspect, the human LC variable region FRs are derived from a human IGKV gene family 2 or 4 member. In one embodiment, antibody Fv (HC variable region paired with a LC variable region) comprise an HC variable domain selected from SEQ ID NO: 12-21 and a LC variable domain selected from SEQ ID NO: 22-26.

In a particular embodiment, the human FRs forming an antibody Fv (HC variable region paired with a LC variable region) comprise IGHV5 and IGKV2 FRs. The antibody of the invention comprises an HC variable domain having the H-CDR3 of SEQ ID NO: 8; an H-CDR1 having a sequence selected from SEQ ID NO: 6, and 62-83; an H-CDR2 having a sequence selected from SEQ ID NO: 7, 27, and 84-107; and an HC FR4 region, optionally, selected from IGVJ4 (SEQ ID NO: 60) or a variant thereof. The antibodies of the invention further comprise those having an LC variable domain having an L-CDR1 having a sequence selected from SEQ ID NO: 9, 108-116; an L-CDR2 having a sequence selected from SEQ ID NO: 10 and 117-120; and an L-CDR3 having a sequence selected from SEQ ID NO: 11 and 121-128; and a LC FR4 region, optionally, selected from IGKJ2 (SEQ ID NO: 61) or a variant thereof. In a specific embodiment, the human framework sequences are derived from IGHV5_a and the created variable domain comprises a sequence selected from SEQ ID NO: 19, 129-155. In another embodiment, the human framework sequences are derived from IGKV2D40_O1 and the created variable domain comprises a sequence selected from SEQ ID NO: 23, 156-163.

The antibodies of the present invention can be represented in one form as antibodies having a binding domain derived from IGHV5_a frameworks, defined as non-CDR positions, an H-CDR3 having the sequence SGYYGNSGFAY (SEQ ID NO: 8), wherein the sequences at the H-CDR-1 positions is given by the formula:

H-CDR1   GYTFX$_1$X$_2$X$_3$WIE (I)   (SEQ ID NO: 83)

where X1 is selected is selected from A, D, G, I, L, N, P, R, S, T, V, and Y; X2 is selected from A, P, S, and T and X3 is selected from F, H, and Y; or the sequence may be GFTFITYWIA (SEQ ID NO: 81); and the sequence at the H-CDR2 position is given by the formula:

H-CDR2   DIX$_1$PGX$_2$GX$_3$TX$_4$ (II)   (SEQ ID NO: 107)

where X1 is selected from I and L, X2 is selected from S and T, X3 is selected from A, F, H, and w; and X4 is selected from D, H, I, L, and N; except in H189 where H-CDR2 is DILPASSSTN (SEQ ID NO: 105).

The antibodies of the invention are represented as antibodies having a binding domain derived from IGKV2D40_O1 frameworks, defined as non-CDR positions, and wherein the sequences at the L-CDR-1 and/or LCDR-2, and L-CDR3 have the sequences given by the formulas:

(SEQ ID NO: 116)
L-CDR1   KSSQSLLX$_1$X$_2$X$_3$ X$_4$Q X$_5$NYLT (III)

where X1 is selected from F, P, S, T, W, and Y; X2 is selected from F, S, T, R, and V; X3 is selected from A, G, P, S, W, Y, AND V; X4 is selected from G, N, and T; X5 is selected from K, R, and S;

L-CDR2   X$_1$ASTRX$_2$S (IV)   (SEQ ID NO: 120)

where X1 is selected from H and W; X2 is selected from D, E and S;

L-CDR3   QNDX$_1$X$_2$X$_3$PX$_4$T (V)   (SEQ ID NO: 128)

where X1 is selected from D, F, and L; X2 is selected from S, T, and Y; X3 is selected from W, and Y; X4 is selected from L, and M.

Thus, the antibody heavy chain and light chain CDR residues are substantially modified from the murine CDRs of 10H10. For instance, in accordance with the description set forth above, the antibody heavy chain can be only 70% (3/10 residues altered in CDR1), and 60% (4/10 residues altered in CDR2) similar to the murine CDRs of 10H10 (CDR 3 is unchanged). The light chain CDR residues are only 71% (5/17 changed)), (71%) (2/7 changed), or 55% (4/9 changed) similar to the murine CDRs of 10H10.

The invention further provides human adapted antibodies that compete for binding to human tissue factor and thus bind to substantially the same epitope on human TF-ECD as the murine 10H10 antibody. The invention further provides methods of using such antibodies to treat a human subject suffering from a condition in which TF-expression and local bioactivity resulting from the TF-expression is directly or indirectly related to the condition to be treated.

The invention further provides methods for preparing the antibodies as well as pharmaceutically acceptable preparations of the antibodies, a container comprising the preparation, and a kit comprising the container wherein the antibody of the invention is made available for the methods of use to treat a human subject.

DESCRIPTION OF THE DRAWINGS

FIG. 4 shows an alignment of the amino acid sequences of the heavy chain (upper alignment) and light chain (lower alignment) variable domains of the murine antibody 10H10 (SEQ ID NO: 4 and 5, respectively), the human framework adapted sequences of antibody M59 (SEQ ID NO: 19 and 23, respectively) and, two selected affinity matured variable domain sequences H116 (SEQ ID NO: 133) and H171 (SEQ ID NO: 139).

DESCRIPTION OF THE SEQUENCE LISTING

Figure 1:
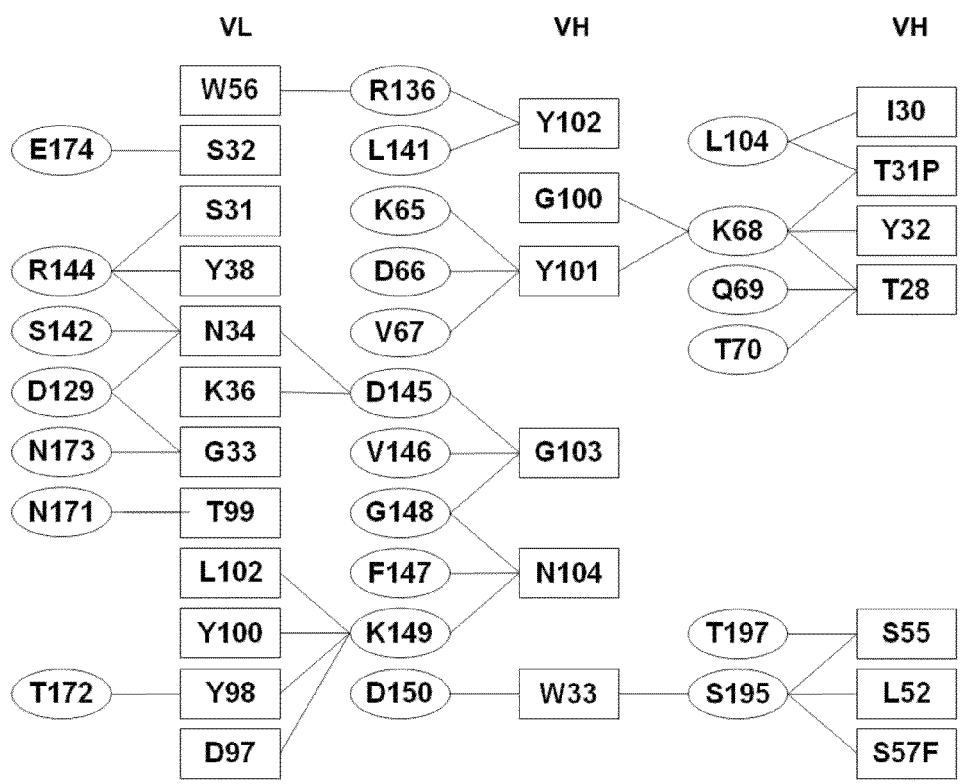
FIG. 1 shows the epitope revealed by X-ray diffraction analysis of a co-crystal of 10H10 Fab or with a human adapted variant (M1593 Fab) and human TF-ECD residues 5-208, where the two contact residues that were changed in M1593 H-CDR1 (T31P) and HCDR-2 (S57F) are shown.

| SEQ ID NO: | Description | Features or Origin |
|---|---|---|
| 1 | Human Tissue Factor Mature Chain | ECD = 1-219 |
| 2 | Cynomolgous Monkey Tissue Factor ECD | ECD only 1-220 |
| 3 | *Mus musculus* Tissue Factor (P20352) | ECD = 1-221 |
| 4 | 10H10 Heavy Chain (HC) Variable Region | |
| 5 | 10H10 Light Chain (LC) Variable Region | |
| 6 | H-CDR1 of 10H10 | |
| 7 | H-CDR2 of 10H10 | |
| 8 | H-CDR3 of 10H10 | |
| 9 | L-CDR1 of 10H10 | |
| 10 | L-CDR2 of 10H10 | |
| 11 | L-CDR3 of 10H10 | |
| 12 | H15 | IGHV5-a |
| 13 | H16 | IGHV1-46 |
| 14 | H17 | IGHV1-3 |
| 15 | H18 | IGHV3-74 |
| 16 | H19 | IGHV1-69 |
| 17 | H20 | IGHV1-18 |
| 18 | H21 | IGHV1-f |
| 19 | H22 | s1_IGHV5-a |
| 20 | H23 | s1_IGHV1-69 |
| 21 | H24 | s1_IGHV1-f |
| 22 | L2 | IGKV4-1_B3 |
| 23 | L3 | IGKV2D40_O1 |
| 24 | L4 | IGKV2D-28_A3 |
| 25 | L5 | IGKV2D-29_A2 |
| 26 | L7 | IGKV2-24_A23 |
| 27 | H-CDR2 of H22, H23, and H24 | Murine, Kabat-7 |
| 28 | FR1 of H15 and H22 | IGHV5-a |
| 29 | FR1 of H16, H17 and H20 | IGHV1-46, IGHV1-3, IGHV1-18 |
| 30 | FR1 of H18 | IGHV3-74 |
| 31 | FR1 of H19 and H23 | IGHV1-69 |
| 32 | FR1 of H21 and H24 | |
| 33 | FR2 of H15 and H22 | IGHV5-a |
| 34 | FR2 of H16, H19, H20, and H23_s1_IGHV1-69 | FR2 of IGHV1-46, IGHV1-69, IGHV1-18, and s1_IGHV1-69 |
| 35 | FR2 of H17 | IGHV1-3 |
| 36 | FR2 of H18 | IGHV3-74 |
| 37 | FR2 of H21 and H24 | IGHV1-f |
| 38 | FR3 of H15 | IGHV5-a |
| 39 | FR3 of H16 | IGHV1-46 |
| 40 | FR3 of H17 | IGHV1-3 |
| 41 | FR3 of H18 | IGHV3-74 |
| 42 | FR3 of H19 | IGHV1-69 |
| 43 | FR3 of H20 | IGHV1-18 |
| 44 | FR3 of H21 | IGHV1-f |
| 45 | FR3 of H22 | s1_IGHV5-a |
| 46 | FR3 of H23 | s1_IGHV1-69_ |
| 47 | FR3 of H24 | s1_IGHV1-f |
| 48 | FR1 of L2 | IGKV4-1_B3 |
| 49 | FR1 of L3 | IGKV2D40_O1 |
| 50 | FR1 of L4 | IGKV2D-28_A3 |
| 51 | FR1 of L5 | IGKV2D-29_A2 |
| 52 | FR1 of L7 | IGKV2-24_A23 |
| 53 | FR2 of L2 | IGKV4-1_B3 |
| 54 | FR2 of L3 & L4 | IGKV2D-28_A3 |
| 55 | FR2 of L5 | IGKV2D-29_A2 |
| 56 | FR2 of L7 | IGKV2-24_A23 |
| 57 | FR3 of L2 | IGKV4-1_B3 |
| 58 | FR3 of L3, L4, and L5 | IGKV2D40_O1, IGKV2D-28_A3, IGKV2D-29_A2 |
| 59 | FR3 of L7 | IGKV2-24_A23 |
| 60 | FR4 HC | IGHJ4 |
| 61 | FR4 LC | IGKJ2 |
| 62 | H-CDR1 of H106 in M1602 | |
| 63 | H-CDR1 of H116 in M1587 | |
| 64 | H-CDR1 of H117 in M1590 | |
| 65 | H-CDR1 of H122 in M1591 | |
| 66 | H-CDR1 of H133 in M1612 | |
| 67 | H-CDR1 of H134 in M1597 | |
| 68 | H-CDR1 of H136 in M1613, and H185 of M1596 | |
| 69 | H-CDR1 of H136 in M1613 | |
| 70 | H-CDR1 of H139 in M1585 | |
| 71 | H-CDR1 of H158 in M1594 | |
| 72 | H-CDR1 of H160 in M1595 | M1595 |
| 73 | H-CDR1 of H164 in M1586 | |
| 74 | H-CDR1 of H165 in M1592 | |
| 75 | H-CDR1 of H168 in M1605 | |
| 76 | H-CDR1 of H171 in M1593 | |
| 77 | H-CDR1 of H173 in M1584 | |
| 78 | H-CDR1 of H179 in M1588 | |
| 79 | H-CDR1 of H181 in M1606 | |
| 80 | H-CDR1 of H187 in M1589 | |
| 81 | H-CDR1 of H189 in M1607 | |
| 82 | H-CDR1 of H177, H130, H105, and H128 | |
| 83 | H-CDR1 variants | |
| 84 | H-CDR2 of H106 in M1602 | |
| 85 | H-CDR2 of H115 in M1610 | |
| 86 | H-CDR2 of H116 in M1587 | |
| 87 | H-CDR2 of H117 in M1590 | |
| 88 | H-CDR2 of H128 in M1611 | |
| 89 | H-CDR2 of H130 in M1599 | |
| 90 | H-CDR2 of H134 in M1597 | |
| 91 | H-CDR2 of H136 in M1613 | |
| 92 | H-CDR2 of H137 in M1598 | |
| 93 | H-CDR2 of H138 in M1604 | |
| 94 | H-CDR2 of H160 in M1595 | |
| 95 | H-CDR2 of H164 in M1586 | |
| 96 | H-CDR2 of H165 in M1592 | |
| 97 | H-CDR2 of H168 in M1605 | |
| 98 | H-CDR2 of H171 in M1593 | |
| 99 | H-CDR2 of H173 in M1584 | |
| 100 | H-CDR2 of H177 in M1583 | |
| 101 | H-CDR2 of H179 in M1588 | |
| 102 | H-CDR2 of H181 in M1606 | |
| 103 | H-CDR2 of H185 in M1596 | |
| 104 | H-CDR2 of H187 in M1589 | |
| 105 | H-CDR2 of H189 in M1607 | |
| 106 | H-CDR2 of H207 in M1608 | |
| 107 | H-CDR2 variants | |
| 108 | L-CDR1 of L138 in both M1646 & M1638 | |
| 109 | L-CDR1 of L162 in both M1651 & M1643 | |
| 110 | L-CDR1 of L225 in both M1652 & M1644 | |
| 111 | L-CDR1 of L283 in both M1653 & M1645 | |
| 112 | L-CDR1 of L320 in both M1647 & M1639 | |
| 113 | L-CDR1 of L327 in both M1648 & M1640 | |
| 114 | L-CDR1 of L335 in both M1649 & M1641 | |
| 115 | L-CDR1 of L369 in both M1650 & M1642 | |
| 116 | L-CDR1 variants | |
| 117 | L-CDR2 of L138 in both M1646 & M1638 | |
| 118 | L-CDR2 of L320 in both M1647 & M1639 | |

-continued

DESCRIPTION OF THE SEQUENCE LISTING

| SEQ ID NO: | Description | Features or Origin |
|---|---|---|
| 119 | L-CDR2 of L335 in both M1649 & M1641 | |
| 120 | L-CDR2 Variants | |
| 121 | L-CDR3 of L162 in both M1651 & M1643 | |
| 122 | L-CDR3 of L225 in both M1652 & M1644 | |
| 123 | L-CDR3 of L283 in both M1653 & M1645 | |
| 124 | L-CDR3 of L320 in both M1647 & M1639 | |
| 125 | L-CDR3 of L327 in both M1648 & M1640 | |
| 126 | L-CDR3 of L335 in both M1649 & M1641 | |
| 127 | L-CDR3 of L369 in both M1650 & M1642 | |
| 128 | L-CDR3 Variants | |
| 129 | H177 | |
| 130 | H173 | |
| 131 | H139 | |
| 132 | H164 | |
| 133 | H116 | |
| 134 | H179 | |
| 135 | H187 | |
| 136 | H117 | |
| 137 | H122 | |
| 138 | H165 | |
| 139 | H171 | |
| 140 | H158 | |
| 141 | H160 | |
| 142 | H185 | |
| 143 | H134 | |
| 144 | H137 | |
| 145 | H130 | |
| 146 | H105 | |
| 147 | H106 | |
| 148 | H138 | |
| 149 | H168 | |
| 150 | H181 | |
| 151 | H189 | |
| 152 | H207 | |
| 153 | H115 | |
| 154 | H128 | |
| 155 | H133 | |
| 156 | H136 | |
| 157 | L138 | |
| 158 | L320 | |
| 159 | L327 | |
| 160 | L335 | |
| 161 | L369 | |
| 162 | L162 | |
| 163 | L225 | |
| 164 | L283 | |
| 165 | M1593 full-length light chain | |
| 166 | M1593 full-length heavy chain | |
| 167 | M1593-DE full-length heavy chain | |

DETAILED DESCRIPTION OF THE INVENTION

Abbreviations

TF=Tissue Factor, huTF=Human Tissue Factor, muTF=Murine Tissue Factor, cynoTF=Cynomolgus Tissue Factor, TF-FVIIa=Tissue Factor-Factor VIIa complex, TF/FVIIa=Tissue Factor-Factor VIIa complex, HC=Heavy chain, LC=Light chain, v-region=variable region, VH=Heavy chain variable region, VL=Light chain variable region, CCD=Charge-coupled device, CDR=Complementarity determining region, CHES=2-(N-cyclohexylamino)-ethanesulfonic acid, EDTA=Ethylenediaminetetraacetic acid, ECD=Extracellular domain, HEPES=N-(2-hydroxyethyl)-piperazine-N'-2-ethanesulfonic acid, HEK=Human embryonic kidney cells, MES=2-(N-morpholino)ethanesulfonic acid, PAR=Protease activated receptor, PBMC=peripheral blood mononuclear cells, PBS=Phosphate buffered saline, PDB=Protein Data Bank, PEG=Polyethylene glycol, SDS PAGE=Sodium dodecyl sulfate polyacrylamide gel electrophoresis, SEC=Size exclusion chromatography, MAb=Monoclonal antibody, FR=Framework in antibody, HFA=Human Framework adaption.

Definitions & Explanation of Terminology

As used herein, an "antibody" includes whole antibodies and any antigen binding fragment or a single chain thereof. Thus, the antibody includes any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present invention. The term "antibody" is further intended to encompass antibodies, digestion fragments, specified portions and variants thereof, including antibody mimetics or comprising portions of antibodies that mimic the structure and/or function of an antibody or a specified fragment or portion thereof, including single chain and single domain antibodies and fragments thereof. Functional fragments include antigen-binding fragments to a preselected target. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426, and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Conversely, libraries of scFv constructs can be used to screen for antigen binding capability and then, using conventional techniques, spliced to other DNA encoding human germline gene sequences. One example of such a library is the "HuCAL: Human Combinatorial Antibody Library" (Knappik, A. et al. J Mol Biol (2000) 296(1):57-86).

The term "CDR" refers to the complementarity determining region or hypervariable region amino acid residues of an antibody that participate in or are responsible for antigen-binding. The hypervariable region or CDRs of the human IgG subtype of antibody comprise amino acid residues from residues 24-34 (L-CDR1), 50-56 (L-CDR2) and 89-97 (L-CDR3) in the light chain variable domain and 31-35 (H-CDR1), 50-65 (H-CDR2) and 95-102 (H-CDR3) in the heavy chain variable domain as described by Kabat et al. (1991 Sequences of Proteins of Immunological Interest, 5th Ed. Public Health Service, National Institutes of Health, Bethesda, Md.) and/or those residues from a hypervariable loop (i.e., residues 26-32 (L1), 50-52 (L2) and 91-96 (L3) in the light chain variable domain and 26-32 (H1), 52-56 (H2), and 95-101 (H3) in the heavy chain variable domain as described by (Chothia and Lesk, 1987 J. Mol. Biol. 196: 901-917). Chothia and Lesk refer to structurally conserved hypervariable loops as "canonical structures". Framework or FR1-4 residues are those variable domain residues other than and bracketing the hypervariable regions. The numbering system of Chothia and Lesk takes into account differences in the number of residues in a loop by showing the expansion at specified residues denoted by the small letter notations, e.g. 30a, 30b, 30c, etc. More recently, a universal numbering system has been developed and widely adopted, international ImMunoGeneTics information System® (IMGT) (LaFranc, et al. 2005. Nucl Acids Res. 33:D593-D597).

Herein, the CDRs are referred to in terms of both the amino acid sequence and the location within the light or heavy chain by sequential numbering. As the "location" of the CDRs within the structure of the immunoglobulin variable domain is conserved between species and present in structures called loops, by using numbering systems that align variable domain sequences according to structural features, CDR and framework residues and are readily identified. This information is used in grafting and replacement of CDR residues from immunoglobulins of one species into an acceptor framework from, typically, a human antibody.

The terms "Fc," "Fc-containing protein" or "Fc-containing molecule" as used herein refer to a monomeric, dimeric or heterodimeric protein having at least an immunoglobulin CH2 and CH3 domain. The CH2 and CH3 domains can form at least a part of the dimeric region of the protein/molecule (e.g., antibody).

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents.

As used herein, $K_D$ refers to the dissociation constant, specifically, the antibody $K_D$ for a predetermined antigen, and is a measure of affinity of the antibody for a specific target. High affinity antibodies have a $K_D$ of $10^{-8}$ M or less, more preferably $10^{-9}$ M or less and even more preferably $10^{-10}$ M or less, for a predetermined antigen. The reciprocal of $K_D$ is $K_A$, the association constant. The term "$k_{dis}$," or "$k_2$," or "$k_d$" as used herein, is intended to refer to the dissociation rate of a particular antibody-antigen interaction. The "$K_D$" is the ratio of the rate of dissociation ($k_2$), also called the "off-rate ($k_{off}$)" to the rate of association rate ($k_1$) or "on-rate ($k_{on}$)." Thus, $K_D$ equals $k_2/k_1$ or $k_{off}/k_{on}$ and is expressed as a molar concentration (M). It follows that the smaller the $K_D$, the stronger the binding. Thus, a $K_D$ of $10^{-6}$ M (or 1 microM) indicates weak binding compared to $10^{-9}$ M (or 1 nM).

The terms "monoclonal antibody" or "monoclonal antibody composition" as used herein refer to a preparation of antibody molecules of single molecular composition. A monoclonal antibody composition displays a single binding specificity and affinity for a particular epitope. The term also includes "recombinant antibody" and "recombinant monoclonal antibody" as all antibodies are prepared, expressed, created or isolated by recombinant means, such as (a) antibodies isolated from an animal or a hybridoma prepared by the fusion of antibody secreting animal cells and an fusion partner, (b) antibodies isolated from a host cell transformed to express the antibody, e.g., from a transfectoma, (c) antibodies isolated from a recombinant, combinatorial human or other species antibody library, and (d) antibodies prepared, expressed, created or isolated by any other means that involve splicing of immunoglobulin gene sequences to other DNA sequences. An "isolated antibody," as used herein, is intended to refer to an antibody which is substantially free of other antibodies having different antigenic specificities. An isolated antibody that specifically binds to an epitope, isoform or variant of human TF may, however, have cross-reactivity to other related antigens, e.g., from other species (e.g., TF species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding," "immunospecific binding" and "binds immunospecifically" refers to antibody binding to a predetermined antigen. Typically, the antibody binds with a dissociation constant ($K_D$) of $10^{-7}$ M or less, and binds to the predetermined antigen with a $K_D$ that is at least twofold less than its $K_D$ for binding to a non-specific antigen (e.g., BSA, casein, or any other specified polypeptide) other than the predetermined antigen. The phrases "an antibody recognizing an antigen" and "an antibody specific for an antigen" are used interchangeably herein with the term "an antibody which binds specifically to an antigen." As used herein "highly specific" binding means that the relative $K_D$ of the antibody for the specific target epitope is at least 10-fold less than the $K_D$ for binding that antibody to other ligands.

As used herein, "isotype" refers to the antibody class (e.g., IgM or IgG) that is encoded by heavy chain constant region genes. Some antibody classes further encompass subclasses which are also encoded by the heavy chain constant regions and further decorated by oligosaccharides at specific residues within the constant region domains (e.g. IgG1, IgG2, IgG3 and IgG4) which further impart biological functions to the antibody. For example, in human antibody isotypes IgG1, IgG3 and to a lesser extent, IgG2 display effector functions as do murine IgG2a antibodies.

By "effector" functions or "effector positive" is meant that the antibody comprises domains distinct from the antigen specific binding domains capable of interacting with receptors or other blood components such as complement, leading to, for example, the recruitment of macrophages and events leading to destruction of cells bound by the antigen binding domains of the antibody. Antibodies have several effector functions mediated by binding of effector molecules. For example, binding of the C1 component of complement to antibodies activates the complement system. Activation of complement is important in the opsonisation and lysis of cell pathogens. The activation of complement stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

The terms "tissue factor protein", "tissue factor" and "TF" are used to refer to a polypeptide having an amino acid sequence corresponding to a naturally occurring human tissue factor or a recombinant tissue factor as described below. Naturally occurring TF includes human species as well as other animal species such as rabbit, rat, porcine, non human primate, equine, murine, and ovine tissue factor (see, for example, Hartzell et al., (1989) Mol. Cell. Biol., 9:2567-2573; Andrews et al., (1991) Gene, 98:265-269; and Takayenik et al., (1991) Biochem. Biophys. Res. Comm., 181: 1145-1150). The amino acid sequence of human tissue factor is given by the UniProt record P13726 (SEQ ID NO: 1), cynomolgous monkey (SEQ ID NO: 2), and murine by UniProt P20352 (SEQ ID NO: 3). The amino acid sequence of the other mammalian tissue factor proteins are generally known or obtainable through conventional techniques.

The antibodies of the invention are useful for administering to a human subject or for contacting human tissue where it is desired to block the functions of human TF expressed on a cell, tissue, or organ resulting from TF signaling and wherein it is also desired to not substantially alter the procoagulant functions of TF resulting from the formation of a TF:FVIIa complex. Such uses can be found in the treatment of tumors, in particular, primary or secondary solid tumors of the breast, prostate, lung, pancreas, and ovary.

The invention also encompasses nucleic acids encoding the antibody sequences of the invention which can be combined with those sequences known in the art to be useful in the construction and manufacture through recombinant means or transfer of the information for expression of the antibodies in a milieu where it is desired that they be formed, such in culture, in situ, and in vivo. The means for the operation of such nucleic acids with the intent of producing an antibody of the invention are well known to those skilled in the art.

The invention further provides for preparations such as pharmaceutically acceptable or stable preparations for administration and storage of an antibody of the invention in isolated form.

1. Composition of the Antibody

Properties

The present invention is based on the unexpected discovery that a non-coagulation blocking murine antibody which binds to human TF, known as 10H10 (Edgington, et al. U.S. Pat. No. 5,223,427) is capable of abrogating the signaling of TF in certain cells (Ahmed, et al. 2006, cited above, WO2007/056352A2). Therefore, an antibody of the invention is one that which retains the binding epitope of the murine antibody 10H10, which antibody does not compete with tissue factor for FVIIa binding and does not substantially block the procoagulant, amidolytic activity of the TF-VIIa complex and which does block TF-VIIa mediated signaling and downstream oncogenic effects such as cytokine IL-8 release. The antibody of the invention is adapted to human germline IgG genes as represented in the IMGT database and retains binding to human TF while not interfering with the ability of TF to initiate coagulation in the presence of calcium in human plasma.

An antibody that retains the binding epitope of murine antibody 10H10 can be assessed generally by assessing the ability of the antibody bind to TF and to compete with 10H10 for binding to human TF while at the same time, when present in a sample comprising TF in the presence of human plasma, will not substantially prolong the time required for the TF initiated coagulation of the plasma as compared to a like sample of human plasma in the absence of the antibody. In another sense, the epitope of the antibody can be physically mapped using techniques known in the art, including but not limited to deletion mutagenesis, substitution mutagenesis, limited proteolysis of TF bound by the antibody followed by peptide fragment identification, and co-cystallization and X-ray diffraction methods to map proximity of atomic structures of the primary structures of TF and the antibody binding domains thereby defining a three-dimensional association between the antibody and human TF (FIG. 1).

Figure 2:
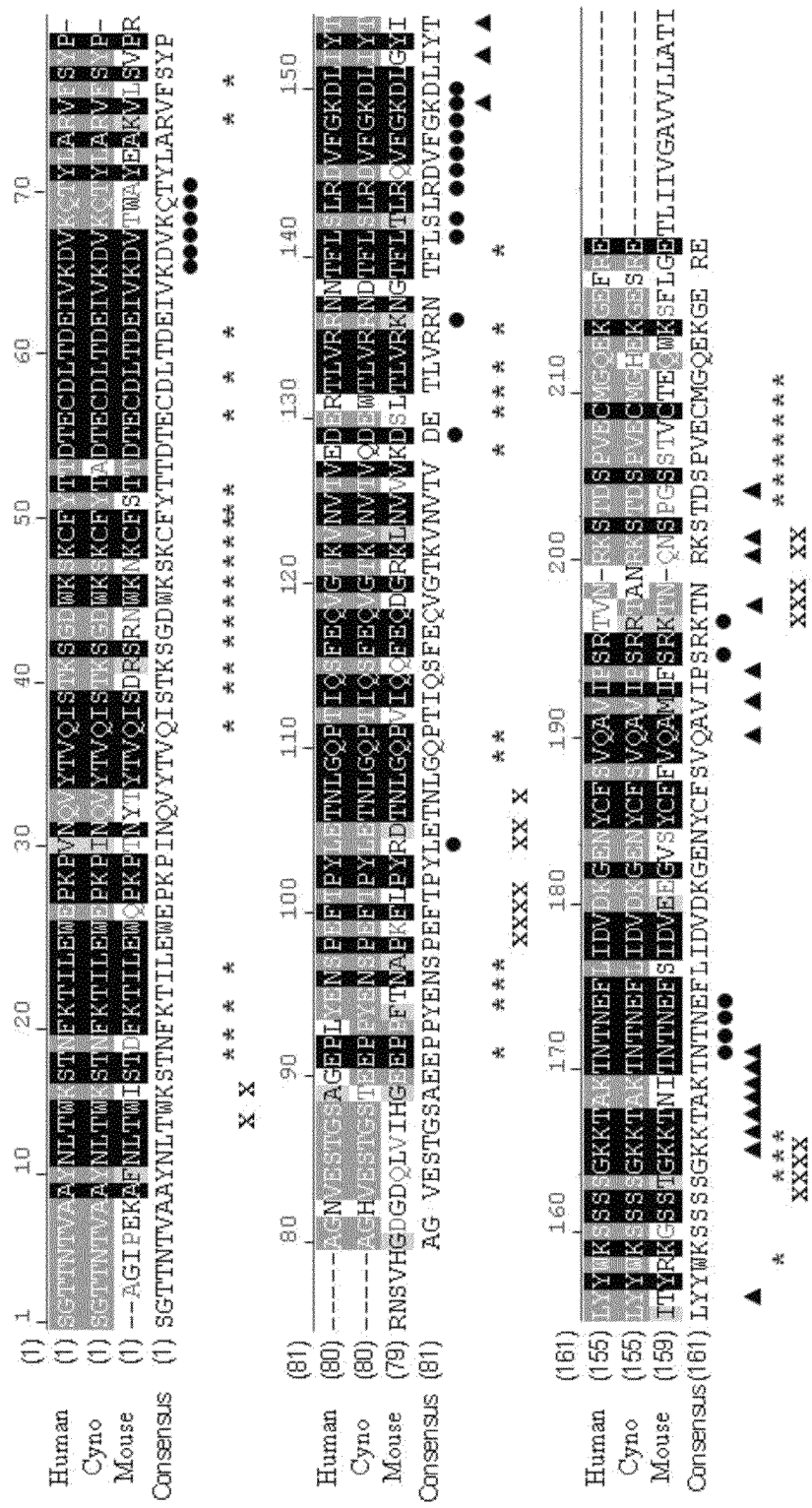
FIG. 2 is an alignment of the amino acid residues of human (SEQ ID NO: 1, 1-219), cyno (SEQ ID NO: 2, 1-220), and mouse TF-ECD (SEQ ID NO: 3, 1-221) showing residue positions contacted by the murine antibody TF8-5G9 (Huang et al. 1998 J Mol Biol 275:873-94) and 10H10 and those residues known to be in contact with the coagulation factors FVII/VIIa and FX.
Figure 3:
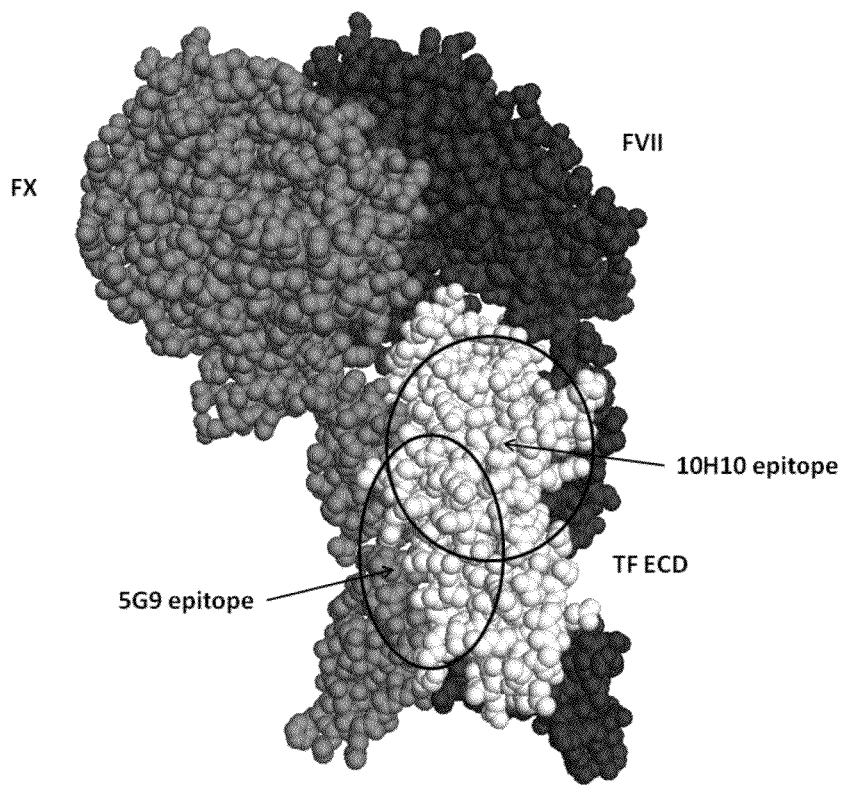
FIG. 3 shows the three dimensional projection of human TF-ECD with the areas indicated contacted by the paratopes of 5G9 and 10H10 as well as the coagulation factors FVII and FX, where only residues L104 and T197 are contacted by both 10H10 and FX.

The epitope, thus, can be defined as non-overlapping with the FVIIa binding site (FIGS. 2 and 3). More specifically, the epitope bound by the antibody of the invention may contact one or more residues in the N-domain of TF (residues 1-104 of the mature chain as represented by SEQ ID NO: 1) not contacted by FVII, such as residues 65-70, and not contact residues K165 and K166 in the C-domain, which are important for substrate binding (Kirchofer et al. 2000 Thromb Haemostat 84: 1072-81) while not interfering with the ability of TF to initiate coagulation in the presence of calcium in human plasma.

In one embodiment the on-rate ($k_a$ in 1/M·s) of the antibody is greater than $1 \times 10^{-5}$. In another embodiment, the off-rate ($k_d$ in 1/s) of the antibody for TF is less than $1.0 \times 10^{-5}$ and the resulting $K_D$ is less than $1 \times 10^{-9}$ M (less than 1 nM). In a particular embodiment, the antibody is a human germline gene adapted antibody with a $K_D$ less than $0.5 \times 10^{-9}$ M. In one embodiment the antibody has binding domains selected from those of the heavy and light chain pairings as shown in Table 11 such as M1639, M1645, M1647, M1652, M1641, M1644, M1587, M1604, M1593, M1606, M1584, M1611, M1596, M1601, M1588, M1594, M1607, M1612, M1595, M1599, M1589, M1592, M1583, and M1610.

The antibody composition may be further characterized as comprising a sequence of amino acid residues in the binding domain selected from one or more of the amino acid sequences given by SEQ ID NO: 6-166.

Antibody Variants with Altered Fc Functions

As the use of therapeutic monoclonal antibodies produced by recombinant methods expands, features and properties of these complex compositions are being explored. While the immunospecific and antigen targeting features generally reside in the variable domains and subdomains such as the loop ends of the hypervariable regions also known as the CDRs, the complex interacts with other receptors and serum components afforded by the structures formed by the constant domains, such as the Fc portion of an IgG.

Antibodies and other Fc-containing proteins can be compared for functionality by several well-known in vitro assays. In particular, affinity for members of the FcγRI, FcγRII, and FcγRIII family of Fcγ receptors is of interest. These measurements could be made using recombinant soluble forms of the receptors or cell-associated forms of the receptors. In addition, affinity for FcRn, the receptor responsible for the prolonged circulating half-life of IgGs, can be measured, for example, by BIAcore using recombinant soluble FcRn. Cell-based functional assays, such as ADCC assays and CDC assays, provide insights into the likely functional consequences of particular variant structures. In one embodiment, the ADCC assay is configured to have NK cells be the primary effector cell, thereby reflecting the functional effects on the FcγRIIIA receptor. Phagocytosis assays may also be used to compare immune effector functions of different variants, as can assays that measure cellular responses, such as superoxide or inflammatory mediator release. In vivo models can be used as well, as, for example, in the case of using variants of anti-CD3 antibodies to measure T cell activation in mice, an activity that is dependent on Fc domains engaging specific ligands, such as Fcγ receptors.

2. Generation of Tissue Factor Signal-Blocking Antibodies

An antibody having the features and biologic activity of an antibody described in this application can include or be derived from any mammal, such as, but not limited to, a human, a mouse, a rabbit, a rat, a rodent, a primate, a goat, or any combination thereof and includes isolated human, primate, rodent, mammalian, chimeric, human- or primate-adapted antibodies, immunoglobulins, cleavage products and other specified portions and variants thereof. Monoclonal antibodies may be prepared by any method known in the art such as the hybridoma technique (Kohler and Milstein, 1975, Nature, 256:495-497) and related methods using immortalized fusion partners fused to B-cells. Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15):7843-78481; WO92/02551; WO2004/051268 and International Patent Application number WO2004/106377.

The antibodies, including the target binding domains or subdomains, the constant domains, and the functional non-target binding domains such as the Fc-domain as described herein can be derived in several ways well known in the art. In one aspect, the sequences of naturally occurring antibody domains are conveniently obtained from published or on-line documents or databases, such as V-base (provided by the MRC Centre for Protein Engineering), the National Center for Biologics Information (NCBI Ig blast), or the ImMuno-GeneTics (IMGT) database provided by the International Immunogenetics Information System®.

Human Antibodies

The invention further provides human immunoglobulins (or antibodies) which bind human TF. These antibodies can also be characterized as engineered or adapted. The immunoglobulins have variable region(s) substantially from a human germline immunoglobulin and include directed variations in residues known to participate in antigen recognition, e.g. the CDRs of Kabat or the hypervariable loops as structurally defined. The constant region(s), if present, are also substantially from a human immunoglobulin. The human antibodies exhibit $K_D$ for TF of at least about $10^{-6}$ M (1 microM), about $10^{-7}$ M (100 nM), $10^{-9}$ M (1 nM), or less. To affect a change in affinity, e.g., improve affinity or reduce $K_D$, of the human antibody for TF, substitutions in either the CDR residues or other residues may be made.

The source for production of human antibody which binds to TF is preferably the sequences provide herein as the variable regions comprising a sequence selected from SEQ ID NO: 129-163, a FR selected from SEQ ID NO: 28-61, and CDRs, where the CDRs are selected from one or more of SEQ ID NO: 6-11, 27, 62-128 identified as capable of binding human TF and cross-reacting with cynomolgus monkey TF using a repertoire of human derived Fab displayed on filamentous phage particles.

The substitution of any of non-human CDRs into any human variable domain FR may not allow the same spatial orientation provided by the conformation to the parent variable FR from which the CDRs originated. The heavy and light chain variable framework regions to be paired in the final MAb can be derived from the same or different human antibody sequences. The human antibody sequences can be the sequences of naturally occurring human antibodies, be derived from human germline immunoglobulin sequences, or can be consensus sequences of several human antibody and/or germline sequences.

Suitable human antibody sequences are identified by computer comparisons of the amino acid sequences of the mouse variable regions with the sequences of known human antibodies. The comparison is performed separately for heavy and light chains but the principles are similar for each.

With regard to the empirical method, it has been found to be particularly convenient to create a library of variant sequences that can be screened for the desired activity, binding affinity or specificity. One format for creation of such a library of variants is a phage display vector. Alternatively, variants can be generated using other methods for variegation of a nucleic acid sequence encoding the targeted residues within the variable domain.

Another method of determining whether further substitutions are required, and the selection of amino acid residues for substitution, can be accomplished using computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. All nucleic acids encoding the antibodies described in this application are expressly included in the invention.

The variable segments of human antibodies produced as described herein are typically linked to at least a portion of a human immunoglobulin constant region. The antibody will contain both light chain and heavy chain constant regions. The heavy chain constant region usually includes CH1, hinge, CH2, CH3, and, sometimes, CH4 domains.

The human antibodies may comprise any type of constant domains from any class of antibody, including IgM, IgG, IgD, IgA and IgE, and any subclass (isotype), including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain may be of the $IgG_2$ class. The humanized antibody may comprise sequences from more than one class or isotype.

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides.

Such control sequences include a signal sequence, a promoter, an enhancer, and a transcription termination sequence (see Queen et al., Proc. Natl. Acad. Sci. USA 86, 10029 (1989); WO 90/07861; Co et al., J. Immunol. 148, 1149 (1992), which are incorporated herein by reference in their entirety for all purposes).

The antibodies or Fc or components and domains thereof may also be obtained from selecting from libraries of such domains or components, e.g., a phage library. A phage library can be created by inserting a library of random oligonucleotides or a library of polynucleotides containing sequences of interest, such as from the B-cells of an immunized animal or human (Hoogenboom, et al. 2000, Immunol. Today 21(8) 371-8). Antibody phage libraries contain heavy (H) and light (L) chain variable region pairs in one phage allowing the expression of single-chain Fv fragments or Fab fragments (Hoogenboom, et al. 2000 supra). The diversity of a phagemid library can be manipulated to increase and/or alter the immunospecificities of the monoclonal antibodies of the library to produce and subsequently identify additional, desirable, human monoclonal antibodies. For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in a complementarity determining region (CDR) of the variable region of the immunoglobulin polypeptide, and subsequently screened for desirable affinity and neutralization capabilities. Antibody libraries also can be created synthetically by selecting one or more human FR sequences and introducing collections of CDR cassettes derived from human antibody repertoires or through designed variation (Kretzschmar and von Ruden 2000, Current Opinion in Biotechnology, 13:598-602). The positions of diversity are not limited to CDRs, but can also include the FR segments of the variable regions or may include other than antibody variable regions, such as peptides.

Other libraries of target binding or non-target binding components which may include other than antibody variable regions are ribosome display, yeast display, and bacterial displays. Ribosome display is a method of translating mRNAs into their cognate proteins while keeping the protein attached to the RNA. The nucleic acid coding sequence is recovered by RT-PCR (Mattheakis, L. C. et al. 1994. Proc. Natl. Acad. Sci. USA 91, 9022). Yeast display is based on the construction of fusion proteins of the membrane-associated alpha-agglutinin yeast adhesion receptor, aga1 and aga2, a part of the mating type system (Broder, et al. 1997. Nature Biotechnology, 15:553-7). Bacterial display is based on fusion of the target to exported bacterial proteins that associate with the cell membrane or cell wall (Chen and Georgiou 2002. Biotechnol Bioeng, 79:496-503).

The invention also provides for nucleic acids encoding the compositions of the invention as isolated polynucleotides or as portions of expression vectors including vectors compatible with prokaryotic, eukaryotic or filamentous phage expression, secretion and/or display of the compositions or directed mutagens thereof.

3. Methods of Producing the Antibody of the Invention

Once an antibody molecule of the invention has been identified according to the structural and functional characteristics described herein, nucleic acid sequences encoding the desired portions of, or the entire antibody chains, can be cloned, copied, or chemically synthesized and can be isolated and used to express the antibody by routine methods. The antibody of the invention may be purified by any method known in the art for purification of an immunoglobulin molecule, for example, by chromatography (e.g., ion exchange, affinity, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Host Cell Selection or Host Cell Engineering

As described herein, the host cell chosen for expression of the recombinant Fc-containing protein or monoclonal antibody is an important contributor to the final composition, including, without limitation, the variation in composition of the oligosaccharide moieties decorating the protein in the immunoglobulin CH2 domain. Thus, one aspect of the invention involves the selection of appropriate host cells for use and/or development of a production cell expressing the desired therapeutic protein.

Further, the host cell may be of mammalian origin or may be selected from COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof.

Alternatively, the host cell may be selected from a species or organism incapable of glycosylating polypeptides, e.g. a prokaryotic cell or organism, such as and of the natural or engineered *E. coli* spp, *Klebsiella* spp., or *Pseudomonas* spp.

4. Methods of Using an Anti-TF Antibody

The compositions (antibody, antibody variants, or fragments) generated by any of the above described methods may be used to diagnose, treat, detect, or modulate human disease or specific pathologies in cells, tissues, organs, fluid, or, generally, a host. As taught herein, modification of the Fc portion of an antibody, Fc-fusion protein, or Fc fragment to provide a more specifically suited range of effector functions after target binding but where in the antibody retains the original targeting properties will generate variants of the antibody for specific applications and therapeutic indications.

The diseases or pathologies that may be amenable to treatment using a composition provided by the invention include, but are not limited to: cancer; including primary solid tumors and metastases; carcinomas, adenocarcinomas, melanomas, liquid tumors such as lymphomas, leukemias and myelomas and invasive masses formed as the cancer progresses; soft tissue cancers; sarcomas, osteosarcoma, thymoma, lymphosarcoma, fibrosarcoma, leiomyosarcoma, lipomas, glioblastoma, astrosarcoma, cancer of the prostate, breast, ovary, stomach, pancreas, larynx, esophagus, testes, liver, parotid, biliary tract, colon, rectum, cervix, uterus, endometrium, thyroid, lung, kidney, or bladder.

In so far as the antibody of the invention reduces the pro-oncogenic milieu in a tissue by blocking the ability of TF to participate in the downstream release of cytokines such as the inflammatory cytokine, IL-8, the antibody of the invention can be used prophylactically or in conjunction with other treatments directed to suppressing tumor proliferation and angiogenesis. Most age-related cancers derive from the epithelial cells of renewable tissues. An important element of epithelial tissues is the stroma, the sub-epithelial layer composed of extracellular matrix and several cell types including fibroblasts, macrophages, and endothelial cells. In cancerous tumors the stroma is critical for tumor growth and progression and TF can be expressed on stromal cells as well as the cancerous epithelial cells. Therefore, the presence of the downstream factors resulting from TF:VIIa signaling in stroma may create a pro-oncogenic tissue environment that synergizes with oncogenic mutations to drive the formation of neoplastic tissue.

Similarly, when TF is expressed in adipose tissue it can modify the function of the tissue in conditions such as obesity, metabolic syndrome, and diabetes. The antibody of the invention can be useful in treating these conditions by blocking TF:VIIa signaling. Some of the factors produced downstream of TF:FVIIa signaling, including IL-8 and IL-6, are powerful mediators of inflammation. Additional uses of the antibody of the invention therefore include treatment of inflammatory conditions such as, but not limited to, rheumatoid arthritis, inflammatory bowel disease, and asthma.

As the antibody of the invention inhibits TF:VIIa signaling and reduces downstream effects promoting angiogenesis, the antibodies of the invention can be useful in treating other diseases, disorders, and/or conditions, in addition to cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uveitis and Pterygia (abnormal blood vessel growth) of the eye; rheumatoid arthritis; psoriasis; delayed wound healing; endometriosis; vasculogenesis; granulations; hypertrophic scars (keloids); non-union fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

In so far as the antibody of the invention inhibits TF:VIIa signaling, the antibody can be used to treat and/or diagnose hyperproliferative diseases, disorders, and/or conditions, including but not limited to neoplasms. The antibody can inhibit proliferation of the disorder through direct or indirect interactions. Examples of hyperproliferative diseases, disorders, and/or conditions that can be treated, and/or diagnosed by the antibodies of the invention, include, hyperproliferative diseases, disorders, and/or conditions include, but are not limited to, hypergammaglobulinemia, lymphoproliferative diseases, disorders such as Castleman's disease, and/or conditions, paraproteinemias, purpura, sarcoidosis, Sezary Syndrome, Waldenstron's Macroglobulinemia, Gaucher's Disease, histiocytosis, and any other hyperproliferative disease in an organ, tissue or fluid body compartment.

Additional ways in which the antibodies of the present invention can be used therapeutically include, but are not limited to, directed cytotoxicity of the antibody, e.g., as mediated by complement (CDC) or by effector cells (ADCC), or indirect cytotoxicity of the antibody, e.g., as immunoconjugates.

While having described the invention in general terms, the embodiments of the invention will be further disclosed in the following examples that should not be construed as limiting the scope of the claims. In the experimental descriptions, certain reagents and procedures were used to produce proteins or an antibody or a specified fragment. Analytical methods routinely used to characterize the antibody are described below.

Materials and Methods

Protein and Antibody Standards

The recombinant extracellular domain (ECD) of human TF was constructed in two forms: for ELISA and Biacore-based direct binding assays, amino acid 1-219 of the mature chain of TF (SEQ ID NO: 1) was expressed in a mammalian system with a C-terminal His6-tag peptide; for co-crystallography studies, amino acid 5-213 of SEQ ID NO: 1 was expressed with a C-terminal His6-tag peptide in a bacterial system. Human$_{TF1-219}$ was biotinylated using NHS-ester chemistry targeting amine residues on the protein. For coagulation assays, Innovin® (Dade Behring Inc. cat#B4212), a lyophilized recombinant human tissue factor combined with phospholipids, calcium, buffers and stabilizers for diagnostic use was used.

Cynomolgous monkey (cyno) TF-ECD (SEQ ID NO: 2) was cloned using PCR from cDNA isolated form cynomolgous testes tissue obtained from BioChain Institute (Hayward, Calif.).

Several antibodies were used as reference antibodies: i) 10H10 cloned from the original hybridoma TF9.10H10-3.2.2 (U.S. Pat. No. 7,223,427) ii) a 10H10 mouse-human chimera, comprising SEQ ID NO: 4 and SEQ ID NO: 5 with human IgG1/Kappa constant regions, designated M1 iii) M59, a human FR adapted antibody comprising the six CDRs of 10H10 and serving as the parent antibody for affinity maturation, comprising SEQ ID NO:19 and SEQ ID NO:23 with human IgG1 and human Kappa constant region; iv) murine anti-human tissue factor antibody TF8-5G9 (U.S. Pat. No. 7,223,427); v) a humanized from of the antibody 5G9, known as CNTO 860, as a human IgG1/Kappa (U.S. Pat. No. 7,605,235); and vi) an isotype control (human IgG1/kappa) antibody binding to an irrelevant antigen (RSV) called B37.

Antibody Expression and Purification

Routine procedures were used to express and purify the disclosed antibodies. For primary screening, DNA encoding these molecules were transiently expressed in 96-well plates in HEK 293E cells and the supernatants were tested for activity (binding) 96 hours following transfection. Hits were identified and chosen for pilot-scale expression and purification. Pilot-scale expression was done transiently in HEK 293F cells or CHO—S at a volume of 750 ml. The harvested supernatants were purified via Protein A chromatography and the purified proteins were assessed for their affinity and functional activity. In addition, the purified proteins were subjected to biophysical characterization by SDS-PAGE, SE-HPLC, and cross-interaction chromatography (CIC). Theoretical isoelectric points (pI) were calculated for each variant as well. From the pilot scale characterizations, a set of final lead candidates was transfected in WAVE bioreactors and purified via Protein A chromatography.

Fab Production and Monoclonal Fab ELISA

Glycerol stocks from phage panning rounds were miniprepped and the pIX gene was excised by NheI/SpeI digestion. After religation, the DNA was transformed into TG-1 cells and grown on LB/Agar plates overnight. The next day, colonies were picked, grown overnight, and the cultures used for (i) colony PCR and sequencing of the V-regions, and (ii) induction of Fab production. For Fab production, the overnight culture was diluted 10-100 fold in new media and grown for 5-6 hours at 37 degrees C. Fab production was induced by the addition of fresh media containing IPTG and the cultures were grown overnight at 30 degrees C. The following day, the cultures were spun down and the supernatants, containing the soluble Fab proteins, were used for Fab ELISA.

For Fab ELISA, Fabs were captured onto plates by a polyclonal anti-Fd (CH1) antibody. After appropriate washing and blocking, biotinylated hTF was added at 0.2 nM concentration. This concentration enables ranking of the Fab variants, defined as percent binding of the parent, in which the parent Fab, present as a control in all plates, is defined as 100% binding. The biotinylated hTF was detected by HRP-conjugated streptavidin and chemiluminescence read in a plate reader.

TF-ECD Binding Mab-Based ELISA

A solution Phase direct TF binding ELISA using chemiluminescent detection was used to rank the top binders from human framework adaptation library. The 96 well black maxisorp plates were coated with 100 uL of 4 ug/ml Goat anti human IgG FC diluted in carbonate-bicarbonate buffer, pH 9.4 at 4° C. overnight and then washed thrice with wash buffer (PBS with 0.05% Tween-20 solution) and blocked with 300 μA 1% BSA/10 mM PBS solution for 1 hour followed by a washing as before. Samples or standards were diluted to 50 ng/ml in Assay Buffer (1% BSA in PBS+05% Tween) and 100 ul was added to the assay plate at room temperature for 1 hour with shaking. The plates were washed thrice and 100 ul per well of human or cynomologus TF-ECD with His Tag was added at 100 ng/ml diluted in Assay Buffer and incubate for 2 hours at room temperature. After washing, 100 ul per well of Qiagen peroxidase conjugated penta-his at 1:2000 dilution in assay buffer was added and incubated 1 hour at room temperature with shaking. The BM ChemiLum Substrate (BM Chemilum, POD, Roche) was made freshly at 1:100 dilution into Buffer and 100 ul added to the plates after a final wash. After 10 minutes the plates are read on Perkin Elmer Envision Reader, BM ChemiLum program.

MDA-MB-231 Whole Cell Binding of Anti-Tissue Factor mAbs by FACS

This assay is used to detect the direct binding of antibody to endogenouse human TF expressed in breast cancer cells. Prepare four point titrations of the test mAbs in FACS buffer (1% FBS in PBS) in duplicate. Start a titration at 1,000 ng/ml with 1:4 dilutions. M1, the parent molecule, is used as positive control while B37, anti-RSV mAb, is used as negative/isotype control. Unstained cells and secondary antibody, Cy-5 conjugated Goat anti-Human IgG Fc antibody in FACS buffer 1:200, is used as controls and prepared immediately before use.

Using standard tissue culture technique, rinse adherent MDA-MB-231 cells in culture flask with once with PBS (w/o Ca+2/Mg+2). Lift cells with Versene and count the cells and seed 200,000 cells per well in a polystyrene V-bottom plate. FACS Analysis Protocol: Tissue Factor Binding. Pellet the cells in a Allegra X-15R centrifuge at 450×g for 3 minutes at 4° C., resuspend in FACS Buffer (2% FBS in PBS) and plate 200,000 cells per well in 200 uL. Pellet cells at 450×g for 3 minutes at 4° C. Discard supernatants and add 100 uL/well test or control mAbs to designated wells and incubate on ice or at 4° C. for 1 hour (+/−10 minutes). Pellet cells at 450×g for 3 minutes at 4° C. Discard supernatants and wash cells once in FACS buffer. Resuspend cells in 200 uL/well FACS buffer and pellet cells at 450×g for 3 minutes at 4° C. Discard supernatants and add 100 uL/well secondary antibody to designated wells (triterate), and incubate on ice for 1 hour (+/−10 minutes). Pellet cells at 450×g for 3 minutes at 4° C. Discard supernatants and wash cells 2 times in FACS buffer before resuspending the cells in 200 uL/well FACS Buffer (triterate). Pellet cells at 450×g for 3 minutes at 4° C. Discard supernatant and resuspend cells in 100 uL/well CytoFix Buffer. Analyze reactions by flow cytometry (BD FACSArray). The FlowJo Software is used for FACS data analysis by gating the main population of cells in the unstained control well and applying the gate to the whole data set. The data is exported as a table of the geometric mean fluorescence intensity (MFI) in the red channel for the applied gate.

Thermafluor Assay

Thermofluor technology is a kinetic measurement of the unfolding of a molecule as it is heated. As the molecule is heated, a dye (ANS) is able to bind to the molecule as it unfolds. The dye will fluoresce as it binds to the molecule, and this fluorescence is measured over time. In this assay, the unfolding of the antibodies was measured from 37-95° C., and detected every 0.5° C. The Tms of the parent molecules in both murine and chimera form (10H10, M1, 5G9 and CNTO860) were also measured, along with 2 mAbs with known Tms to be used as assay controls (Emmp 4A5, and Emmp 5F6).

This assay was used to predict thermal stability of the human framework adaptation library variants. Dilute purified antibodies to 0.5 mg/mL in PBS and add 2 ul sample to each well to total 1 ug sample per well. Each sample is added in duplicate. Stock ANS is at 500 mM in DMSO. Dilute stock ANS 1:12 into DMSO (to 40 mM); Make Dye/Tween solution by combining 20 ul of the 40 mM ANS solution, 2.8 ul 10% Tween and 1.98 mL PBS; add 2uL Dye/Tween solution and 2 ul oil. Centrifuge plates (2 min at 450 rpm). Thermofluor Settings Shutter set to manual, Ramp Temperature 0.5 C/sec., Continuous Ramp, Temperature Ramp: 50-95° C. Select hold 15 s at high T., Exposure time 10 s/1 rep., Gain normal=2, Select "Single SC Image/plate".

Cross Interaction Chromatography (CID)

To determine the interaction of the various antibodies with other human antibodies, chromatography experiments were performed using a column coupled with human IgG (Sigma Aldrich). Briefly, 50 mgs of human IgG were coupled to a 1 ml NHS-Sepharose column (GE Healthcare) following the manufacturer's instructions. Uncoupled IgG was removed by washing with 0.1M Tris, pH8, 0.5M NaCl and unreacted NHS groups were blocked with the same buffer. The coupling efficiency was determined by measuring the protein concentration remaining in the unreacted coupling buffer and washes using Pierce's Coomassie Plus Assay Kit (Thermo Pierce) and subtracting from the amount of protein before immobilization. A control column was also prepared using the same protocol only no protein was added to the resin.

The control column was run first on a Dionex UltiMate 3000 HPLC after being equilibrated with PBS, pH7 at a flow rate of 0.1 ml/min. 20 1 of the stock protein solution was injected first to ensure non-specific binding sites were blocked followed by 20 1 of 10% acetone to check the integrity of the column.

Samples to be analyzed were diluted to 0.1 mg/ml in PBS, pH7. 20 microL of each sample was injected onto each column and allowed to run at 0.1 ml/min for 30 min. Retention times were recorded and the retention factor (k') was calculated for each variant.

The calculation of k' is the difference in the retention time on a protein derivatized column (IgG coupled column), $t_R$, and the retention time on a column with no protein coupled to it, $t_0$. The calculation also takes into account the retention time of acetone on both columns to standardize the column. Acceptable values for k' are less than 0.3.

Solubility

To determine the solubility of the various antibodies at room temperature, concentration experiments were performed using centrifugal filter devices. Briefly, antibody preparations in PBS were added to Vivaspin-15 (15 ml) centrifugal filter devices (30,000 MWCO, Sartorius, Goettingen, Germany) at room temperature. The filters were spun at 3000×g for 20 minute intervals in a Beckman Allegra X15-R centrifuge using a swinging bucket rotor. Once the volumes were reduced to about 2 ml, the supernatant was transferred to a Vivaspin-4 (4 ml) filter device (30,000 MWCO) and centrifuged at 4,000×g for 20 min intervals. Once the volume was reduced to 500 l, the sample was transferred to a Vivaspin-500 filter device and centrifuged at 15,000×g in an Eppendorf 5424 centrifuge for 15 minutes. This was repeated until the protein concentration reached 100 mg/ml or more. The protein concentration was determined by absorbance at 280 nm and 310 nm on a BioTek SynergyHT™ spectrophotometer with appropriate dilution. At this point, centrifugation was stopped and the sample kept at room temperature overnight to reach equilibrium. The next morning, the sample was checked for signs of precipitation. If the concentration was greater than 100 mg/ml, the process was stopped.

Factor VIIA-Induced IL-8 Inhibition Assay

This assay was used to test whether or not the TF-binding antibodies neutralize FVIIa-induced IL-8 release from human cells expressing TF. Human breast adenocarcinoma cells (MDA-MB-231) (ATCC: HTB-26), adapted to grow in DMEM and 10% FBS (Gibco: cat#11995 and cat#16140), were plated in 96-well cell culture plates (Nunc: cat#167008) at a density of 20000 cells per well (100,000 cells/mL) using standard cell culture techniques. The cells where allowed to recover for two days before antibody treatment starting at 2 ug/mL and undergoing either a 1:2 or 1:4 serial dilution in DMEM without FBS. The antibody was added one hour before treatment with human FVIIa (Innovative Research: cat#IHFVIIa, lot:2824) at a final concentration of 50 nM in DMEM without FBS. The cells were placed in the incubator for 24 hours. After treatment, the supernatant were collected and the quantity of IL-8 was detected by ELISA according to manufactures protocol (R&D Systems: cat#D8000C). Briefly, the optical density (OD) of each treatment sample was read at 450 nm and 540 nm. The reading at 540 nm was used to correct for optical imperfection in the assay plate while the corrected reading at 450 nm (OD 450 minus OD 540) was used to calculate the IL-8 content in the treatment samples using an IL-8 Standard Curve prepared according to manufactures protocol. Wells with cells not receiving antibody and FVIIa treatment were used to define the endogenous IL-8 level while wells with cells only receiving FVIIa was used to define the "no inhibition" IL-8 level, thereby defining the minimum and maximum IL-8 levels, respectively. The MAb titration treatment samples where normalized to the maximum and minimum IL-8 levels as defined above and expressed as percent inhibition. The normalized data were either represented in bar graphs or fitted to a four-parameter logistic curve fit to extract $EC_{50}$ values for each MAb.

Coagulation Assay

This assay was used to determine whether or not the anti-human TF antibodies block coagulation in vitro using human plasma in the presence of calcium and added recombinant human TF preparation (Innovin, Dade Behring Inc). Anti-human TF antibodies are diluted to 2 mg/ml antibody in HBSS (Gibco, cat#14175). Pooled human plasma with Na Citrate (George King Biomedical, Novi, Mich.) is spun down at 1000 rpm for 5 min and clear plasma is transferred to a new tube. In each well of a clear 96 well assay plate (NUNC, cat#439454), 25 ul of the diluted antibody is added to 100 ul of the human plasma. The reaction is initiated by adding 125 ul of Innovin (Dade Behring Inc., cat#B4212) diluted 1:500 into HBSS with 22 mM CaCl2 to each well containing plasma with or with antibody. The coagulation reaction is kinetically monitored at OD 405, immediately following reaction initiation and for 30 min at 37° C. using a SpectraMax M2e reader (Molecular Devices, Sunnyvale, Calif.). T½ Max is determined for each antibody using Softmax Pro Software as the time in seconds it takes to reach 50% of the maximum optical density. The time in seconds for samples was normalized to a reference on each plate, however, statistically there was no difference between samples listing 150 sec and 200 sec which was the average time for samples without antibody, for 10H10, and all of the 10H10 derived and human adapted variants.

EXAMPLE 1

Sequencing of 10H10

The murine antibody known as 10H10 generated at The Scripps Research Institute in La Jolla, Calif. (U.S. Pat. No. 5,223,427, Morrisey et al. 1988 Thromb Res. 52(3): 247-261) is produced by the hybridoma TF9.10H10-3.2.2. The sequences of the antibody from the 10H10 hybridoma clone, had not been previously reported.

The sequences were identified using the 5'RACE method (Focus 25 (2):25-27, 2003; Maruyama 1994 Gene 138, 171-174) where the two antibody chains, VH and VL, were amplified using 5' GeneRacer™ (InVitrogen), primer and 3' consensus primer complementary to a sequence within the mouse IgG1 constant region and mouse Kappa constant region, respectively. Nested PCR amplification using 5'GeneRacer Nested primer and a 3' consensus primer was used to generate VL products more suitable for sequence analyses.

At least 16 clones were selected to identify the variable region of each chain. Primers were used to sequence through the unknown region of the inserts. The raw sequence data was downloaded from the ABI DNA Sequencer to Vector NTI (Invitrogen Informax) for sequence analysis. One functional VH and one functional VL were identified. Both VH and VL genes were further analyzed to find their native signal sequences, FR, CDR, and J-segments.

The 10H10FRs and CDRs are numbered sequentially, and segmented following Kabat's definition (Kabat et al., 5th edit. Public Health Service, NIH, Washington, D.C., 1991), except in the region corresponding to the CDR-1 of VH. For this region a combination of Kabat and Chothia definition was used (Raghunathan, G., US2009/0118127 A1; Chothia and Lesk, J Mol Biol 196(4): 901-17, 1987).

TABLE 1

10H10 Sequence of the Variable Regions and its Sequence Structures

| Protein Name | Polypeptide Sequence | Subdomains |
|---|---|---|
| 10H10 Heavy Chain Variable Region (SEQ ID NO: 4) | QVHLQQSGAELMKPGASVKISCKAS GYTFITYWIE WVKQRPGHGLEWIG DILPGSGSTNYNENFKG KATFTADSSSNTAYMQLSSLTSEDSAV YYCAR | FR1 = 1 to 25 CDR1 = 26 to 35 (SEQ ID NO: 6) FR2 = 36 to 49 CDR2 = 50 to 66 (SEQ ID NO: 7) |

TABLE 1-continued

10H10 Sequence of the Variable Regions and its Sequence Structures

| Protein Name | Polypeptide Sequence | Subdomains |
|---|---|---|
| | SGYYGNSGFAY<br>WGQGTLVTVSA | FR3 = 67 to 98<br>CDR3 = 99 to 109<br>(SEQ ID NO: 8)<br>FR4 (JH3) = 110 to 120 |
| 10H10 Light Chain<br>Variable Region<br>(SEQ ID NO: 5) | DIVMTQSPSSLTVTAGEKVTMSC<br>KSSQSLLSSGNQKNYLT<br>WYQQIPGQPPKLLIY<br>WASTRES<br>GVPDRFTGSGSGTDFTLTINSVQAEDLA<br>VYYC<br>QNDYTYPLT<br>FGAGTKLELK | FR 1 = 1 to 23<br>CDR1 = 24 to 40<br>(SEQ ID NO: 9)<br>FR2 = 41 to 55<br>CDR2 = 56 to 62<br>(SEQ ID NO: 10)<br>FR3 = 63 to 94<br>CDR3 = 95 to 103<br>(SEQ ID NO: 11)<br>FR4 (K5) = 104 to 113 |

The cloned V regions were engineered with human IgG1/Kappa constant regions and cloned into mammalian expression vectors for recombinant expression in HEK293 or CHO cell lines creating a mouse-human chimeric antibody designated M1, which was used in assay development as a reference antibody. The HC V-region was also engineered with human IgG1 CH1 domain only and a C-terminal hexahistidine for the purposes of producing a 10H10Fab used in crystal structure analysis.

EXAMPLE 2

Epitope Mapping of a Non-Anticoagulant Tissue Factor Antibody

Epitope mapping for 10H10 was performed by crystal structure determination of a complex between human TF ECD and the corresponding Fab fragment. The His-tagged human TF ECD (residues 5-213 of SEQ ID NO: 1) was expressed in *Escherichia coli* and purified by affinity and ion exchange chromatography using a HisTrap HP column (GE Healthcare) and a Q HP column (GE Healthcare), respectively. The His-tagged chimeric versions (mouse V regions, human constant domains) of 10H10 Fab was expressed in HEK cells and purified using affinity (a TALON column, GE Healthcare) and size exclusion (a HiLoad Superdex 200 column, GE Healthcare) chromatography.

The complex was prepared by mixing the Fab with human TF ECD at the molar ratio 1:1.2 (excess TF). The mixture was incubated for 20 min at room temperature and loaded on a Superdex 200 column (GE Healthcare) equilibrated with 20 mM HEPES, pH 7.5, and 0.1 M NaCl. Fractions corresponding to the main peak were pooled, concentrated to 10 mg/mL, and used for crystallization. The complex was crystallized by the vapor-diffusion method at 20° C. The 10H10:TF complex was crystallized from solution containing 18% PEG 8000 in 0.1 M CHES, pH 9.5. For X-ray data collection, one crystal of the complex was soaked for a few seconds in the mother liquor supplemented with 20% glycerol, and flash frozen in the stream of nitrogen at 100 K. X-ray diffraction intensities were measured using a Rigaku MicroMa™-007HF microfocus X-ray generator equipped with a Saturn 944 CCD detector and an X-stream™ 2000 cryo-cooling system (Rigaku). The structure was determined by molecular replacement using the CCP4 suite of programs for macromolecular crystallography (Collaborative Computational Project, Number 4. 1994. Acta Cryst. D50, 760-763).

The TF ECD consists of two topologically identical domains with the immunoglobulin fold. The N-terminal domain spans residues 1-103, and the C-terminal domain spans residues 104-210 (of the ECD, SEQ ID NO: 1). The 10H10 epitope was found to be centered on residues K149-D150 of the ECD, which reaches a deep pocket between the variable domains of the heavy and light chains of 10H10. The interface between 10H10 and TF is extensive and involves all six CDR loops (FIG. 1).

Notable findings are that the TF epitope of 10H10 does not overlap with the FVII and FX binding sites (FIGS. 2 and 3). Also, the epitopes of 10H10 and 5G9 (another murine human-TF binding antibody with ability to block coagulation and which epitope was previously published, Huang et al. 1998 J Mol Biol 275:873-94) do partially overlap explaining the competitive binding between these two antibodies to human TF (FIGS. 2 and 3).

Human TF ECD:10H10 Interface

10H10 binds TF at the interface between the N- and C-terminal domains of the ECD. The convex surface of TF fits to the concave CDR surface of the antibody. The total area buried upon complex formation is over 1,100 Å2 on each of the interacting molecules. All six CDRs are involved in direct contacts with TF (contacts defined as a 4-Å interatomic distance). In total, there are 24 epitope residues and 25 paratope residues. CDRs L1, H1 and H3 form the majority of contacts. Residues forming the epitope and the paratope of the 10H10: TF complex are shown schematically in FIG. 1.

The 10H10 epitope includes two segments from the N-domain and three segments from the C-domain of TF ECD. The two segments from the N-domain interact with the antibody: residues 65-70 interacts with H-CDR1 and H-CDR3 and residue 104 interacting with H-CDR1. The three segments in the C-domain interact with the antibody: residues 195 and 197 interact with H-CDR1 and H-CDR2, residues 171-174 interact with L-CDR1 and L-CDR3, and residues 129-150 interact with L-CDR1, L-CDR3, H-CDR1 and H-CDR3; TF residues K149-D150 are in the center of the epitope; reaching a deep pocket formed between the VL and VH domains where their primary partners are D97 of the LC variable region (SEQ ID NO:5) and W33 of the HC variable region (SEQ ID NO: 4) of 10H10, respectively.

B. Antibody Specificity

The amino acid sequences of human, cynomolgus (cyno) monkey (SEQ ID NO: 2) and mouse TF ECD (SEQ ID NO: 3) are aligned in FIG. 2. There is high similarity between the sequences of human and cynomolgus TF ECD, and the two are only one residue different in the 10H10 contact residues: position 197 of SEQ ID NO:1, which is R (Arg) in the cyno sequence. As the T197 in the human sequence is contacted by a single H-CDR2 residue, the high level of cross-reactivity seen for the present set of 10H10 derived antibodies is explainable.

By aligning the human and mouse TF sequences, the epitope residues determining the species specificity of 10H10 were evident as significant amino acid differences occur in epitope residues: among the 24 residues 10H10 contacts in human TF, the human and mouse sequences differ at positions 68, 69, 70, and 104; in the N-domain and positions 136, 142, 145 and 197 in the C-domain of SEQ ID NO: 1 versus SEQ ID NO: 3. The differences are consistent with the diminished binding affinity of 10H10 for mouse TF.

FIG. 2 also indicates the interaction sites on human TF for FVII and FX based on a theoretical 3D model (FIG. 3) that describes their association into a ternary complex (Norledge et al., Proteins 53:640-648, 2003). Antibody 5G9 binds TF at an epitope that partially overlaps with the FX binding site. Therefore 5G9 competes with FX and this causes blockage of the coagulation cascade. 10H10 differs from 5G9 in that it does not block coagulation while it effectively shuts off the signaling via TF-associated PARs. Based on the model of the ternary TF/FVII/FX complex, it was expected that the 10H10 epitope would be on the free surface of TF and centered around residues K149-D150. Binding of 10H10 mapped by mutagenesis and peptide epitope mapping provided early evidence that this was the case.

The present crystal structure of the complex between TF ECD and 10H10 Fab provides a spatial mapping of the manner in which the antibody can bind TF without preventing FVII and FX interaction either with TF or each other. The 10H10 epitope as revealed by the structure covers the free surface of TF as it theoretically exists in the ternary complex. Further, the 10H10 epitope partially overlaps that of the coagulation blocking MAb, 5G9, epitope (Huang 1998 supra), the common residues being K149 and N171. Neither 10H10 or 5G9 block FVII binding to TF. The epitopes of 10H10 and FX are also non-overlapping, but a steric clash occurs between the constant domain of the Fab and the protease (globular) domain of FX in the current model. It should be noted however that the orientation of FX may in fact differ from the model and that the association between FX and TF may allow some flexibility in the protease domain. There is also a considerable flexibility in the elbow angle between the variable and constant domains of the Fab that may allow to avoid the clash upon 10H10 binding to the ternary complex.

EXAMPLE 3

Adapting the Binding Domains for Use in Humans

Efficacy of a therapeutic protein can be limited by unwanted immune reactions. Non-human monoclonal antibodies can have substantial stretches of linear amino acid sequences and local structural conformations that can elicit immune response in humans. The transfer of the residues responsible for immunospecifity of target binding of a non-human MAb to a human antibody scaffold more often than not results in a substantial loss of binding affinity for the target antigen. Hence, it is highly valuable to use sound design principles for creating antibody molecules that elicit minimal immunogenic reactions while retaining the binding and biophysical profiles of the parent non-human molecule when injected into humans.

As previously described in US20090118127A1 and exemplified in Fransson et al. 2010 J Mol Biol 398:214-231, a two-step process was used to both humanize and restore or enhance binding affinity to generate the antibody species of the present invention which exhibit the target effects of the murine antibody 10H10 when engaging human TF. The two-step process, called human framework adaption (HFA), consists of 1) human framework selection and 2) an affinity maturation step.

In the HFA process, the binding site residues (CDR) are combined with human germline genes selected based on sequence similarity and structural considerations. The two systems of CDR assignments for antibodies are: the Kabat definition which is based upon antibody sequence variability and the Chothia definition based on analyses of three-dimensional structures of antibodies. Among the six CDRs, one or the other system may be used where they diverge. In the case of the light chain CDRs, the Kabat definition is used.

In the case of heavy chain CDR3, both Kabat and Chothia's definition are identical. In the case of heavy chain CDR1, the Chothia definition was used to define the start and the Kabat definition as the end (pattern defined by W followed by a hydrophobic amino acid such as V, I or A). In the case of VH-CDR2, Kabat's definition was used. However, in most antibody structures, this sequence-based definition assigns a portion of FR3 as belonging to CDR2. Thus, a shorter version of this CDR, which ends seven (7) residues earlier on the C-terminal region of this CDR could also be used, called Kabat-7 herein.

Human FR Selection

Human FR's, defined as the regions in the V regions not comprised in the antigen-binding site, were selected from the repertoire of functional human germline IGHV and IGHJ genes. The repertoire of human germline gene sequences was obtained by searching the IMGT database (Lefranc 2005) and compiling all "01" alleles. From this compilation, redundant genes (100% identical at aminoacid level) and those with unpaired cysteine residues were removed from the compilation. The last update of the gene compilation was done on Oct. 1, 2007.

Initial selection of human sequences for HFA of VH was based on sequence similarity of the human VH germline genes to the entire length of the mouse VH region including FR-1 to 3 as well as H-CDR-1 and H-CDR-2. In the next stage, the selected human sequences were rank ordered using a score that takes into account both the length of the CDRs and sequence similarities between CDRs of mouse and human sequences. A standard mutation matrix, such as the BLOSUM 62 substitution matrix (Henikoff and Henikoff 1992 Proc Natl Acad Sci USA 15; 89(22):10915-9) was used for scoring alignments of the CDR's of mouse and human sequences and a large penalty was applied if there was an insertion and/or deletion in the CDR loops. Human FR-4 was selected based on sequence similarity of the IGHJ germline genes (Lefranc 2005) with mouse 10H10 sequence, IGHJ4 (SEQ ID NO: 60).

A similar procedure was used for selecting human FRs for VL. In this case IGVK, germline genes selected using the same procedure than that used for IGHV genes, served as genes for selecting FR's 1-3 and L-CDR 1-3. Human IGJ-K2 gene (SEQ ID NO: 61) was selected as FR4 for all variants.

Eleven VH and seven VL germline chains were selected. The VH genes selected were predominantly from IGVH-1 gene family: 6 sequences from IGVH1 with IGVH1-69 and IGVH1-f used with longer and shorter H-CDR2, 2 from IGVH3, and one IGVH5 gene used with both long and short H-CDR2. The VL genes represented six of the IGVK2 and one of the IGVK4 gene family.

Thus, VH variants H15, H19 and H21 having the longer H-CDR2 (SEQ ID NO: 7) correspond to H22, H23 and H24, respectively, where the shorter mouse CDR-H2 (SEQ ID NO: 27) was used. The prefix "s" denotes test variants with fewer mouse residues and more human residues in the beta strand region. The V-region designation used and the gene sequences used are shown in Tables 2 and 3 below.

TABLE 2

| Polypetide ID | IMGT Gene Used |
|---|---|
| H13 | VH-10H10 |
| H14 | IGHV1-2 |
| H15 | IGHV5-a |
| H16 | IGHV1-46 |
| H17 | IGHV1-3 |
| H18 | IGHV3-74 |
| H19 | IGHV1-69 |
| H20 | IGHV1-18 |
| H21 | IGHV1-f |
| H22 | s1_IGHV5-a |
| H23 | s1_IGHV1-69 |
| H24 | s1_IGHV1-f |

TABLE 3

| Peptide ID | IMGT Gene Name |
|---|---|
| L1 | VL-10H10 |
| L2 | IGKV4-1_B3 |
| L3 | IGKV2D40_O1 |
| L4 | IGKV2D-28_A3 |
| L5 | IGKV2D-29_A2 |
| L6 | IGKV2-30_A17 |
| L7 | IGKV2-24_A232 |
| L8 | IGKV2D-26_A21 |

A library of 96 Mabs, representing the 11 heavy chain and 7 light chain human FR variants plus the murine 10H10 chimeric chains was expressed in HEK 293E cells in a 96-well format to provide supernatants for the primary screen. For primary screening, using standard recombinant methods, DNA encoding the selected variable domains was recombined to form complete MAbs which were transiently expressed in 96-well plates in HEK 293E cells. Supernatant fluid from the cultures was tested for activity (binding) 96 hours following transfection.

Nineteen variants were chosen for pilot-scale expression in HEK 293-F cells and purification based on the results of the primary screen. Pilot-scale expression was done transiently in HEK 293F cells or CHO-S at a volume of 750 ml. The harvested supernatants were purified via Protein A chromatography and the purified proteins were assessed for their affinity and functional activity. In addition, the purified proteins were subjected to biophysical characterization by SDS-PAGE, SE-HPLC, and cross-interaction chromatography (CIC). Theoretical isoelectric points (pI) were calculated for each variant as well. From the pilot scale characterizations, a set of final lead candidates was transfected in WAVE bioreactors and purified via Protein A chromatography, Binding Assessment Binding of the parent chimeric antibody, M1, and HFA variants to both human and cyno TF was performed as a direct ELISA format using chemiluminescent detection. For primary screening of library variants in crude supernatants, samples or controls were normalized to 50 ng/ml in spent FreeStyle 293 HEK media (Gibco) and assayed at single concentration determinations. In the present assay, the concentration of antibody was 5 ng (0.1 ml used) and the TF ECD and the antigen was His6-TF-ECD$_{1-219}$ used at a final concentration of 10 ng/well.

The results of screening of the entire combinatorial library showed that, except H14, all other VHs bind to hTF with varying strengths. There are several HFA variants that gave a higher binding signal than the parent 10H10 (H13, L1), particularly some L3 and L5 combinations. H18 and H21 do not bind to human antigen as well as other VHs and showed insignificant binding to cyno antigen. Among the VLs, L6 and L8 did not bind either antigen while others bound at detectable levels. H14 and L8 also produced low expression when combined with any VL. There were 50 of the 77 antibody (VH, VL combinations) demonstrating TF binding as shown in Table 4.

TABLE 4

VH and VL Sequence IDs for the 50 Human TF Binding Human FR Variants

| Antibody ID | Light Chain Peptide ID | Light Chain SEQ ID NO: | Heavy Chain Peptide ID | Heavy Chain SEQ ID NO: |
|---|---|---|---|---|
| M1 | L1 | 5 | H13 | 4 |
| M9 | L2 | 22 | H15 | 12 |
| M10 | L3 | 23 | H15 | 12 |
| M11 | L4 | 24 | H15 | 12 |
| M12 | L5 | 25 | H15 | 12 |
| M14 | L7 | 26 | H15 | 12 |
| M16 | L2 | 22 | H16 | 13 |
| M17 | L3 | 23 | H16 | 13 |
| M18 | L4 | 24 | H16 | 13 |
| M19 | L5 | 25 | H16 | 13 |
| M21 | L7 | 26 | H16 | 13 |
| M23 | L2 | 22 | H17 | 14 |
| M24 | L3 | 23 | H17 | 14 |
| M25 | L4 | 24 | H17 | 14 |
| M26 | L5 | 25 | H17 | 14 |
| M28 | L7 | 26 | H17 | 14 |
| M30 | L2 | 22 | H18 | 15 |
| M31 | L3 | 23 | H18 | 15 |
| M32 | L4 | 24 | H18 | 15 |
| M33 | L5 | 25 | H18 | 15 |
| M35 | L7 | 26 | H18 | 15 |
| M37 | L2 | 22 | H19 | 16 |
| M38 | L3 | 23 | H19 | 16 |
| M39 | L4 | 24 | H19 | 16 |
| M40 | L5 | 25 | H19 | 16 |
| M42 | L7 | 26 | H19 | 16 |
| M44 | L2 | 22 | H20 | 17 |
| M45 | L3 | 23 | H20 | 17 |
| M46 | L4 | 24 | H20 | 17 |
| M47 | L5 | 25 | H20 | 17 |
| M49 | L7 | 26 | H20 | 17 |
| M51 | L2 | 22 | H21 | 18 |
| M52 | L3 | 23 | H21 | 18 |
| M53 | L4 | 24 | H21 | 18 |
| M54 | L5 | 25 | H21 | 18 |
| M56 | L7 | 26 | H21 | 18 |
| M58 | L2 | 22 | H22 | 19 |
| M59 | L3 | 23 | H22 | 19 |
| M60 | L4 | 24 | H22 | 19 |
| M61 | L5 | 25 | H22 | 19 |
| M63 | L7 | 26 | H22 | 19 |
| M65 | L2 | 22 | H23 | 20 |
| M66 | L3 | 23 | H23 | 20 |
| M67 | L4 | 24 | H23 | 20 |
| M68 | L5 | 25 | H23 | 20 |
| M70 | L7 | 26 | H23 | 20 |
| M72 | L2 | 22 | H24 | 21 |
| M73 | L3 | 23 | H24 | 21 |
| M74 | L4 | 24 | H24 | 21 |

TABLE 4-continued

VH and VL Sequence IDs for the 50 Human TF Binding Human FR Variants

| Antibody ID | Light Chain Peptide ID | Light Chain SEQ ID NO: | Heavy Chain Peptide ID | Heavy Chain SEQ ID NO: |
|---|---|---|---|---|
| M75 | L5 | 25 | H24 | 21 |
| M77 | L7 | 26 | H24 | 21 |

Based on relative binding affinity for TF using an ELISA, ten variants were selected for scale up of expression and purification. A summary of $K_D$s as measured by BIAcore, ELISA assay data, whole cell binding, inhibition of IL-8 induction from MDA-MB231 cells by 50 nM FVIIa by 2 ug/ml Mab, and Tms as measured by the Thermoflour assay are shown in Table 5.

TABLE 5

| MAb | VH | VL | Biacore $K_D$ (nM) Human | Biacore $K_D$ (nM) Cyno | Hu TF EC50 (ng/ml) | Cyno TF EC50 (ng/ml) | Whole Cell Binding, Ave % | IL-8 Induction, Ave % inhibition | Tm ° C. |
|---|---|---|---|---|---|---|---|---|---|
| M1 | H13 | L1 | 0.56 | 1.34 | 11.71 | 17.33 | 101% | 106% | 74.18 |
| M10 | H15 | L3 | 0.77 | 1.57 | 10.47 | 19.63 | 98% | 104% | 75.01 |
| M11 | H15 | L4 | 0.37 | 1.52 | 9.94 | 18.69 | 114% | 93% | 75.86 |
| M12 | H15 | L5 | 0.55 | 2.24 | 10.05 | 22.8 | 124% | 102% | 79.72 |
| M16 | H16 | L2 | 0.66 | 1.96 | 9.31 | 23.39 | 109% | 109% | 78.56 |
| M19 | H16 | L5 | 0.41 | 2.81 | 9.22 | 29.61 | 111% | 106% | 77.58 |
| M58 | H22 | L2 | 0.2 | 1.18 | 9.03 | 19.81 | 94% | 106% | 82.18 |
| M59 | H22 | L3 | 0.4 | 1.28 | 8.8 | 18.67 | 95% | 103% | 75.94 |
| M60 | H22 | L4 | 0.47 | 1.31 | 8.35 | 17.79 | 101% | 106% | 76.77 |
| M61 | H22 | L5 | 0.21 | 1.71 | 8.3 | 24.07 | 111% | 112% | 81.16 |
| M9 | H15 | L2 | 0.61 | 1.55 | 9.8 | 19.93 | 107% | 106% | 79.43 |

Several of the new human MAb variants exhibited higher affinity for TF than M1 (having the 10H10 variable chains: H13 and L1) and some were lower. The $K_D$ for M61 (0.21 nM) is 2.5 times lower than that of the murine parent MAb ($K_D$=0.56 nM). The data in Table 5 includes four Mabs comprising H15 and four with H22 both constructed from the same germline gene (IGHV5-a). Those with H22, and the shorter H-CDR2, generally exhibited higher binding affinity than the corresponding molecules with H15. While many of the new variants bound cyno TF, the ranking of cyno binding affinity differed from that for binding to human TF.

The mouse 10H10 MAb Tm was 74.2° C. The Tm of the selected molecules ranged of Tms from 75 to 82.2° C. Thus, the HFA process resulted in creation of antibody constructs with new Fd regions having increased binding affinity for human and nonhuman primate TF and also produced stable complete antibody variants with human domains.

Additional characterization of the new antibody constructs verified that the antibodies were capable of recognizing native TF on cells originating from human tumor tissue (MDA-MB231 breast cancer derived cells), and reduced TF signaling in the presence of VIIa as measured by the suppressed induction of IL-8 from MDA-MB231.

Additional biophysical characterization (solubility and cross-interaction chromatography) and assay results led to the selection of M59, comprised of the variable regions H22 and L3, for affinity maturation.

EXAMPLE 4

Antibody Maturation

The Fab libraries were constructed in a pIX phage display system as described in U.S. Pat. No. 6,472,147 (Scripps) and applicants co-pending application published as WO2009/085462 with minor modifications to restriction enzyme sites.

Based on the experimental structure of 10H10 in complex with hTF, two libraries were designed starting with the M59 pairing of H116 (SEQ ID NO: 19) and L3 (SEQ ID NO: 23) for diversification of both $V_L$ and $V_H$. The libraries differed in terms of the positions targeted for diversification, as well as in the amino acids used to diversify targeted positions. One library diversified a total of eight of the positions representing each CDR, previously shown to be in contact with TF. The emphasis in the design was put on L1, L3, H1 and H2. Positions in contact in L2 were not diversified nor most of the positions in H3. Labile or reactive amino acids such as Cys and Met were avoided.

A second set of libraries was designed to diversify amino acids at the periphery of the antigen-binding site determined by computing the solvent accessibilities of the bound and unbound Fab crystal structure. Residues buried upon binding but also in contact with solvent molecules were targeted for diversification. A total of 12 residues (6 in $V_L$ and 6 in $V_H$) were identified using this method, which were diversified with a reduced set of eight amino acids, including: Arg (R), Asn (N), Asp (D), Gly (G), His (H), Ser (S), Trp (W), and Tyr (Y). The size of the combined libraries was estimated to $8^{12}$ or $10^{10}$ variants, which can be covered using standard library restriction cloning techniques.

For the CDR contact residue library, the positions were diversified with 15 amino acids (all except Met, Cys, Lys, Gln, and Glu) using a nucleotide dimer (N-dimer) synthetic approach.

Fab libraries displayed on phage coat protein IX were panned against biotinylated hT-ECD according to panning schemes, known in the art, directed to increasing affinity by selecting for a slower off-rate (increase in off-rate value) or faster on-rate (decrease in on-rate value), or both were used. Panning used both human and cyno TF as target antigen. Phage was produced by helper phage infection. Binders were retrieved by addition of SA-beads to form a bead/antigen/phage complex. After the final wash, phage was rescued by infection of exponentially growing TG-1 *Escherichia coli* cells. Phage was again produced and subjected for additional rounds of panning.

The pIX gene was excised by NheI/SpeI digestion from the selected clones and, after religation, DNA was transformed into TG-1 cells and grown on LB/Agar plates overnight. The overnight cultures were used for (i) colony PCR and sequencing for the V-regions, and (ii) soluble Fab production. The soluble Fab proteins were captured onto plates by a polyclonal anti-Fd (CH1) antibody. After appropriate washing and blocking, biotinylated hTF was added at 0.2 nM concentration and biotinylated hTF was detected by HRP-conjugated streptavidin and chemiluminescence read as before. At this concentration of hTF, ranking of the Fab variants, defined as percent binding of the parent, in which the parent Fab, present as a control in all plates is defined as 100% binding, is possible.

By this criterion, 381 Fabs binding human TF at 100% or higher relative to M59 Fab were selected.

A analysis of the selected clones, indicated certain changes at Y2, I5, T6 and Y7 of heavy chain CDR1 (SEQ ID NO:6) corresponding to positions 27 and 30-32 of the V-region (SEQ ID NO:4 or 19) were successful. Although not a contact residue, position 27 only permitted an aromatic amino acid (Tyr and Phe). For positions 30-32, which have direct contact with K68, T101, Y103 and L104 of human TF SEQ ID NO: 1 in the 10H10 Fab (FIG. 1), position 30 was relatively permissive but 31 and 32 were restricted (Table 6).

In L-CDR2 changes in L3, S6 and S8 (SEQ ID NO: 7) corresponding to positions L52, S55 and S57 of SEQ ID NO: 4 or 19, which are residues that have direct contact with P194, S195, and T197 of human TF SEQ ID NO:1 in the 10H10 Fab (FIG. 1) there was a somewhat restricted set of substitutions permitted.

In H-CDR3, the N6 position (SEQ ID NO: 8) corresponding to N104 of SEQ ID NO: 4 or 19, which makes direct contact with F147, G148 and K149 of human TF-ED (SEQ ID NO:1) appeared to be restricted.

The allowed amino acid changes in each of the library positions selected by phage panning and screening for comparable binding affinity in solid phase capture assay using 0.2 nM human TF-ECD1-219 are shown in Table 6.

contact with K149, D150, N171 and T172 of human TF SEQ ID NO:1 (FIG. 1), position D97 (Kabat position 91) was restricted. The selection based on affinity binding to human TF-ECD1-219 clone permissive amino acid usage is summarized in Table 7.

TABLE 7

| | LC-CDR1 | | | | | LC-CDR2 | | LC-CDR3 | | |
|---|---|---|---|---|---|---|---|---|---|---|
| Contact with Antigen | Yes | Yes | Yes | Yes | Yes | Yes | No | Yes | Yes | Yes | Yes |
| Position in LC (SEQ ID NO: 23) | S31 | S32 | G33 | N34 | K36 | W56 | E61 | D97 | Y98 | T99 | Y100 |
| Sequence Diversity | A D F G H I L N P S T V W Y | A F G H I L N P R S T V W Y | A F G H I L N P R S T V W Y | A F G I L N P R S T V Y | A H I L N P R S V | A G W H N | A D E G H N P S T V Y | D | A F F G H I L N S T V Y | A D F G H L N R S T V Y | F H I L N W Y |

In summary, a series of affinity improved Fab variants were identified through construction of a phage library based on directed variegation of CDR positions of amino acid in the contact positions with antigen human TF for the variable

TABLE 6

| | HC_CDR1 | | | | | HC_CDR2 | | | | HC_CDR3 | |
|---|---|---|---|---|---|---|---|---|---|---|---|
| Contact with Antigen in | No | Yes | Yes | Yes | Yes | No | Yes | No | Yes | No | Yes | No |
| Position in HC (SEQ ID NO: 19) | Y27 | I30 | T31 | Y32 | L52 | G54 | S55 | G56 | S57 | N59 | N104 | S105 |
| Sequence Diversity | Y F G N A T R S L P Y A D H | I V A S | T P A F | Y H V | L I A V | G W | S T V P | G N S L R | S Y W F A H | N V T L I H W A D R F | N S | S A |

For VL in the selected clones, changes in S9, G10, N11 and K13 of L-CDR1 (SEQ ID NO: 9) corresponding to positions 32, 33, 34 and 36 of the LC variable region (SEQ ID NO: 5 or 23), which were shown by epitope mapping to contact E174, D129, 5142, R144 and D145 of human TF SEQ ID NO:1 (FIG. 1) are shown in Table 7 as relatively permissive. For L-CDR2, residue W1, position 56 in SEQ ID NO: 5 or 23 (Kabat residue number 50), is a contact residue while residue E61 showed limited tolerability for substitution. In the light chain CDR3 (SEQ ID NO: 9) corresponding to residue positions 97-100 of SEQ ID NO: 5 or 23, which have direct domains H22 (SEQ ID NO: 19) and L3 (SEQ ID NO: 23), followed by panning and selection of species with affinity in the screening assay of comparable or better binding at compared to the starting sequences.

Overall, modest increases in affinity for the VH and VL pairing selected from the designed HFA libraries were obtained. However, from the VH library where contact residues were variegated, the parent amino acid was re-selected after stringent phage panning. Only two paratope positions were significantly changed, as explained from structural analysis. These two amino acid replacements introduced in the CDRs during affinity maturation, T31P and S57F, involve contact residues. The 5-fold affinity improvement may be attributed to the increased interface of F57 which is in contact with S195 of TF. The VL interaction with TF seems to be plastic, allowing many changes to contact residues as well as neighboring residues.

Of the 381 VH and VL pairings, 43 were selected for further characterization. The selected 43 MAbs represented 27 different VHs and 8 VLs (see Table 8 for the pairing of the heavy chain and light chain sequences) and could be classified into three sub-groups: Group 1 variants have the same light chain (L3, SEQ ID NO: 23), and Group 2 and Group 3 are represented by eight light chains paired with two different heavy chains (H116 and H171, SEQ ID NO: 131 and 67, respectively).

TABLE 8

| MAb ID | LC ID | LC SEQ ID NO: | HC ID | HC SEQ ID NO: |
|---|---|---|---|---|
| M1583 | L3 | 23 | H177 | 129 |
| M1584 | L3 | 23 | H173 | 130 |
| M1585 | L3 | 23 | H139 | 131 |
| M1586 | L3 | 23 | H164 | 132 |
| M1587 | L3 | 23 | H116 | 133 |
| M1588 | L3 | 23 | H179 | 134 |
| M1589 | L3 | 23 | H187 | 135 |
| M1590 | L3 | 23 | H117 | 136 |
| M1591 | L3 | 23 | H122 | 137 |
| M1592 | L3 | 23 | H165 | 138 |
| M1593 | L3 | 23 | H171 | 139 |
| M1594 | L3 | 23 | H158 | 140 |
| M1595 | L3 | 23 | H160 | 141 |
| M1596 | L3 | 23 | H185 | 142 |
| M1597 | L3 | 23 | H134 | 143 |
| M1598 | L3 | 23 | H137 | 144 |
| M1599 | L3 | 23 | H130 | 145 |
| M1601 | L3 | 23 | H105 | 146 |
| M1602 | L3 | 23 | H106 | 147 |
| M1604 | L3 | 23 | H138 | 148 |
| M1605 | L3 | 23 | H168 | 149 |
| M1606 | L3 | 23 | H181 | 150 |
| M1607 | L3 | 23 | H189 | 151 |
| M1610 | L3 | 23 | H115 | 153 |
| M1611 | L3 | 23 | H128 | 154 |
| M1612 | L3 | 23 | H133 | 155 |
| M1613 | L3 | 23 | H136 | 156 |
| M1638 | L138 | 157 | H22 | 19 |
| M1639 | L320 | 158 | H22 | 19 |
| M1640 | L327 | 159 | H22 | 19 |
| M1641 | L335 | 160 | H22 | 19 |
| M1642 | L369 | 161 | H22 | 19 |
| M1643 | L162 | 162 | H22 | 19 |
| M1644 | L225 | 163 | H22 | 19 |
| M1645 | L283 | 164 | H22 | 19 |
| M1646 | L138 | 157 | H171 | 139 |
| M1647 | L320 | 158 | H171 | 139 |
| M1648 | L327 | 159 | H171 | 139 |
| M1649 | L335 | 160 | H171 | 139 |
| M1650 | L369 | 161 | H171 | 139 |
| M1651 | L162 | 162 | H171 | 139 |
| M1652 | L225 | 163 | H171 | 139 |
| M1653 | L283 | 164 | H171 | 139 |

Of the group of 27 antibodies having the same light chain as M59 (L3, SEQ ID NO: 23), the 27 heavy chains differ at three positions in H-CDR1 (GYTFX$_1$X$_2$X$_3$WIE (SEQ ID NO: 83) where X1 is selected from A, D, G, I, L, N, P, R, S, T, V, Y and X2 is selected from A, P, S, and T and X3 is selected from F, H, and Y); except in H189 where H-CDR1 is GFT-FITYWIA (SEQ ID NO: 81), and at four positions in H-CDR2 (DIX$_1$PGX$_2$GX$_3$TX$_4$ (SEQ ID NO: 107) where X1 is selected from I and L, X2 is selected from S and T, X3 selected from A, F, H, and w; and X4 is selected from D, H, I, L, and N; except in H189 where H-CDR2 is DILPASSSTN (SEQ ID NO: 105)) while the H-CDR3 and FRs were unaltered from the H22 sequence (SEQ ID NO: 19) and is SGYYGNSGFAY (SEQ ID NO: 8). The unique compositions of the heavy chains for these 27 Mabs are given below (Table 9).

TABLE 9

| MAb | LC SEQ ID NO: ID | HC SEQ ID NO: CDR 1 | H-CDR1 | HC-CDR 2 | SEQ ID NO: for H-CDR1 | SEQ ID NO: for H-CDR2 |
|---|---|---|---|---|---|---|
| M1583 | 23 | H177 | 129 GYTFGPYWIE | 82 | DIIPGSGWTN | 100 |
| M1584 | 23 | H173 | 130 GYTFVTYWIE | 77 | DILPGTGYTV | 99 |
| M1585 | 23 | H139 | 131 GYTFSPFWIE | 70 | DIIPGTGYTN | 93 |
| M1586 | 23 | H164 | 132 GYTFPTYWIE | 73 | DIIPGTGWTN | 95 |
| M1587 | 23 | H116 | 133 GYTFIPYWIE | 63 | DILPGSGFTT | 86 |
| M1588 | 23 | H179 | 134 GYTFGPFWIE | 78 | DILPGSGYTN | 101 |
| M1589 | 23 | H187 | 135 GYTFGPHWIE | 80 | DILPGTGYTN | 104 |
| M1590 | 23 | H117 | 136 GYTFLPYWIE | 64 | DIIPGTGFTN | 88 |
| M1591 | 23 | H122 | 137 GYTFRPYWIE | 65 | DIIPGTGYTN | 93 |
| M1592 | 23 | H165 | 138 GYTFSPHWIE | 74 | DILPGSGYTI | 96 |
| M1593 | 23 | H171 | 139 GYTFAPYWIE | 67 | DILPGTGFTT | 98 |
| M1594 | 23 | H158 | 140 GYTFPPYWIE | 72 | DILPGTGYTV | 99 |
| M1595 | 23 | H160 | 141 GYTFYPYWIE | 72 | DILPGTGFTN | 94 |
| M1596 | 23 | H185 | 142 GYTFTPYWIE | 68 | DILPGSGHTT | 103 |
| M1597 | 23 | H134 | 143 GYTFSSYWIE | 70 | DILPGTGATH | 90 |
| M1598 | 23 | H137 | 144 GYTFTPYWIE | 68 | DILPGTGYTV | 99 |
| M1599 | 23 | H130 | 145 GYTFGPYWIE | 82 | DILPGTGYTL | 89 |
| M1601 | 23 | H105 | 146 GYTFGPYWIE | 82 | DILPGTGYTV | 99 |
| M1602 | 23 | H106 | 147 GYTFDAHWIE | 62 | DILPGSGFTD | 84 |
| M1604 | 23 | H138 | 148 GYTFAPYWIE | 76 | DILPGTGYTW | 92 |
| M1605 | 23 | H168 | 149 GYTFGTYWIE | 75 | DILPGTGHTT | 97 |
| M1606 | 23 | H181 | 150 GYTFIPHWIE | 79 | DILPGSGWTN | 102 |
| M1607 | 23 | H189 | 151 GFTFITYWIA | 81 | DILPASSSTN | 105 |
| M1610 | 23 | H115 | 153 GYTFAPYWIE | 76 | DIIPGTGYTT | 85 |
| M1611 | 23 | H128 | 154 GYTFGPYWIE | 82 | DILPGSGYTT | 88 |
| M1612 | 23 | H133 | 155 GYTFNPYWIE | 66 | DILPGTGYTN | 104 |
| M1613 | 23 | H136 | 156 GYTFSSHWIE | 69 | DILPGSGFTH | 91 |

H171 (SEQ ID NO: 139) comprises an additional change in H-CDR1 and H-CDR2 as compared to H116, which are I31A and S55T.

Two groups of Mabs are represented by eight LC (Table 10) paired with one of two different HC: H22 (SEQ ID NO: 19) or heavy chain H171 (SEQ ID NO: 139). The eight light chains all have the FR of L3 (derived from IGKV240_O1) and have sequence changes in five positions in L-CDR1 (KSSQSLLX$_1$X$_2$X$_3$X$_4$QX$_5$NYLT (SEQ ID NO: 116) where X1 is selected from F, P, S, T, W, and Y; X2 is selected from F, S, T, R, and V; X3 is selected from A, G, P, S, W, Y, AND V; X4 is selected from G, N, and T; X5 is selected from K, R, and S), two in L-CDR 2 ($X_1$ASTR$X_2$S (SEQ ID NO: 120) where X1 is selected from H and W; X2 is selected from D, E and S) and four in L-CDR3 (QND$X_1X_2X_3$P$X_4$T (SEQ ID NO: 128) where X1 is selected from D, F, and L; X2 is selected from S, T, and Y; where X3 is selected from W, and Y; X4 is selected from L, and M). The compositions of the eight LC are shown in Table 10.

TABLE 10

| LC ID | LC SEQ ID NO: | SEQ ID NO: for L-CDR1 | L-CDR1 Sequence | SEQ ID NO: for L-CDR2 | L-CDR2 Sequence | SEQ ID NO: for L-CDR3 | L-CDR3 Sequence |
|---|---|---|---|---|---|---|---|
| L138 | 156 | 108 | KSSQSLLWFVNQKNYLT | 117 | HASTRES | 122 | QNDDSYPLT |
| L162 | 161 | 109 | KSSQSLLYVYGQKNYLT | 10 | WASTRES | 121 | QNDFSWPLT |
| L225 | 162 | 110 | KSSQSLLFRPTQKNYLT | 10 | WASTRES | 122 | QNDDSYPLT |
| L283 | 163 | 111 | KSSQSLLYTSNQKNYLT | 10 | WASTRES | 123 | QNDDYWPLT |
| L320 | 157 | 112 | KSSQSLLYSGNQRNYLT | 118 | WASTRSS | 124 | QNDDTYPMT |
| L327 | 158 | 113 | KSSQSLLPSWNQSNYLT | 10 | WASTRES | 125 | QNDFTYPLT |
| L335 | 159 | 114 | KSSQSLLFSANQRNYLT | 119 | WASTRDS | 126 | QNDDTYPLT |
| L369 | 160 | 115 | KSSQSLLTSYNQRNYLT | 10 | WASTRES | 127 | QNDLTYPLT |

Some of these Mabs were subjected to further characterization and tested in in vivo xenograft models (Example 5).

EXAMPLE 5

Characterization of MAbs

Following the human framework adaptation and reselection of a library of variants based on M59 comprising a single LC variable region (L3, SEQ ID NO: 23) and single HC variable region (H22, SEQ ID NO: 19), with altered residues in some CDR residues, the novel Mabs were subjected to biophysical and bioactivity assays, and one paring, M1587, with altered paratope residues was used to re-examine whether the epitope originally characterized for a 10H10Fab binding to TF-ECD (Example 2) was altered.

Human TF ECD: M1587 Interface

The co-crystallization of human-adapted and affinity matured antibody based on 10H10 CDRs, M1587 (L3 and H116) with TF ECD was performed in the same manner as for 10H10 (Example 3) except that the M1587-Fab:TF complex was crystallized from solution containing 16% PEG 3350, 0.2 M ammonium acetate, 0.1 M sodium acetate, pH 4.5.

Comparison of the co-crystal structure of human TF ECD with that with the affinity matured M1587 Fab indicates that the human adaptation and affinity maturation of 10H10 has not changed the antibody epitope footprint as shown in FIG. 2, nor have the conformation of the CDRs been altered. Three amino acid replacements (T31P, S57F, and N59T) were introduced in H-CDR1 and H-CDR2 (SEQ ID NO: 6 and 27, respectively, using the CDR definitions described in Example 2) during human framework adaption and affinity maturation (SEQ ID NO: 6 and 7 were replaced with SEQ ID NO: 63 and 86) including the contact residues at residue 31 and 57 of H116 (SEQ ID NO: 133) which are T31P and S57F. There was a five-fold affinity improvement that may be attributed to the increased interface of F57, which is in contact with 5195 of TF. The structure of human TF ECD with M1587 Fab confirmed the preservation of the epitope during HFA and affinity maturation even though changes were made in the H-CDR1 and H-CDR2 paratope residues.

Biophysical and Biological Assay Results

Figure 5:
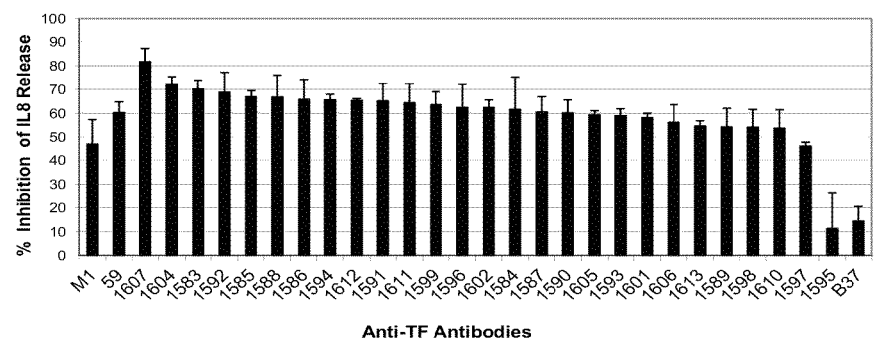
FIG. 5 shows the relative percent inhibition by the 27 affinity matured mAbs to FVIIa-induced IL-8 release at 0.24 ug/ml by MDB-MB-231 breast cancer cells compared to the isotype control B37.

Summary data for these antibodies is show below for the KD analysis by Biacore (Table 11), coagulation time of human plasma by human TF (Table 12), and the EC50 for IL8 release from MD-MB-231 cells stimulated with FVIIa (Table 13, 14, and FIG. 5).

The $K_D$ for 43 selected affinity matured Mabs and includes data generated for the murine 10H10 and chimeric version of that MAb (M1) with selected human framework adapted variants with unmodified CDR from 10H10 (M numbers less than 100) are shown in Table 11. Thus, the combination of human framework selection and CDR residue substitution produced human antibodies with $K_D$ in the range of 80 to 950 pM with an off rate (Koff) in the range of 2.2×10-5 sec-1 to 2.6×10-3 sec-1; and with an on rate (Kon) in the range of $10^4$ M-1 sec-1 to 2.3×$10^5$ M-1 sec-1. Compared to values for the original murine 10H10 or the chimeric construct, the novel Mabs have up to a 10-fold lower in equilibrium dissociation constant ($K_D$), from 0.77 nM to 0.08 nM; display a faster on rate ($K_{on}$>$10^5$ M-1 sec-1), or have a slower off rate (Koff=$10^5$ sec-1). These properties can be used to advantage in selecting a MAb for particular applications where either residence time or ability to penetrate tissues is desired.

TABLE 11

| Antibody ID | ka (1/Ms) $10^4$ | kd (1/s) $10^{-4}$ | $K_D$ (nM) |
|---|---|---|---|
| M1639 | 4.69 | 3.71 | 0.08 |
| M1645 | 5.21 | 4.12 | 0.08 |
| M1647 | 3.87 | 4.02 | 0.1 |
| M1652 | 4.44 | 4.82 | 0.11 |
| M1641 | 4.56 | 5.46 | 0.12 |
| M1644 | 5.81 | 7.19 | 0.12 |
| M1587 | 15.7 | 0.23 | 0.14 |
| M1604 | 15.2 | 0.22 | 0.14 |
| M1653 | 2.31 | 3.76 | 0.16 |
| M1649 | 3.85 | 6.46 | 0.17 |
| M1593 | 13.8 | 0.25 | 0.18 |
| M1606 | 16.55 | 0.29 | 0.18 |
| M1643 | 4.52 | 8.13 | 0.18 |
| M1646 | 3.5 | 6.47 | 0.19 |
| M1650 | 2.33 | 4.5 | 0.19 |
| M1651 | 2.01 | 3.88 | 0.19 |
| M58 | 9.48 | 0.18 | 0.19 |
| M1638 | 4.89 | 9.92 | 0.2 |
| M61 | 9.41 | 0.19 | 0.2 |
| M1584 | 18.4 | 0.56 | 0.3 |
| M1611 | 19.2 | 0.59 | 0.31 |
| M1596 | 13.1 | 0.43 | 0.33 |
| M1598 | 19.2 | 0.63 | 0.33 |
| M1601 | 13.7 | 0.46 | 0.33 |
| M1588 | 17.3 | 0.6 | 0.35 |
| M1594 | 12.4 | 0.43 | 0.35 |
| M1607 | 17 | 0.6 | 0.35 |
| M11 | 9.73 | 0.35 | 0.36 |
| M1612 | 16.5 | 0.63 | 0.38 |
| M1595 | 17.6 | 0.68 | 0.39 |
| M1599 | 13.8 | 0.53 | 0.39 |

TABLE 11-continued

| Antibody ID | ka (1/Ms) $10^4$ | kd (1/s) $10^{-4}$ | $K_D$ (nM) |
|---|---|---|---|
| M1589 | 17.4 | 0.7 | 0.4 |
| M1592 | 19.1 | 0.77 | 0.4 |
| M1591 | 13.4 | 0.56 | 0.41 |
| M19 | 9.88 | 0.41 | 0.41 |
| M59 | 9.33 | 0.38 | 0.41 |
| M1583 | 23.9 | 1 | 0.42 |
| M60 | 9.75 | 0.46 | 0.47 |
| M1585 | 18.5 | 0.9 | 0.49 |
| M46 | 9 | 0.44 | 0.49 |
| M1610 | 18.4 | 1 | 0.54 |
| M37 | 6.9 | 0.37 | 0.54 |
| M12 | 9.22 | 0.51 | 0.55 |
| M9 | 9.73 | 0.59 | 0.61 |
| M1602 | 13.2 | 0.82 | 0.62 |
| M1605 | 13.5 | 0.86 | 0.64 |
| M16 | 10.2 | 0.67 | 0.66 |
| M1590 | 15.9 | 1.09 | 0.69 |
| M1648 | 1.02 | 7.45 | 0.73 |
| M1640 | 1.02 | 7.8 | 0.76 |
| 10H10 | 8.88 | 0.68 | 0.76 |
| M1 | 9.52 | 0.74 | 0.77 |
| M10 | 9.26 | 0.71 | 0.77 |
| M1586 | 18.4 | 1.43 | 0.78 |
| M1597 | 8.34 | 0.66 | 0.8 |
| M1613 | 7.57 | 0.7 | 0.92 |
| M1642 | 2.74 | 26.1 | 0.95 |
| M42 | 8.04 | 0.82 | 1.02 |
| M26 | 8.26 | 0.93 | 1.13 |
| M68 | 6.43 | 1.03 | 1.6 |
| M51 | 8.11 | 2.35 | 2.9 |
| M52 | 7.4 | 2.64 | 3.57 |

Coagulation

The novel Mabs are characterized by the ability to bind human TF without blocking coagulation of human plasma as measured in vitro in the presence of calcium and exogenously added human TF (Table 12). Seventeen HFA (M number less than 100) variants and 38 affinity maturated variants (M1583 and above) were assayed and the $T_{1/2}$ Max (the time in seconds to reach 50% of the maximum optical density) reported.

All demonstrate responses similar to that observed with 10H10 (Table 12) with $T_{1/2}$ Max values less than 205 seconds, indicating these antibodies do not prolong the coagulation time when compared to the vehicle control with no antibody which was 159±17 (n=14). CNTO860, a human TF binding antibody described previously (U.S. Pat. No. 7,605,235 B2) and derived from the murine antibody 5G9 which blocks FX binding to TF, prolongs clotting and never reaches coagulation within 1800 sec in the same assay. Five of the 43 MAbs described in Example 4 as having altered CDRs, were not tested in the coagulation assay because they have starting concentration less than 2 mg/ml. M1, M59 and CNTO860 values were averaged over multiple tests.

TABLE 12

| MAb ID | T½ Max (seconds) (n = 2) | SD (seconds) |
|---|---|---|
| 10H10* | 191 | 2 |
| M1* | 173 | 5 |
| CNTO860* | >900 | 11 |
| M9 | 198 | 3 |
| M10 | 196 | 6 |
| M11 | 195 | 5 |
| M12 | 197 | 7 |
| M16 | 198 | 5 |
| M19 | 199 | 5 |
| M26 | 186 | 4 |
| M37 | 196 | 5 |
| M42 | 202 | 7 |
| M46 | 195 | 6 |
| M51 | 207 | 7 |
| M52 | 201 | 6 |
| M58 | 192 | 5 |
| M59* | 169 | 4 |
| M60 | 180 | 4 |
| M61 | 186 | 10 |
| M68 | 207 | 11 |
| M1583 | 189 | 8 |
| M1584 | 199 | 6 |
| M1585 | 205 | 12 |
| M1586 | 200 | 7 |
| M1587 | 202 | 10 |
| M1588 | 207 | 10 |
| M1589 | 202 | 3 |
| M1590 | 180 | 5 |
| M1591 | 154 | 6 |
| M1592 | 163 | 6 |
| M1593 | 164 | 7 |
| M1594 | 165 | 5 |
| M1595 | 163 | 5 |
| M1596 | 163 | 5 |
| M1597 | 157 | 6 |
| M1598 | 155 | 4 |
| M1599 | 151 | 6 |
| M1601 | 180 | 6 |
| M1602 | 163 | 7 |
| M1604 | 165 | 5 |
| M1605 | 160 | 5 |
| M1606 | 157 | 5 |
| M1607 | 152 | 6 |
| M1610 | 164 | 4 |
| M1611 | 154 | 10 |
| M1612 | 163 | 11 |
| M1613 | 165 | 11 |
| M1638 | 163 | 12 |
| M1639 | 167 | 5 |
| M1640 | 168 | 9 |
| M1641 | 162 | 9 |
| M1642 | 166 | 6 |
| M1643 | 148 | 6 |
| M1644 | 150 | 6 |
| M1645 | 154 | 4 |
| M1647 | 160 | 6 |
| M1648 | 161 | 3 |
| M1650 | 150 | 6 |

Signal Blocking Activity

The novel MAbs can also be described in terms of their ability to block signaling through the TF/FVIIa complex. TF/VIIa/PAR2 signaling of breast cancer cells induces a broad repertoire of proangiogenic factors such as VEGF25, Cyr61, VEGF-C, CTGF, CXCL1, and IL-8. It was previously reported that FVIIa induces detectable IL-8 in MDA-MB-231???, a human breast cancer cell line expressing TF (Albrektsen et al., J Thromb Haemost 5: 1588-1597, 2007). Therefore, this assay was used as a biological assay to evaluate the variant antibodies ability to inhibit TF/VIIa induction of IL-8 production.

The details of the assay are given herein above and the results of testing 19 of the HFA (M10-M68) variants of Example 3 and 29 of the CDR variants of Example 4 were tested for the ability to inhibit IL-8 production at a single concentration of TF (0.5 microgm per ml). An anti-RSV antibody (B37) that does not bind Tissue Factor, used as a negative control. At this concentration, many of the HFA Mabs were able to block IL-8 induction by more than 67% (Table 13). FIG. 5 shows the relative inhibition of IL8-release by 27 of the MAbs sharing the L3 light chain (SEQ ID NO: 23) and having substitutions in H-CDR1 or H-CDR2 as compared to those of 10H10 (SEQ ID NO: 6 and 7, respectively). In addition; four of these: M1584, M1611, TF7M1612 and TF7M1607 were placed in a full titration IL-8 induction assay along with M. The relative IC50 values calculated further support the observation that the affinity improved variants are more potent as compared to M1, the mouse-human chimera of 10H10 (Table 14). The other affinity mature groups of affinity maturated antibodies described in Example 4 produced similar results.

TABLE 13

| Variants ID | % IL-8 Inhibition | SD |
| --- | --- | --- |
| 10H10 | 93.9 | 8.0 |
| M1 | 96.1 | 7.6 |
| M9 | 102.7 | 4.5 |
| M10 | 90.7 | 0.0 |
| M11 | 87.9 | 9.4 |
| M12 | 98.6 | 3.1 |
| M16 | 98.3 | 6.2 |
| M19 | 87.3 | 5.8 |
| M26 | 79.1 | 1.3 |
| M37 | 71.2 | 11.6 |
| M42 | 86.0 | 20.1 |
| M46 | 82.5 | 10.7 |
| M51 | 71.5 | 9.4 |
| M52 | 67.7 | 4.0 |
| M58 | 88.5 | 8.5 |
| M59 | 83.8 | 8.0 |
| M60 | 99.6 | 4.5 |
| M61 | 106.8 | 4.9 |
| M68 | 89.8 | 11.1 |

TABLE 14

| MAb ID | IC50 (ug/ml) |
| --- | --- |
| M1 | 0.527 |
| M59 | 0.382 |
| M1584 | 0.332 |
| M1607 | 0.395 |
| M1611 | 0.398 |
| M1612 | 0.413 |

EXAMPLE 6

Antibody Antitumor Activity

Mouse Xenograft Model with MDA-MB-231

MDA-MB-231 human breast cancer cells were cultured in DMEM medium with 10% FBS and 1% LNN, harvested at log phase by trypsinization, and resuspended in sterile serum-free DMEM media at $5 \times 10^7$ cells/mL. Twenty female SCID Beige (C.B-17/IcrCrl-scid-bgBR) mice were obtained from Charles River Laboratories and acclimated for 14 days prior to experimentation. At approximately eight weeks of age, mice were implanted in the right axillary mammary fat pad with $2.5 \times 10^6$ MDA-MB-231 cells. When tumors were approximately 100 mm³ in size, mice were stratified by tumor size into treatment groups (N=10 per group). Intraperitoneal treatment with Dulbecco's Phosphate Buffered Saline (DPBS) or M1593 at 10 mg/kg of body weight, commenced on the day of stratification, and continued once weekly for a total of six doses. Tumors and body weights were recorded once weekly. The study terminated when the mean tumor volume of each group reached 1500 mm³. Statistical tests applied were two-way repeated measures ANOVA (PRIZM 4.0, GraphPad).

Figure 6:
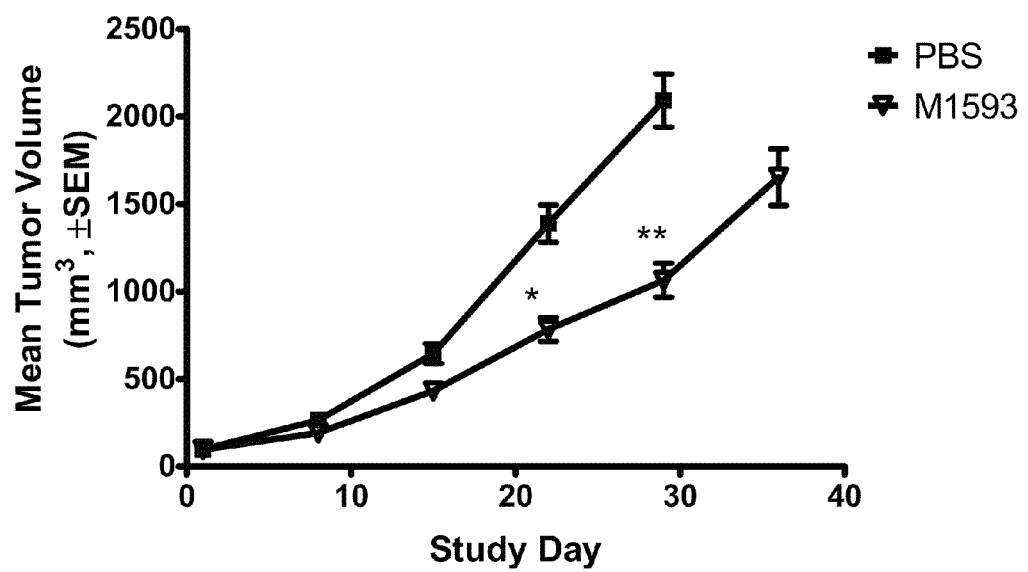
FIG. 6 shows a plot of tumor volume over days post-implantation of MDA-MB231 tumor cells in immunocompromised mice where the group dosed with M1593 reduced growth of an established tumor.

In MDA-MB-231 xenograft model, M1593 significantly inhibited tumor growth beginning on Day 22 (*P<0.01) and continuing until Day 29 (**P<0.001), at which point the control (DPBS-treated) group was euthanized. The M1593 treated group was euthanized on Day 36. M1593 inhibited tumor growth by approximately 49% on Day 29. There was an approximately 11-day tumor growth delay in the M1593 treated group, relative to the DPBS-treated control group (FIG. 6).

Mouse Xenograft Model with A431

A431 human squamous cell carcinoma cells were cultured in DMEM medium with 10% FBS and 1% LNN, harvested at log phase by trypsinization, and resuspended in sterile HBSS at $1 \times 10^7$ cells/mL. Twenty female SCID Beige (C.B-17/Icr-Crl-scid-bgBR) mice were obtained from Charles River Laboratories and acclimated for 14 days prior to experimentation. At approximately eight weeks of age, mice were implanted in the right flank with $2 \times 10^6$ A431 cells. When tumors were approximately 118 mm³ in size, mice were stratified by tumor size into treatment groups (N=10 per group). Intraperitoneal treatment with DPBS or M1593 at 10 mg/kg of body weight, commenced on the day of stratification, and continued once weekly for a total of six doses. Tumors and body weights were recorded twice weekly. The study terminated when the mean tumor volume of each group reached 1000 mm³. Statistical tests applied were two-way repeated measures ANOVA (PRIZM 4.0, GraphPad).

Figure 7:
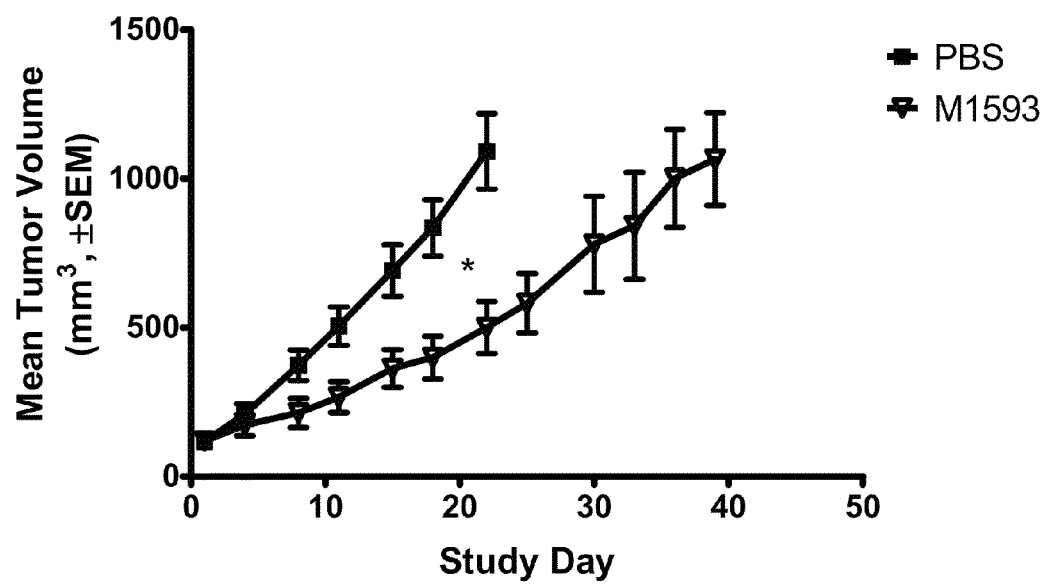
FIG. 7 shows a plot of tumor volume over days post-implantation of A431 human squamous tumor cells in immunocompromised mice where the group dosed with M1593 reduced growth of an established tumor.

M1593 significantly inhibited tumor growth on Day 22 (*P=0.0067), at which point the control (DPBS treated) group was euthanized. The CNTO592-treated group was euthanized on Day 39. CNTO592 inhibited tumor growth by approximately 54% on Day 22. There was an approximately 17-day tumor growth delay in the M1593 treated group, relative to the DPBS-treated control group (FIG. 7).

EXAMPLE 7

Antibody Compositions with Altered $F_C$

Naturally occurring human Fc receptor variants have substantially differing affinities for the Fc-portion of human antibodies. In addition, clinical studies have demonstrated improved response rates and survival for patients with tight binding Fc genotypes after treatment with Fc-engineered mAbs (Musolino et al 2008 J Clin Oncol 26:1789-1796 (2008); Bibeau et al 2009 J Clin Oncol 27:1122-1129).

While inhibition of TF signaling is expected to reduce cellular responses leading to tumor proliferation, migration, and metastasic spread, the fact that TF antigen is displayed on tumor cells provides for a means for selective killing of the target cell by mechanisms related to Fc-receptor engagement by the antibody Fc. The surface features of the Fc-domain of the antibody are known to be influenced by the glycan composition as well as the primary sequence of the heavy chains, and modification of either or both can alter Fc-receptor binding.

The MAb identified as M1593, was produced as a low fucose glycan-modified IgG1 and also as a IgG1-CH2 domain variant (S239D, I332E where the numbering is that of Kabat EU system).

MAb Compositions and Methods of Making

The antibody with low fucose content (M1593-LF) was produced by electroporating a vector encoding the M1593 (IgG1/Kappa) chains as shown below with signal peptides into a CHO host cell subline selected for low fucosylation of proteins from the CHO host cell line. SEQ ID NO: 165 represents the complete light chain comprising the variable domain, residues 1-113 (SEQ ID NO: 23 plus FR4, SEQ ID NO: 61, underlined) and the human kappa constant light domain. The heavy chains comprising the variable domain residues 1-120 (which includes SEQ ID NO: 139 and FR4 SEQ ID NO: 60, underlined) with wild-type human IgG isotype1 CH1, CH2, and CH3 where the Kabat positions 239 and 332 (which are 242 And 335 of SEQ ID NO: 167) are modified from the wild-type residues S and D, to D and E, respectively to form the variant M1593-DE.

M1593-Light Chain
(SEQ ID NO: 165)
DIVMTQTPLSLPVTPGEPASISCKSSQSLLSSGNQKNYLTWYLQKPGQSP

QLLIYWASTRESGVPDRFSGSGSGTDFTLKISRVEAEDVGVYYCQNDYTY

PLTFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

M1593-heavy chain where Kabat position
S239 is D, and I332 is E
(SEQ ID NO: 167)
EVQLVQSGAEVKKPGESLRISCKGSGYTFAPYWIEWVRQMPGKGLEWMGD

ILPGTGFTTYSPSFQGHVTISADKSISTAYLQWSSLKASDTAMYYCARSG

YYGNSGFAYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPDVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPEEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

The CHO cell was generated by sub-cloning after four rounds of negative lectin selection (selection of non-binding to fucose binding lectin) and FACS sorting to isolate a pool of naturally occurring low fucose cells to be used as a host cell line. This line was derived from the same host cells used to produced M1593 and therefore, the cells are cultured and handled exactly in the same manner. Transfected cells were screened by methylcellulose plating using protein G for detection and colonies picked into 96-well plates. Cultures were expanded to shaker flasks for titering. Top parental clones produced M1593-LF up to 708 mg/L (in standard medium) in batch shake flask cultures.

LC-MS glycopeptide mapping was performed on two M1593-LF producing clones (C2452B and C2452D) to determine the percent fucosylation and evaluate the stability of the glycosylation profile over time and production process (Table 15). Samples were collected during a stability study from passage 1 fed-batch and passage 10 batch cultures and purified. Purified samples from the bioreactor evaluation were also analyzed. Glycopeptide mapping showed favorable glycosylation patterns with low percent total fucosylation from C2452B and C2452D. Importantly, the percent fucosylation did not significantly increase over time which suggests that the host cell fucosylation is stable. Thus, the fucose content for M1593-LF is less than 10%, and generally, less than 5% and, in some preparations, less than 2%. Mab produced in the non-lectin selected host CHO cell comprised glycan groups where greater than 80% were fucosylated. Table 15.

| Clone | % Fucosylation | Sample Analyzed |
|---|---|---|
| C2452B | 2.81 | P1 Shake Flask Fed-batch |
| C2452B | 1.83 | p10 Batch of Stability Study |
| C2452B | 3.67 | Bioreactor |
| C2452D | 2.20 | P1 Shake Flask Fed-batch |
| C2452D | 2.25 | p10 Batch of Stability Study |
| C2452D | 7.31 | Bioreactor |

For the mutant Fc variant of M1593 (M1593-DE), the plasmid expressing M1593 was subjected to site directed mutagenesis.

Biological Activity

The three anti-human TF Fc variants (M1593, M1593-LF, and M1593-DE) affinity for both human and cynomolgus Fc receptors (FcγRI, FcγRIIa, FcγRIIIa). These assays were performed as described in applicants co-pending application (U.S. Ser. No. 61/426,619) or by using Plasmon resonance (Biacore) based binding assays (?).

The results of these assays demonstrated that both Fc modified anti-TF antibodies bound much more tightly to recombinant human FcγIIIa receptors compared with the parental, unmodified IgG1 M1593 antibody by 18-fold (M1593-LF) and 40-fold (M1593-DE) (Table 16).

TABLE 16

Anti-TF antibody affinities for human FcγIIIa receptors

| MAb | Human FcγIIIa $K_D$ (M) |
|---|---|
| M1593 (wild-type human IgG1/kappa constant domains) | $2.1 \times 10^{-7}$ |
| M1593-DE (hIgG1 with S239D/I332E) | $5.0 \times 10^{-9}$ |
| M1593-LF (hIgG1 produced in host subline producing reduced fucosylation in glycans) | $1.2 \times 10^{-8}$ |

ADCC is stimulated by FcγRIIIa engagement. ADCC assays were performed as previously described (Scallon et al., Mol Immunol 44:1524-1534 2007).

Figure 8:
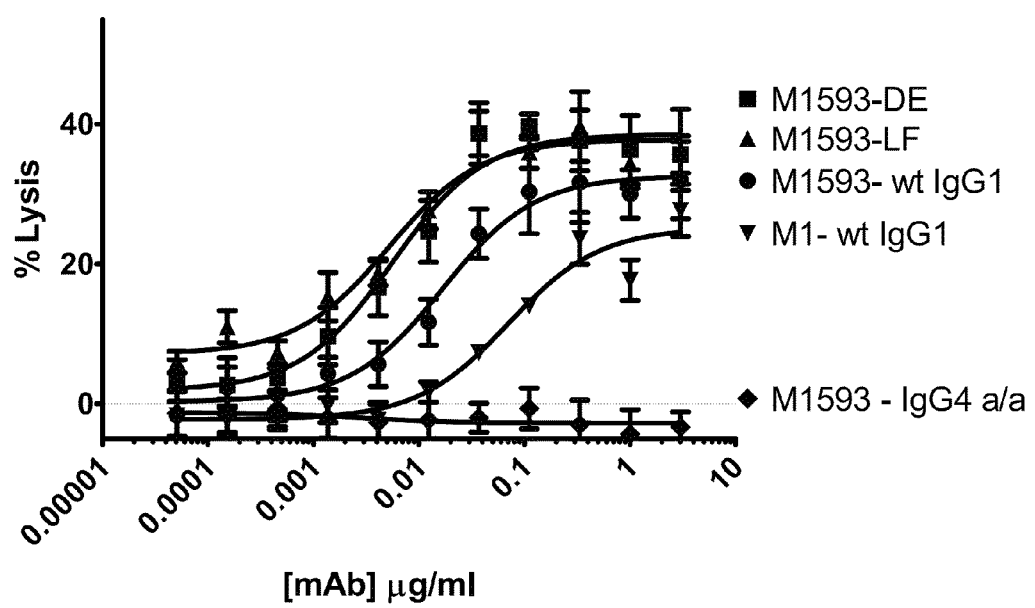
FIG. 8 shows a plot of the percent target cell lysis (MDA-MB231 cells) by human PBMC versus MAb concentrations for the murine variable domain-human IgG1 (M1), murine variable domain-human IgG4 with alanine substitution at positions 234 and 235, M1593 as wild-type IgG1 produced in unmodified CHO, as M1593-LF produced in a CHO line selected for producing glycan with low fucose content, and M1593-DE with Kabat position substitutions at S239D and I332E.

Improved Fc receptor binding was reflected in functional in vitro ADCC assays using human PBMC as effector cells and human breast cancer cell line MDA-MB-231 as the target cell (FIG. 8).

What is claimed:

1. An isolated anti-tissue factor antibody comprising three heavy chain CDR sequences, H-CDR1, H-CDR2, and H-CDR3, represented by SEQ ID NOs: 76, 98, and 8, respectively, and three light chain CDR sequences L-CDR1, L-CDR2, and L-CDR3, represented by SEQ ID NOs: 9, 10, and 11, respectively.

2. An isolated anti-tissue factor antibody comprising an antibody light chain variable domain of SEQ ID NO: 23 or an antibody heavy chain variable domain of SEQ ID NO: 139.

3. The antibody of claim 2, comprising both the antibody light chain variable domain of SEQ ID NO: 23 and the antibody heavy chain variable domain of SEQ ID NO: 139.

4. The antibody of claim 2, comprising an antibody light chain of SEQ ID NO: 165.

5. The antibody of claim 2, comprising an antibody heavy chain selected from SEQ ID NO: 166 and SEQ ID NO: 167.

6. The antibody of claim 5, comprising an antibody heavy chain of SEQ ID NO: 166.

7. The antibody of claim 5, comprising an antibody heavy chain of SEQ ID NO: 167.

8. The antibody of claim 2, comprising an antibody light chain of SEQ ID NO: 165 and an antibody heavy chain selected from SEQ ID NO: 166 and SEQ ID NO: 167.

9. The antibody of claim 2, wherein the antibody is an anti-tissue factor antibody that does not compete with FVIIa for tissue factor binding and does not substantially block the procoagulant, amidolytic activity of the TF-VIIa complex but which does block TF-VIIa mediated signaling as measured by cytokine IL-8 release from MDA-MB-231 cells.

10. A pharmaceutical composition comprising an antibody of claim 1.

11. A pharmaceutical composition comprising an antibody of claim 2.

12. The pharmaceutical composition of claim 9, wherein the antibody is an antibody of claim 4.

13. The pharmaceutical composition of claim 9, wherein the antibody is an antibody of claim 5.

14. A nucleic acid encoding an antibody comprising the heavy chain CDR sequences and light chain CDR sequences as claimed in claim 1.

15. A nucleic acid encoding an antibody light chain variable domain or an antibody heavy chain variable domain as claimed in claim 2.

16. A nucleic acid encoding an antibody light chain as claimed in claim 4.

17. A nucleic acid encoding an antibody heavy chain as claimed in claim 5.

18. A vector comprising at least one polynucleotide of claim 14.

19. A host cell comprising the vector of claim 18.

* * * * *

SEQUENCE LISTING

<160> NUMBER OF SEQ ID NOS: 167

<210> SEQ ID NO 1
<211> LENGTH: 263
<212> TYPE: PRT
<213> ORGANISM: Homo sapiens

<400> SEQUENCE: 1

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
                35                  40                  45

Cys Phe Tyr Thr Thr Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
                115                 120                 125

Asp Glu Arg Thr Leu Val Arg Arg Asn Asn Thr Phe Leu Ser Leu Arg
            130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu Ile Phe Tyr Ile Ile
210                 215                 220

Gly Ala Val Val Phe Val Val Ile Ile Leu Val Ile Ile Leu Ala Ile
225                 230                 235                 240

Ser Leu His Lys Cys Arg Lys Ala Gly Val Gly Gln Ser Trp Lys Glu
            245                 250                 255

Asn Ser Pro Leu Asn Val Ser
            260

<210> SEQ ID NO 2
<211> LENGTH: 220
<212> TYPE: PRT
<213> ORGANISM: Macaca fascicularis

<400> SEQUENCE: 2

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Ile Asn Gln
            20                  25                  30

Val Tyr Thr Val Gln Ile Ser Thr Lys Ser Gly Asp Trp Lys Ser Lys
                35                  40                  45

Cys Phe Tyr Thr Ala Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly His Val Glu Ser Thr Gly Ser Thr Glu Glu Pro Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Gln
        115                 120                 125

Asp Glu Trp Thr Leu Val Arg Arg Asn Asp Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
                180                 185                 190

Ile Pro Ser Arg Arg Thr Ala Asn Arg Lys Ser Thr Asp Ser Pro Val
                195                 200                 205

Glu Cys Met Gly His Glu Lys Gly Glu Ser Arg Glu
        210                 215                 220

<210> SEQ ID NO 3
<211> LENGTH: 266
<212> TYPE: PRT
<213> ORGANISM: Mus musculus

<400> SEQUENCE: 3

Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
                20                  25                  30

Thr Val Gln Ile Ser Asp Arg Ser Arg Asn Trp Lys Asn Lys Cys Phe
            35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
                100                 105                 110

Gly Gln Pro Val Ile Gln Gln Phe Glu Gln Asp Gly Arg Lys Leu Asn
            115                 120                 125

Val Val Val Lys Asp Ser Leu Thr Leu Val Arg Lys Asn Gly Thr Phe
130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
                180                 185                 190

Val Gln Ala Met Ile Phe Ser Arg Lys Thr Asn Gln Asn Ser Pro Gly
            195                 200                 205

Ser Ser Thr Val Cys Thr Glu Gln Trp Lys Ser Phe Leu Gly Glu Thr
    210                 215                 220

Leu Ile Ile Val Gly Ala Val Val Leu Ala Thr Ile Phe Ile Ile
225                 230                 235                 240

Leu Leu Ser Ile Ser Leu Cys Lys Arg Arg Lys Asn Arg Ala Gly Gln
                245                 250                 255

Lys Gly Lys Asn Thr Pro Ser Arg Leu Ala
                260                 265

<210> SEQ ID NO 4
<211> LENGTH: 120
<212> TYPE: PRT
<213> ORGANISM: Mus musculus

<400> SEQUENCE: 4

Gln Val His Leu Gln Gln Ser Gly Ala Glu Leu Met Lys Pro Gly Ala
1               5                   10                  15

Ser Val Lys Ile Ser Cys Lys Ala Ser Gly Tyr Thr Phe Ile Thr Tyr
                20                  25                  30

Trp Ile Glu Trp Val Lys Gln Arg Pro Gly His Gly Leu Glu Trp Ile
            35                  40                  45

Gly Asp Ile Leu Pro Gly Ser Gly Ser Thr Asn Tyr Asn Glu Asn Phe
        50                  55                  60

Lys Gly Lys Ala Thr Phe Thr Ala Asp Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Gly Tyr Tyr Gly Asn Ser Gly Phe Ala Tyr Trp Gly Gln
                100                 105                 110

Gly Thr Leu Val Thr Val Ser Ala
        115                 120

<210> SEQ ID NO 5
<211> LENGTH: 113
<212> TYPE: PRT
<213> ORGANISM: Mus musculus

<400> SEQUENCE: 5

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Ser Ser
                20                  25                  30

Gly Asn Gln Lys Asn Tyr Leu Thr Trp Tyr Gln Gln Ile Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Asn
                85                  90                  95

Asp Tyr Thr Tyr Pro Leu Thr Phe Gly Ala Gly Thr Lys Leu Glu Leu
                100                 105                 110

Lys

<210> SEQ ID NO 6
<211> LENGTH: 10
<212> TYPE: PRT
<213> ORGANISM: Mus musculus

<400> SEQUENCE: 6

Gly Tyr Thr Phe Ile Thr Tyr Trp Ile Glu
1               5                   10

<210> SEQ ID NO 7
<211> LENGTH: 17
<212> TYPE: PRT
<213> ORGANISM: Mus musculus

<400> SEQUENCE: 7

Asp Ile Leu Pro Gly Ser Gly Ser Thr Asn Tyr Asn Glu Asn Phe Lys
1               5                   10                  15

Gly

<210> SEQ ID NO 8
<211> LENGTH: 11
<212> TYPE: PRT
<213> ORGANISM: Mus musculus

<400> SEQUENCE: 8

Ser Gly Tyr Tyr Gly Asn Ser Gly Phe Ala Tyr
1               5                   10

<210> SEQ ID NO 9
<211> LENGTH: 17
<212> TYPE: PRT
<213> ORGANISM: Mus musculus

<400> SEQUENCE: 9

Lys Ser Ser Gln Ser Leu Leu Ser Gly Asn Gln Lys Asn Tyr Leu
1               5                   10                  15

Thr

<210> SEQ ID NO 10
<211> LENGTH: 7
<212> TYPE: PRT
<213> ORGANISM: Mus musculus

<400> SEQUENCE: 10

Trp Ala Ser Thr Arg Glu Ser
1               5

<210> SEQ ID NO 11
<211> LENGTH: 9
<212> TYPE: PRT
<213> ORGANISM: Mus musculus

<400> SEQUENCE: 11

Gln Asn Asp Tyr Thr Tyr Pro Leu Thr
1               5

<210> SEQ ID NO 12
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 12

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ile Thr Tyr
            20                  25                  30

Trp Ile Glu Trp Val Arg Gln Met Pro Gly Lys Gly Leu Glu Trp Met
        35                  40                  45

Gly Asp Ile Leu Pro Gly Ser Gly Ser Thr Asn Tyr Asn Glu Asn Phe
    50                  55                  60

Lys Gly His Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95
Ala Arg Ser Gly Tyr Tyr Gly Asn Ser Gly Phe Ala Tyr
            100                 105
```

<210> SEQ ID NO 13
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 13

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ile Thr Tyr
                20                  25                  30
Trp Ile Glu Trp Val Arg Gln Ala Pro Gly Gln Gly Leu Glu Trp Met
            35                  40                  45
Gly Asp Ile Leu Pro Gly Ser Gly Ser Thr Asn Tyr Asn Glu Asn Phe
        50                  55                  60
Lys Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ser Gly Tyr Tyr Gly Asn Ser Gly Phe Ala Tyr
            100                 105
```

<210> SEQ ID NO 14
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 14

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ile Thr Tyr
                20                  25                  30
Trp Ile Glu Trp Val Arg Gln Ala Pro Gly Gln Arg Leu Glu Trp Met
            35                  40                  45
Gly Asp Ile Leu Pro Gly Ser Gly Ser Thr Asn Tyr Asn Glu Asn Phe
        50                  55                  60
Lys Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Gly Tyr Tyr Gly Asn Ser Gly Phe Ala Tyr
            100                 105
```

<210> SEQ ID NO 15
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 15

```
Glu Val Gln Leu Val Glu Ser Gly Gly Leu Val Gln Pro Gly Gly
1               5                   10                  15

Ser Leu Arg Leu Ser Cys Ala Ala Ser Gly Tyr Thr Phe Ile Thr Tyr
            20                  25                  30

Trp Ile Glu Trp Val Arg Gln Ala Pro Gly Lys Gly Leu Val Trp Val
            35                  40                  45

Ser Asp Ile Leu Pro Gly Ser Gly Ser Thr Asn Tyr Asn Glu Asn Phe
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ser Gly Tyr Tyr Gly Asn Ser Gly Phe Ala Tyr
            100                 105
```

<210> SEQ ID NO 16
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 16

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ile Thr Tyr
            20                  25                  30

Trp Ile Glu Trp Val Arg Gln Ala Pro Gly Gln Gly Leu Glu Trp Met
            35                  40                  45

Gly Asp Ile Leu Pro Gly Ser Gly Ser Thr Asn Tyr Asn Glu Asn Phe
50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Gly Tyr Tyr Gly Asn Ser Gly Phe Ala Tyr
            100                 105
```

<210> SEQ ID NO 17
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 17

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Thr Tyr
            20                  25                  30

Trp Ile Glu Trp Val Arg Gln Ala Pro Gly Gln Gly Leu Glu Trp Met
            35                  40                  45

Gly Asp Ile Leu Pro Gly Ser Gly Ser Thr Asn Tyr Asn Glu Asn Phe
50                  55                  60

Lys Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
            85                  90                  95

Ala Arg Ser Gly Tyr Tyr Gly Asn Ser Gly Phe Ala Tyr
            100                 105

<210> SEQ ID NO 18
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 18

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Ile Thr Tyr
            20                  25                  30

Trp Ile Glu Trp Val Gln Ala Pro Gly Lys Gly Leu Glu Trp Met
        35                  40                  45

Gly Asp Ile Leu Pro Gly Ser Gly Ser Thr Asn Tyr Asn Glu Asn Phe
50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Thr Ser Gly Tyr Tyr Gly Asn Ser Gly Phe Ala Tyr
            100                 105

<210> SEQ ID NO 19
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 19

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ile Thr Tyr
            20                  25                  30

Trp Ile Glu Trp Val Arg Gln Met Pro Gly Lys Gly Leu Glu Trp Met
        35                  40                  45

Gly Asp Ile Leu Pro Gly Ser Gly Ser Thr Asn Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Ser Gly Tyr Tyr Gly Asn Ser Gly Phe Ala Tyr
            100                 105

<210> SEQ ID NO 20
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 20
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ile Thr Tyr
            20                  25                  30

Trp Ile Glu Trp Val Arg Gln Ala Pro Gly Gln Gly Leu Glu Trp Met
        35                  40                  45

Gly Asp Ile Leu Pro Gly Ser Gly Ser Thr Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Tyr Gly Asn Ser Gly Phe Ala Tyr
            100                 105

<210> SEQ ID NO 21
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 21

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Ile Thr Tyr
            20                  25                  30

Trp Ile Glu Trp Val Gln Gln Ala Pro Gly Lys Gly Leu Glu Trp Met
        35                  40                  45

Gly Asp Ile Leu Pro Gly Ser Gly Ser Thr Asn Tyr Ala Glu Lys Phe
50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Gly Tyr Tyr Gly Asn Ser Gly Phe Ala Tyr
            100                 105

<210> SEQ ID NO 22
<211> LENGTH: 103
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
            85                  90                  95

Asp Tyr Thr Tyr Pro Leu Thr
            100

<210> SEQ ID NO 23
<211> LENGTH: 103
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 23

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ser Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
            85                  90                  95

Asp Tyr Thr Tyr Pro Leu Thr
            100

<210> SEQ ID NO 24
<211> LENGTH: 103
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Ser Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
            85                  90                  95

Asp Tyr Thr Tyr Pro Leu Thr
            100

<210> SEQ ID NO 25
<211> LENGTH: 103
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 25

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Ser Ser
            20                  25                  30

Gly Asn Gln Lys Asn Tyr Leu Thr Trp Tyr Leu Gln Lys Pro Gly Gln
        35                  40                  45

Pro Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Thr Tyr Pro Leu Thr
                100
```

```
<210> SEQ ID NO 26
<211> LENGTH: 103
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 26

Asp Ile Val Met Thr Gln Thr Pro Leu Ser Ser Pro Val Thr Leu Gly
1               5                   10                  15

Gln Pro Ala Ser Ile Ser Cys Lys Ser Ser Gln Ser Leu Leu Ser Ser
            20                  25                  30

Gly Asn Gln Lys Asn Tyr Leu Thr Trp Leu Gln Gln Arg Pro Gly Gln
        35                  40                  45

Pro Pro Arg Leu Leu Ile Tyr Trp Ala Ser Thr Arg Glu Ser Gly Val
    50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Thr Tyr Pro Leu Thr
                100
```

```
<210> SEQ ID NO 27
<211> LENGTH: 10
<212> TYPE: PRT
<213> ORGANISM: Mus musculus

<400> SEQUENCE: 27

Asp Ile Leu Pro Gly Ser Gly Ser Thr Asn
1               5                   10
```

```
<210> SEQ ID NO 28
<211> LENGTH: 25
<212> TYPE: PRT
<213> ORGANISM: Homo sapiens

<400> SEQUENCE: 28

Glu Val Gln Leu Val Gln Ser Gly Ala Glu Val Lys Lys Pro Gly Glu
1               5                   10                  15

Ser Leu Arg Ile Ser Cys Lys Gly Ser
            20                  25
```

```
<210> SEQ ID NO 29
<211> LENGTH: 25
<212> TYPE: PRT
<213> ORGANISM: Homo sapiens

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 30
<211> LENGTH: 25
<212> TYPE: PRT
<213> ORGANISM: Homo sapiens

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 31
<211> LENGTH: 25
<212> TYPE: PRT
<213> ORGANISM: Homo sapiens

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 32
<211> LENGTH: 25
<212> TYPE: PRT
<213> ORGANISM: Homo sapiens

<400> SEQUENCE: 32

Glu Val Gln Leu Val Gln Ser Gly Ala Glu Val Lys Lys Pro Gly Ala
1               5                   10                  15

Thr Val Lys Ile Ser Cys Lys Val Ser
            20                  25

<210> SEQ ID NO 33
<211> LENGTH: 14
<212> TYPE: PRT
<213> ORGANISM: Homo sapiens

<400> SEQUENCE: 33

Trp Val Arg Gln Met Pro Gly Lys Gly Leu Glu Trp Met Gly
1               5                   10

<210> SEQ ID NO 34
<211> LENGTH: 14
<212> TYPE: PRT
<213> ORGANISM: Homo sapiens

<400> SEQUENCE: 34

Trp Val Arg Gln Ala Pro Gly Gln Gly Leu Glu Trp Met Gly
1               5                   10

<210> SEQ ID NO 35
<211> LENGTH: 14
```

```
<212> TYPE: PRT
<213> ORGANISM: Homo sapiens

<400> SEQUENCE: 35

Trp Val Arg Gln Ala Pro Gly Gln Arg Leu Glu Trp Met Gly
1               5                   10

<210> SEQ ID NO 36
<211> LENGTH: 14
<212> TYPE: PRT
<213> ORGANISM: Homo sapiens

<400> SEQUENCE: 36

Trp Val Arg Gln Ala Pro Gly Lys Gly Leu Val Trp Val Ser
1               5                   10

<210> SEQ ID NO 37
<211> LENGTH: 14
<212> TYPE: PRT
<213> ORGANISM: Homo sapiens

<400> SEQUENCE: 37

Trp Val Gln Gln Ala Pro Gly Lys Gly Leu Glu Trp Met Gly
1               5                   10

<210> SEQ ID NO 38
<211> LENGTH: 32
<212> TYPE: PRT
<213> ORGANISM: Homo sapiens

<400> SEQUENCE: 38

His Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 39
<211> LENGTH: 32
<212> TYPE: PRT
<213> ORGANISM: Homo sapiens

<400> SEQUENCE: 39

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 40
<211> LENGTH: 32
<212> TYPE: PRT
<213> ORGANISM: Homo sapiens

<400> SEQUENCE: 40

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 41
<211> LENGTH: 32
<212> TYPE: PRT
<213> ORGANISM: Homo sapiens

<400> SEQUENCE: 41
```

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 42
<211> LENGTH: 32
<212> TYPE: PRT
<213> ORGANISM: Homo sapiens

<400> SEQUENCE: 42

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 43
<211> LENGTH: 32
<212> TYPE: PRT
<213> ORGANISM: Homo sapiens

<400> SEQUENCE: 43

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 44
<211> LENGTH: 32
<212> TYPE: PRT
<213> ORGANISM: Homo sapiens

<400> SEQUENCE: 44

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 45
<211> LENGTH: 39
<212> TYPE: PRT
<213> ORGANISM: Homo sapiens

<400> SEQUENCE: 45

Tyr Ser Pro Ser Phe Gln Gly His Val Thr Ile Ser Ala Asp Lys Ser
1               5                   10                  15

Ile Ser Thr Ala Tyr Leu Gln Trp Ser Ser Leu Lys Ala Ser Asp Thr
            20                  25                  30

Ala Met Tyr Tyr Cys Ala Arg
        35

<210> SEQ ID NO 46
<211> LENGTH: 39
<212> TYPE: PRT
<213> ORGANISM: Homo sapiens

<400> SEQUENCE: 46

Tyr Ala Gln Lys Phe Gln Gly Arg Val Thr Ile Thr Ala Asp Glu Ser
1               5                   10                  15

Thr Ser Thr Ala Tyr Met Glu Leu Ser Ser Leu Arg Ser Glu Asp Thr
            20                  25                  30

Ala Val Tyr Tyr Cys Ala Arg

<210> SEQ ID NO 47
<211> LENGTH: 39
<212> TYPE: PRT
<213> ORGANISM: Homo sapiens

<400> SEQUENCE: 47

Tyr Ala Glu Lys Phe Gln Gly Arg Val Thr Ile Thr Ala Asp Thr Ser
1               5                   10                  15

Thr Asp Thr Ala Tyr Met Glu Leu Ser Ser Leu Arg Ser Glu Asp Thr
            20                  25                  30

Ala Val Tyr Tyr Cys Ala Thr
            35

<210> SEQ ID NO 48
<211> LENGTH: 23
<212> TYPE: PRT
<213> ORGANISM: Homo sapiens

<400> SEQUENCE: 48

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 49
<211> LENGTH: 23
<212> TYPE: PRT
<213> ORGANISM: Homo sapiens

<400> SEQUENCE: 49

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 50
<211> LENGTH: 23
<212> TYPE: PRT
<213> ORGANISM: Homo sapiens

<400> SEQUENCE: 50

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 51
<211> LENGTH: 23
<212> TYPE: PRT
<213> ORGANISM: Homo sapiens

<400> SEQUENCE: 51

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 52
<211> LENGTH: 23
<212> TYPE: PRT
<213> ORGANISM: Homo sapiens

<400> SEQUENCE: 52

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 53
<211> LENGTH: 15
<212> TYPE: PRT
<213> ORGANISM: Homo sapiens

<400> SEQUENCE: 53

Trp Tyr Gln Gln Lys Pro Gly Gln Pro Pro Lys Leu Leu Ile Tyr
1               5                   10                  15

<210> SEQ ID NO 54
<211> LENGTH: 15
<212> TYPE: PRT
<213> ORGANISM: Homo sapiens

<400> SEQUENCE: 54

Trp Tyr Leu Gln Lys Pro Gly Gln Ser Pro Gln Leu Leu Ile Tyr
1               5                   10                  15

<210> SEQ ID NO 55
<211> LENGTH: 15
<212> TYPE: PRT
<213> ORGANISM: Homo sapiens

<400> SEQUENCE: 55

Trp Tyr Leu Gln Lys Pro Gly Gln Pro Pro Gln Leu Leu Ile Tyr
1               5                   10                  15

<210> SEQ ID NO 56
<211> LENGTH: 15
<212> TYPE: PRT
<213> ORGANISM: Homo sapiens

<400> SEQUENCE: 56

Trp Leu Gln Gln Arg Pro Gly Gln Pro Pro Arg Leu Leu Ile Tyr
1               5                   10                  15

<210> SEQ ID NO 57
<211> LENGTH: 32
<212> TYPE: PRT
<213> ORGANISM: Homo sapiens

<400> SEQUENCE: 57

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 58
<211> LENGTH: 32
<212> TYPE: PRT
<213> ORGANISM: Homo sapiens

<400> SEQUENCE: 58

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

```
<210> SEQ ID NO 59
<211> LENGTH: 32
<212> TYPE: PRT
<213> ORGANISM: Homo sapiens

<400> SEQUENCE: 59

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 60
<211> LENGTH: 11
<212> TYPE: PRT
<213> ORGANISM: Homo sapiens

<400> SEQUENCE: 60

Trp Gly Gln Gly Thr Leu Val Thr Val Ser Ser
1               5                   10

<210> SEQ ID NO 61
<211> LENGTH: 10
<212> TYPE: PRT
<213> ORGANISM: Homo sapiens

<400> SEQUENCE: 61

Phe Gly Gln Gly Thr Lys Leu Glu Ile Lys
1               5                   10

<210> SEQ ID NO 62
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 62

Gly Tyr Thr Phe Asp Ala His Trp Ile Glu
1               5                   10

<210> SEQ ID NO 63
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 63

Gly Tyr Thr Phe Ile Pro Tyr Trp Ile Glu
1               5                   10

<210> SEQ ID NO 64
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 64

Gly Tyr Thr Phe Leu Pro Tyr Trp Ile Glu
1               5                   10
```

```
<210> SEQ ID NO 65
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 65

Gly Tyr Thr Phe Arg Pro Tyr Trp Ile Glu
1               5                   10

<210> SEQ ID NO 66
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 66

Gly Tyr Thr Phe Asn Pro Tyr Trp Ile Glu
1               5                   10

<210> SEQ ID NO 67
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 67

Gly Tyr Thr Phe Ser Ser Tyr Trp Ile Glu
1               5                   10

<210> SEQ ID NO 68
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 68

Gly Tyr Thr Phe Thr Pro Tyr Trp Ile Glu
1               5                   10

<210> SEQ ID NO 69
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 69

Gly Tyr Thr Phe Ser Ser His Trp Ile Glu
1               5                   10

<210> SEQ ID NO 70
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 70
```

Gly Tyr Thr Phe Ser Pro Phe Trp Ile Glu
1               5                   10

<210> SEQ ID NO 71
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 71

Gly Tyr Thr Phe Pro Pro Tyr Trp Ile Glu
1               5                   10

<210> SEQ ID NO 72
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 72

Gly Tyr Thr Phe Tyr Pro Tyr Trp Ile Glu
1               5                   10

<210> SEQ ID NO 73
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 73

Gly Tyr Thr Phe Pro Thr Tyr Trp Ile Glu
1               5                   10

<210> SEQ ID NO 74
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 74

Gly Tyr Thr Phe Ser Pro His Trp Ile Glu
1               5                   10

<210> SEQ ID NO 75
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 75

Gly Tyr Thr Phe Gly Thr Tyr Trp Ile Glu
1               5                   10

<210> SEQ ID NO 76
<211> LENGTH: 10
<212> TYPE: PRT
<213> ORGANISM: Artificial sequence
<220> FEATURE:
<223> OTHER INFORMATION: Murine CDR or mutagens thereof in Human IgG -continued variable domain frameworks

<400> SEQUENCE: 76

Gly Tyr Thr Phe Ala Pro Tyr Trp Ile Glu
1               5                   10

<210> SEQ ID NO 77
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 77

Gly Tyr Thr Phe Val Thr Tyr Trp Ile Glu
1               5                   10

<210> SEQ ID NO 78
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 78

Gly Tyr Thr Phe Gly Pro Phe Trp Ile Glu
1               5                   10

<210> SEQ ID NO 79
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 79

Gly Tyr Thr Phe Ile Pro His Trp Ile Glu
1               5                   10

<210> SEQ ID NO 80
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 80

Gly Tyr Thr Phe Gly Pro His Trp Ile Glu
1               5                   10

<210> SEQ ID NO 81
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 81

Gly Phe Thr Phe Ile Thr Tyr Trp Ile Ala
1               5                   10

<210> SEQ ID NO 82
<211> LENGTH: 10

```
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 82

Gly Tyr Thr Phe Gly Pro Tyr Trp Ile Glu
1               5                   10

<210> SEQ ID NO 83
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks
<220> FEATURE:
<221> NAME/KEY: MUTAGEN
<222> LOCATION: (5)..(5)
<223> OTHER INFORMATION: Xaa is selected from A, D, G, I, L, N, P, R,
      S, T, V, and Y
<220> FEATURE:
<221> NAME/KEY: MUTAGEN
<222> LOCATION: (6)..(6)
<223> OTHER INFORMATION: Xaa is selected from A, P, S, and T
<220> FEATURE:
<221> NAME/KEY: MUTAGEN
<222> LOCATION: (7)..(7)
<223> OTHER INFORMATION: Xaa is selected from F, H, and Y

<400> SEQUENCE: 83

Gly Tyr Thr Phe Xaa Xaa Xaa Trp Ile Glu
1               5                   10

<210> SEQ ID NO 84
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 84

Asp Ile Leu Pro Gly Ser Gly Phe Thr Asp
1               5                   10

<210> SEQ ID NO 85
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 85

Asp Ile Ile Pro Gly Thr Gly Tyr Thr Thr
1               5                   10

<210> SEQ ID NO 86
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 86

Asp Ile Leu Pro Gly Ser Gly Phe Thr Thr
1               5                   10
```

```
<210> SEQ ID NO 87
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 87

Asp Ile Ile Pro Gly Thr Gly Phe Thr Asn
1               5                   10

<210> SEQ ID NO 88
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 88

Asp Ile Leu Pro Gly Ser Gly Tyr Thr Thr
1               5                   10

<210> SEQ ID NO 89
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 89

Asp Ile Leu Pro Gly Thr Gly Tyr Thr Leu
1               5                   10

<210> SEQ ID NO 90
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 90

Asp Ile Leu Pro Gly Thr Gly Ala Thr His
1               5                   10

<210> SEQ ID NO 91
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 91

Asp Ile Leu Pro Gly Ser Gly Phe Thr His
1               5                   10

<210> SEQ ID NO 92
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 92
```

Asp Ile Leu Pro Gly Thr Gly Tyr Thr Trp
1               5                   10

<210> SEQ ID NO 93
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 93

Asp Ile Ile Pro Gly Thr Gly Tyr Thr Asn
1               5                   10

<210> SEQ ID NO 94
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 94

Asp Ile Leu Pro Gly Thr Gly Phe Thr Asn
1               5                   10

<210> SEQ ID NO 95
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 95

Asp Ile Ile Pro Gly Thr Gly Trp Thr Asn
1               5                   10

<210> SEQ ID NO 96
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 96

Asp Ile Leu Pro Gly Ser Gly Tyr Thr Ile
1               5                   10

<210> SEQ ID NO 97
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 97

Asp Ile Leu Pro Gly Thr Gly His Thr Thr
1               5                   10

<210> SEQ ID NO 98
<211> LENGTH: 10
<212> TYPE: PRT
<213> ORGANISM: Artificial sequence
<220> FEATURE:

<223> OTHER INFORMATION: Murine CDR or mutagens thereof in Human IgG
      variable domain frameworks

<400> SEQUENCE: 98

Asp Ile Leu Pro Gly Thr Gly Phe Thr Thr
1               5                   10

<210> SEQ ID NO 99
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 99

Asp Ile Leu Pro Gly Thr Gly Tyr Thr Val
1               5                   10

<210> SEQ ID NO 100
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 100

Asp Ile Ile Pro Gly Ser Gly Trp Thr Asn
1               5                   10

<210> SEQ ID NO 101
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 101

Asp Ile Leu Pro Gly Ser Gly Tyr Thr Asn
1               5                   10

<210> SEQ ID NO 102
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 102

Asp Ile Leu Pro Gly Ser Gly Trp Thr Asn
1               5                   10

<210> SEQ ID NO 103
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 103

Asp Ile Leu Pro Gly Ser Gly His Thr Thr
1               5                   10

<210> SEQ ID NO 104

```
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 104

Asp Ile Leu Pro Gly Thr Gly Tyr Thr Asn
1               5                   10

<210> SEQ ID NO 105
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 105

Asp Ile Leu Pro Ala Ser Ser Ser Thr Asn
1               5                   10

<210> SEQ ID NO 106
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 106

Asp Ile Leu Pro Gly Ser Gly His Thr Ile
1               5                   10

<210> SEQ ID NO 107
<211> LENGTH: 10
<212> TYPE: PRT
<213> ORGANISM: Artificial sequence
<220> FEATURE:
<223> OTHER INFORMATION: Murine CDR or mutagens thereof in Human IgG
      variable domain frameworks
<220> FEATURE:
<221> NAME/KEY: MUTAGEN
<222> LOCATION: (3)..(3)
<223> OTHER INFORMATION: Xaa is selected from  I and L
<220> FEATURE:
<221> NAME/KEY: MUTAGEN
<222> LOCATION: (6)..(6)
<223> OTHER INFORMATION: Xaa is selected from S and T
<220> FEATURE:
<221> NAME/KEY: MUTAGEN
<222> LOCATION: (8)..(8)
<223> OTHER INFORMATION: Xaa is selected from A, F, H, and W
<220> FEATURE:
<221> NAME/KEY: MUTAGEN
<222> LOCATION: (10)..(10)
<223> OTHER INFORMATION: Xaa is selected from D, H, I, L, and N

<400> SEQUENCE: 107

Asp Ile Xaa Pro Gly Xaa Gly Xaa Thr Xaa
1               5                   10

<210> SEQ ID NO 108
<211> LENGTH: 17
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 108
```

Lys Ser Ser Gln Ser Leu Leu Trp Phe Val Asn Gln Lys Asn Tyr Leu
1               5                   10                  15
Thr

<210> SEQ ID NO 109
<211> LENGTH: 17
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 109

Lys Ser Ser Gln Ser Leu Leu Tyr Val Tyr Gly Gln Lys Asn Tyr Leu
1               5                   10                  15
Thr

<210> SEQ ID NO 110
<211> LENGTH: 17
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 110

Lys Ser Ser Gln Ser Leu Leu Phe Arg Pro Thr Gln Lys Asn Tyr Leu
1               5                   10                  15
Thr

<210> SEQ ID NO 111
<211> LENGTH: 17
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 111

Lys Ser Ser Gln Ser Leu Leu Tyr Thr Ser Asn Gln Lys Asn Tyr Leu
1               5                   10                  15
Thr

<210> SEQ ID NO 112
<211> LENGTH: 17
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 112

Lys Ser Ser Gln Ser Leu Leu Tyr Ser Gly Asn Gln Arg Asn Tyr Leu
1               5                   10                  15
Thr

<210> SEQ ID NO 113
<211> LENGTH: 17
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 113

```
Lys Ser Ser Gln Ser Leu Leu Pro Ser Trp Asn Gln Ser Asn Tyr Leu
1               5                   10                  15

Thr

<210> SEQ ID NO 114
<211> LENGTH: 17
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 114

Lys Ser Ser Gln Ser Leu Leu Phe Ser Ala Asn Gln Arg Asn Tyr Leu
1               5                   10                  15

Thr

<210> SEQ ID NO 115
<211> LENGTH: 17
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 115

Lys Ser Ser Gln Ser Leu Leu Thr Ser Tyr Asn Gln Arg Asn Tyr Leu
1               5                   10                  15

Thr

<210> SEQ ID NO 116
<211> LENGTH: 17
<212> TYPE: PRT
<213> ORGANISM: Artificial sequence
<220> FEATURE:
<223> OTHER INFORMATION: Murine CDR or mutagens thereof in Human IgG
      variable domain frameworks
<220> FEATURE:
<221> NAME/KEY: MUTAGEN
<222> LOCATION: (8)..(8)
<223> OTHER INFORMATION: Xaa is selected from F, P, S, T, W, and Y
<220> FEATURE:
<221> NAME/KEY: MUTAGEN
<222> LOCATION: (9)..(9)
<223> OTHER INFORMATION: Xaa is selected from F, S, T, R, and V
<220> FEATURE:
<221> NAME/KEY: MUTAGEN
<222> LOCATION: (10)..(10)
<223> OTHER INFORMATION: Xaa is selected from A, G, P, S, W, Y, and V
<220> FEATURE:
<221> NAME/KEY: MUTAGEN
<222> LOCATION: (11)..(11)
<223> OTHER INFORMATION: Xaa is selected from G, N, and T
<220> FEATURE:
<221> NAME/KEY: MUTAGEN
<222> LOCATION: (13)..(13)
<223> OTHER INFORMATION: Xaa is selected from K, R, and S

<400> SEQUENCE: 116

Lys Ser Ser Gln Ser Leu Leu Xaa Xaa Xaa Xaa Gln Xaa Asn Tyr Leu
1               5                   10                  15

Thr

<210> SEQ ID NO 117
<211> LENGTH: 7
<212> TYPE: PRT
<213> ORGANISM: Artificial sequence
<220> FEATURE:
```

```
<223> OTHER INFORMATION: Murine CDR or mutagens thereof in Human IgG
      variable domain frameworks

<400> SEQUENCE: 117

His Ala Ser Thr Arg Glu Ser
1               5

<210> SEQ ID NO 118
<211> LENGTH: 7
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 118

Trp Ala Ser Thr Arg Ser Ser
1               5

<210> SEQ ID NO 119
<211> LENGTH: 7
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 119

Trp Ala Ser Thr Arg Asp Ser
1               5

<210> SEQ ID NO 120
<211> LENGTH: 7
<212> TYPE: PRT
<213> ORGANISM: Artificial sequence
<220> FEATURE:
<223> OTHER INFORMATION: Murine CDR or mutagens thereof in Human IgG
      variable domain frameworks
<220> FEATURE:
<221> NAME/KEY: MUTAGEN
<222> LOCATION: (1)..(1)
<223> OTHER INFORMATION: Xaa is selected from H and W
<220> FEATURE:
<221> NAME/KEY: MUTAGEN
<222> LOCATION: (6)..(6)
<223> OTHER INFORMATION: Xaa is selected from D, E, and S

<400> SEQUENCE: 120

Xaa Ala Ser Thr Arg Xaa Ser
1               5

<210> SEQ ID NO 121
<211> LENGTH: 9
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 121

Gln Asn Asp Phe Ser Trp Pro Leu Thr
1               5

<210> SEQ ID NO 122
<211> LENGTH: 9
<212> TYPE: PRT
<213> ORGANISM: Artificial sequence
<220> FEATURE:
<223> OTHER INFORMATION: Murine CDR or mutagens thereof in Human IgG
      variable domain frameworks
```

```
<400> SEQUENCE: 122

Gln Asn Asp Asp Ser Tyr Pro Leu Thr
1               5

<210> SEQ ID NO 123
<211> LENGTH: 9
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 123

Gln Asn Asp Asp Tyr Trp Pro Leu Thr
1               5

<210> SEQ ID NO 124
<211> LENGTH: 9
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 124

Gln Asn Asp Asp Thr Tyr Pro Met Thr
1               5

<210> SEQ ID NO 125
<211> LENGTH: 9
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 125

Gln Asn Asp Phe Thr Tyr Pro Leu Thr
1               5

<210> SEQ ID NO 126
<211> LENGTH: 9
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 126

Gln Asn Asp Asp Thr Tyr Pro Leu Thr
1               5

<210> SEQ ID NO 127
<211> LENGTH: 9
<212> TYPE: PRT
<213> ORGANISM: Artificial sequence
<220> FEATURE:
<223> OTHER INFORMATION: Murine CDR or mutagens thereof in Human IgG
      variable domain frameworks

<400> SEQUENCE: 127

Gln Asn Asp Leu Thr Tyr Pro Leu Thr
1               5

<210> SEQ ID NO 128
<211> LENGTH: 9
<212> TYPE: PRT
```

<213> ORGANISM: Artificial sequence
<220> FEATURE:
<223> OTHER INFORMATION: Murine CDR or mutagens thereof in Human IgG
      variable domain frameworks
<220> FEATURE:
<221> NAME/KEY: MUTAGEN
<222> LOCATION: (4)..(4)
<223> OTHER INFORMATION: Xaa is selected from D, F, and L
<220> FEATURE:
<221> NAME/KEY: MUTAGEN
<222> LOCATION: (5)..(5)
<223> OTHER INFORMATION: Xaa is selected from S, T, and Y
<220> FEATURE:
<221> NAME/KEY: MUTAGEN
<222> LOCATION: (6)..(6)
<223> OTHER INFORMATION: Xaa is selected from W and Y
<220> FEATURE:
<221> NAME/KEY: MUTAGEN
<222> LOCATION: (8)..(8)
<223> OTHER INFORMATION: Xaa is selected from L and M

<400> SEQUENCE: 128

Gln Asn Asp Xaa Xaa Xaa Pro Xaa Thr
1               5

<210> SEQ ID NO 129
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 129

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Gly Pro Tyr
            20                  25                  30

Trp Ile Glu Trp Val Arg Gln Met Pro Gly Lys Gly Leu Glu Trp Met
        35                  40                  45

Gly Asp Ile Ile Pro Gly Ser Gly Trp Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 130
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 130

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Val Thr Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Tyr Thr Val Tyr Ser Pro Ser Phe
    50                  55                  60

```
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Gly Tyr Tyr Gly Asn Ser Gly Phe Ala Tyr
            100                 105

<210> SEQ ID NO 131
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 131

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Ser Pro Phe
                 20                  25                  30

Trp Ile Glu Trp Val Arg Gln Met Pro Gly Lys Gly Leu Glu Trp Met
             35                  40                  45

Gly Asp Ile Ile Pro Gly Thr Gly Tyr Thr Asn Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Gly Tyr Tyr Gly Asn Ser Gly Phe Ala Tyr
            100                 105

<210> SEQ ID NO 132
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 132

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Pro Thr Tyr
                 20                  25                  30

Trp Ile Glu Trp Val Arg Gln Met Pro Gly Lys Gly Leu Glu Trp Met
             35                  40                  45

Gly Asp Ile Ile Pro Gly Thr Gly Trp Thr Asn Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Gly Tyr Tyr Gly Asn Ser Gly Phe Ala Tyr
            100                 105

<210> SEQ ID NO 133
<211> LENGTH: 109
<212> TYPE: PRT
<213> ORGANISM: Artificial Sequence
<220> FEATURE:
```

```
<223> OTHER INFORMATION: Murine CDR or mutagens thereof in Human IgG
      variable domain frameworks

<400> SEQUENCE: 133

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ile Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Ser Gly Phe Thr Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 134
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 134

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Gly Pro Phe
            20                  25                  30

Trp Ile Glu Trp Val Arg Gln Met Pro Gly Lys Gly Leu Glu Trp Met
        35                  40                  45

Gly Asp Ile Leu Pro Gly Ser Gly Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 135
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 135

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Gly Pro His
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Tyr Thr Asn Tyr Ser Pro Ser Phe
    50                  55                  60
```

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Ser Gly Tyr Tyr Gly Asn Ser Gly Phe Ala Tyr
            100                 105

<210> SEQ ID NO 136
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 136

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Leu Pro Tyr
            20                  25                  30

Trp Ile Glu Trp Val Arg Gln Met Pro Gly Lys Gly Leu Glu Trp Met
        35                  40                  45

Gly Asp Ile Ile Pro Gly Thr Gly Phe Thr Asn Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Ser Gly Tyr Tyr Gly Asn Ser Gly Phe Ala Tyr
            100                 105

<210> SEQ ID NO 137
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 137

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Arg Pro Tyr
            20                  25                  30

Trp Ile Glu Trp Val Arg Gln Met Pro Gly Lys Gly Leu Glu Trp Met
        35                  40                  45

Gly Asp Ile Ile Pro Gly Thr Gly Tyr Thr Asn Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Ser Gly Tyr Tyr Gly Asn Ser Gly Phe Ala Tyr
            100                 105

<210> SEQ ID NO 138
<211> LENGTH: 109
<212> TYPE: PRT
<213> ORGANISM: Artificial Sequence
<220> FEATURE:

<223> OTHER INFORMATION: Murine CDR or mutagens thereof in Human IgG
variable domain frameworks

<400> SEQUENCE: 138

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ser Pro His
            20                  25                  30

Trp Ile Glu Trp Val Arg Gln Met Pro Gly Lys Gly Leu Glu Trp Met
        35                  40                  45

Gly Asp Ile Leu Pro Gly Ser Gly Tyr Thr Ile Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 139
<211> LENGTH: 109
<212> TYPE: PRT
<213> ORGANISM: Artificial Sequence
<220> FEATURE:
<223> OTHER INFORMATION: Murine CDR or mutagens thereof in Human IgG
variable domain frameworks

<400> SEQUENCE: 139

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ala Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Phe Thr Thr Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 140
<211> LENGTH: 109
<212> TYPE: PRT
<213> ORGANISM: Artificial Sequence
<220> FEATURE:
<223> OTHER INFORMATION: Murine CDR or mutagens thereof in Human IgG
variable domain frameworks

<400> SEQUENCE: 140

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Pro Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Tyr Thr Val Tyr Ser Pro Ser Phe
50                  55                  60

```
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Gly Tyr Tyr Gly Asn Ser Gly Phe Ala Tyr
            100                 105

<210> SEQ ID NO 141
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 141

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Tyr Pro Tyr
                 20                  25                  30

Trp Ile Glu Trp Val Arg Gln Met Pro Gly Lys Gly Leu Glu Trp Met
             35                  40                  45

Gly Asp Ile Leu Pro Gly Thr Gly Phe Thr Asn Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Gly Tyr Tyr Gly Asn Ser Gly Phe Ala Tyr
            100                 105

<210> SEQ ID NO 142
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 142

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Pro Tyr
                 20                  25                  30

Trp Ile Glu Trp Val Arg Gln Met Pro Gly Lys Gly Leu Glu Trp Met
             35                  40                  45

Gly Asp Ile Leu Pro Gly Ser Gly His Thr Thr Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Gly Tyr Tyr Gly Asn Ser Gly Phe Ala Tyr
            100                 105

<210> SEQ ID NO 143
<211> LENGTH: 109
<212> TYPE: PRT
<213> ORGANISM: Artificial Sequence
<220> FEATURE:
```

<223> OTHER INFORMATION: Murine CDR or mutagens thereof in Human IgG
       variable domain frameworks

<400> SEQUENCE: 143

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ser Ser Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Ala Thr His Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105
```

<210> SEQ ID NO 144
<211> LENGTH: 109
<212> TYPE: PRT
<213> ORGANISM: Artificial Sequence
<220> FEATURE:
<223> OTHER INFORMATION: Murine CDR or mutagens thereof in Human IgG
       variable domain frameworks

<400> SEQUENCE: 144

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Tyr Thr Val Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105
```

<210> SEQ ID NO 145
<211> LENGTH: 109
<212> TYPE: PRT
<213> ORGANISM: Artificial Sequence
<220> FEATURE:
<223> OTHER INFORMATION: Murine CDR or mutagens thereof in Human IgG
       variable domain frameworks

<400> SEQUENCE: 145

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Gly Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Tyr Thr Leu Tyr Ser Pro Ser Phe
    50                  55                  60
```

```
Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 146
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 146

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Gly Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Tyr Thr Val Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 147
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 147

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Asp Ala His
            20                  25                  30

Trp Ile Glu Trp Val Arg Gln Met Pro Gly Lys Gly Leu Glu Trp Met
        35                  40                  45

Gly Asp Ile Leu Pro Gly Ser Gly Phe Thr Asp Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 148
<211> LENGTH: 109
<212> TYPE: PRT
<213> ORGANISM: Artificial Sequence
<220> FEATURE:
```

```
<223> OTHER INFORMATION: Murine CDR or mutagens thereof in Human IgG
      variable domain frameworks

<400> SEQUENCE: 148

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ala Pro Tyr
                20                  25                  30

Trp Ile Glu Trp Val Arg Gln Met Pro Gly Lys Gly Leu Glu Trp Met
            35                  40                  45

Gly Asp Ile Leu Pro Gly Thr Gly Tyr Thr Trp Tyr Ser Pro Ser Phe
50                      55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
                100                 105

<210> SEQ ID NO 149
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 149

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Gly Thr Tyr
                20                  25                  30

Trp Ile Glu Trp Val Arg Gln Met Pro Gly Lys Gly Leu Glu Trp Met
            35                  40                  45

Gly Asp Ile Leu Pro Gly Thr Gly His Thr Tyr Tyr Ser Pro Ser Phe
50                      55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
                100                 105

<210> SEQ ID NO 150
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 150

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ile Pro His
                20                  25                  30

Trp Ile Glu Trp Val Arg Gln Met Pro Gly Lys Gly Leu Glu Trp Met
            35                  40                  45

Gly Asp Ile Leu Pro Gly Ser Gly Trp Thr Asn Tyr Ser Pro Ser Phe
50                      55                  60
```

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 151
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 151

Glu Val Gln Leu Val Gln Ser Gly Ala Glu Val Lys Lys Pro Gly Glu
1               5                   10                  15

Ser Leu Arg Ile Ser Cys Lys Gly Ser Gly Phe Thr Phe Ile Thr Tyr
                20                  25                  30

Trp Ile Ala Trp Val Arg Gln Met Pro Gly Lys Gly Leu Glu Trp Met
                35                  40                  45

Gly Asp Ile Leu Pro Ala Ser Ser Ser Thr Asn Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 152
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 152

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Gly Pro Tyr
                20                  25                  30

Trp Ile Glu Trp Val Arg Gln Met Pro Gly Lys Gly Leu Glu Trp Met
                35                  40                  45

Gly Asp Ile Leu Pro Gly Ser Gly His Thr Ile Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105

<210> SEQ ID NO 153
<211> LENGTH: 109
<212> TYPE: PRT
<213> ORGANISM: Artificial Sequence
<220> FEATURE:

<223> OTHER INFORMATION: Murine CDR or mutagens thereof in Human IgG
    variable domain frameworks

<400> SEQUENCE: 153

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ala Pro Tyr
            20                  25                  30

Trp Ile Glu Trp Val Arg Gln Met Pro Gly Lys Gly Leu Glu Trp Met
        35                  40                  45

Gly Asp Ile Ile Pro Gly Thr Gly Tyr Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105
```

<210> SEQ ID NO 154
<211> LENGTH: 109
<212> TYPE: PRT
<213> ORGANISM: Artificial Sequence
<220> FEATURE:
<223> OTHER INFORMATION: Murine CDR or mutagens thereof in Human IgG
    variable domain frameworks

<400> SEQUENCE: 154

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Gly Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Ser Gly Tyr Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr
            100                 105
```

<210> SEQ ID NO 155
<211> LENGTH: 109
<212> TYPE: PRT
<213> ORGANISM: Artificial Sequence
<220> FEATURE:
<223> OTHER INFORMATION: Murine CDR or mutagens thereof in Human IgG
    variable domain frameworks

<400> SEQUENCE: 155

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Asn Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Tyr Thr Asn Tyr Ser Pro Ser Phe
    50                  55                  60
```

-continued

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Ser Gly Tyr Tyr Gly Asn Ser Gly Phe Ala Tyr
            100                 105

<210> SEQ ID NO 156
<211> LENGTH: 109
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 156

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ser Ser His
            20                  25                  30

Trp Ile Glu Trp Val Arg Gln Met Pro Gly Lys Gly Leu Glu Trp Met
        35                  40                  45

Gly Asp Ile Leu Pro Gly Ser Gly Phe Thr His Tyr Ser Pro Ser Phe
    50                  55                  60

Gln Gly His Val Thr Ile Ser Ala Asp Lys Ser Ile Ser Thr Ala Tyr
65                  70                  75                  80

Leu Lys Trp Ser Ser Leu Lys Ala Ser Asp Thr Ala Met Tyr Tyr Cys
            85                  90                  95

Ala Arg Ser Gly Tyr Tyr Gly Asn Ser Gly Phe Ala Tyr
            100                 105

<210> SEQ ID NO 157
<211> LENGTH: 103
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 157

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Trp Phe
            20                  25                  30

Val Asn Gln Lys Asn Tyr Leu Thr Trp Tyr Leu Gln Lys Pro Gly Gln
        35                  40                  45

Ser Pro Gln Leu Leu Ile Tyr His Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
            85                  90                  95

Asp Asp Ser Tyr Pro Leu Thr
            100

<210> SEQ ID NO 158
<211> LENGTH: 103
<212> TYPE: PRT
<213> ORGANISM: Artificial Sequence
<220> FEATURE:

<223> OTHER INFORMATION: Murine CDR or mutagens thereof in Human IgG
    variable domain frameworks

<400> SEQUENCE: 158

```
Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Gly Asn Gln Arg Asn Tyr Leu Thr Trp Tyr Leu Gln Lys Pro Gly Gln
        35                  40                  45

Ser Pro Gln Leu Leu Ile Tyr Trp Ala Ser Thr Arg Ser Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Asp Thr Tyr Pro Met Thr
            100
```

<210> SEQ ID NO 159
<211> LENGTH: 103
<212> TYPE: PRT
<213> ORGANISM: Artificial Sequence
<220> FEATURE:
<223> OTHER INFORMATION: Murine CDR or mutagens thereof in Human IgG
    variable domain frameworks

<400> SEQUENCE: 159

```
Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Pro Ser
            20                  25                  30

Trp Asn Gln Ser Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Phe Thr Tyr Pro Leu Thr
            100
```

<210> SEQ ID NO 160
<211> LENGTH: 103
<212> TYPE: PRT
<213> ORGANISM: Artificial Sequence
<220> FEATURE:
<223> OTHER INFORMATION: Murine CDR or mutagens thereof in Human IgG
    variable domain frameworks

<400> SEQUENCE: 160

```
Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Phe Ser
            20                  25                  30

Ala Asn Gln Arg Asn Tyr Leu Thr Trp Tyr Leu Gln Lys Pro Gly Gln
        35                  40                  45

Ser Pro Gln Leu Leu Ile Tyr Trp Ala Ser Thr Arg Asp Ser Gly Val
    50                  55                  60
```

```
Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Asn
                 85                  90                  95

Asp Asp Thr Tyr Pro Leu Thr
            100

<210> SEQ ID NO 161
<211> LENGTH: 103
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 161

Asp Ile Val Met Thr Gln Thr Pro Leu Ser Leu Pro Val Thr Pro Gly
  1               5                  10                  15

Glu Pro Ala Ser Ile Ser Cys Lys Ser Gln Ser Leu Leu Thr Ser
                 20                  25                  30

Tyr Asn Gln Arg Asn Tyr Leu Thr Trp Tyr Leu Gln Lys Pro Gly Gln
             35                  40                  45

Ser Pro Gln Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Asn
                 85                  90                  95

Asp Leu Thr Tyr Pro Leu Thr
            100

<210> SEQ ID NO 162
<211> LENGTH: 103
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 162

Asp Ile Val Met Thr Gln Thr Pro Leu Ser Leu Pro Val Thr Pro Gly
  1               5                  10                  15

Glu Pro Ala Ser Ile Ser Cys Lys Ser Gln Ser Leu Leu Tyr Val
                 20                  25                  30

Tyr Gly Gln Lys Asn Tyr Leu Thr Trp Tyr Leu Gln Lys Pro Gly Gln
             35                  40                  45

Ser Pro Gln Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Asn
                 85                  90                  95

Asp Phe Ser Trp Pro Leu Thr
            100

<210> SEQ ID NO 163
<211> LENGTH: 103
<212> TYPE: PRT
<213> ORGANISM: Artificial Sequence
<220> FEATURE:
```

```
<223> OTHER INFORMATION: Murine CDR or mutagens thereof in Human IgG
      variable domain frameworks

<400> SEQUENCE: 163

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Phe Arg
            20                  25                  30

Pro Thr Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Asp Ser Tyr Pro Leu Thr
            100

<210> SEQ ID NO 164
<211> LENGTH: 103
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 164

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Tyr Thr
            20                  25                  30

Ser Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Asp Tyr Trp Pro Leu Thr
            100

<210> SEQ ID NO 165
<211> LENGTH: 220
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 165

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ser Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60
```

```
Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Thr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 166
<211> LENGTH: 450
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 166

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ala Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Phe Thr Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 167
<211> LENGTH: 450
<212> TYPE: PRT
<213> ORGANISM: Artificial Sequence
<220> FEATURE:
<223> OTHER INFORMATION: Murine CDR or mutagens thereof in Human IgG
      variable domain frameworks

<400> SEQUENCE: 167

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ala Pro Tyr
            20                  25                  30

Trp Ile Glu Trp Val Arg Gln Met Pro Gly Lys Gly Leu Glu Trp Met
        35                  40                  45

Gly Asp Ile Leu Pro Gly Thr Gly Phe Thr Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr Trp Gly Gln
            100                 105                 110
```

-continued

```
Gly Thr Leu Val Thr Val Ser Ser Ala Ser Thr Lys Gly Pro Ser Val
        115             120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Asp Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Glu Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450
```